US009309311B2

(12) United States Patent
Gurney et al.

(10) Patent No.: US 9,309,311 B2

(45) **Date of Patent: *Apr. 12, 2016**

(54) METHOD FOR MAKING HETEROMULTIMERIC MOLECULES

(71) Applicant: OncoMed Pharmaceuticals, Inc., Redwood City, CA (US)

(72) Inventors: Austin L. Gurney, San Francisco, CA (US); Aaron K. Sato, Burlingame, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 13/801,189

(22) Filed: Mar. 13, 2013

(65) Prior Publication Data

US 2013/0253172 A1 Sep. 26, 2013

Related U.S. Application Data

(62) Division of application No. 12/768,650, filed on Apr. 27, 2010.

(60) Provisional application No. 61/173,129, filed on Apr. 27, 2009, provisional application No. 61/177,412, filed on May 12, 2009.

(51) Int. Cl.

| | |
|---|---|
| ***C12P 21/04*** | (2006.01) |
| ***C07K 16/22*** | (2006.01) |
| ***C07K 16/18*** | (2006.01) |
| ***C07K 16/46*** | (2006.01) |
| *A61K 47/48* | (2006.01) |
| *C12N 15/00* | (2006.01) |

(52) U.S. Cl.

CPC ................ *C07K 16/22* (2013.01); *C07K 16/18* (2013.01); *C07K 16/468* (2013.01); *A61K 47/48546* (2013.01); *C07K 2316/96* (2013.01); *C07K 2317/20* (2013.01); *C07K 2317/31* (2013.01); *C07K 2317/52* (2013.01); *C07K 2317/526* (2013.01); *C07K 2317/55* (2013.01); *C07K 2317/565* (2013.01); *C07K 2317/73* (2013.01); *C07K 2317/76* (2013.01); *C12N 15/00* (2013.01)

(58) Field of Classification Search

None

See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 4,816,567 A | 3/1989 | Cabilly et al. |
| 5,013,556 A | 5/1991 | Woodle et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,693,761 A | 12/1997 | Queen et al. |
| 5,693,762 A | 12/1997 | Queen et al. |
| 5,731,168 A | 3/1998 | Carter et al. |
| 5,750,373 A | 5/1998 | Garrard et al. |
| 5,807,706 A | 9/1998 | Carter et al. |
| 5,821,333 A | 10/1998 | Carter et al. |
| 5,840,299 A | 11/1998 | Bendig et al. |
| 6,833,441 B2 | 12/2004 | Wang et al. |
| 7,183,076 B2 | 2/2007 | Arathoon et al. |
| 7,642,228 B2 | 1/2010 | Carter et al. |
| 7,695,936 B2 | 4/2010 | Carter et al. |
| 7,750,124 B2 | 7/2010 | Gurney et al. |
| 7,758,859 B2 | 7/2010 | Fuh et al. |
| 7,951,917 B1 | 5/2011 | Arathoon et al. |
| 8,048,418 B2 | 11/2011 | Noguera-Troise et al. |
| 8,216,805 B2 | 7/2012 | Carter et al. |
| 8,592,563 B2 | 11/2013 | Bates et al. |
| 8,642,745 B2 | 2/2014 | Arathoon et al. |
| 8,679,785 B2 | 3/2014 | Carter et al. |
| 8,765,412 B2 | 7/2014 | Arathoon et al. |
| 8,858,941 B2 | 10/2014 | Gurney et al. |
| 9,067,986 B2 | 6/2015 | Gurney et al. |
| 2005/0079184 A1 | 4/2005 | Hsing-Chang et al. |
| 2005/0170398 A1 | 8/2005 | Van Berkel et al. |
| 2007/0004909 A1 | 1/2007 | Johnson et al. |
| 2007/0213266 A1 | 9/2007 | Gill et al. |
| 2007/0287170 A1 | 12/2007 | Davis et al. |
| 2008/0063635 A1 | 3/2008 | Takahashi et al. |

(Continued)

FOREIGN PATENT DOCUMENTS

| | | |
|---|---|---|
| CN | 1176659 A | 3/1998 |
| CN | 1511850 A | 7/2004 |

(Continued)

OTHER PUBLICATIONS

Portolano et Al., Journal of Immunology, 1993, 150(3): 880-887.*

(Continued)

*Primary Examiner* — Hong Sang

(74) *Attorney, Agent, or Firm* — Sterne, Kessler, Goldstein & Fox P.L.L.C.

(57) ABSTRACT

Methods for making heteromultimeric molecules, such as bispecific antibodies, and compositions comprising these molecules are disclosed. The methods include introducing mutations in amino acids that are in contact at the interface of two polypeptides, such that the electrostatic interaction between the ion pairs is altered.

9 Claims, 17 Drawing Sheets

(56) References Cited

U.S. PATENT DOCUMENTS

Figure 1:
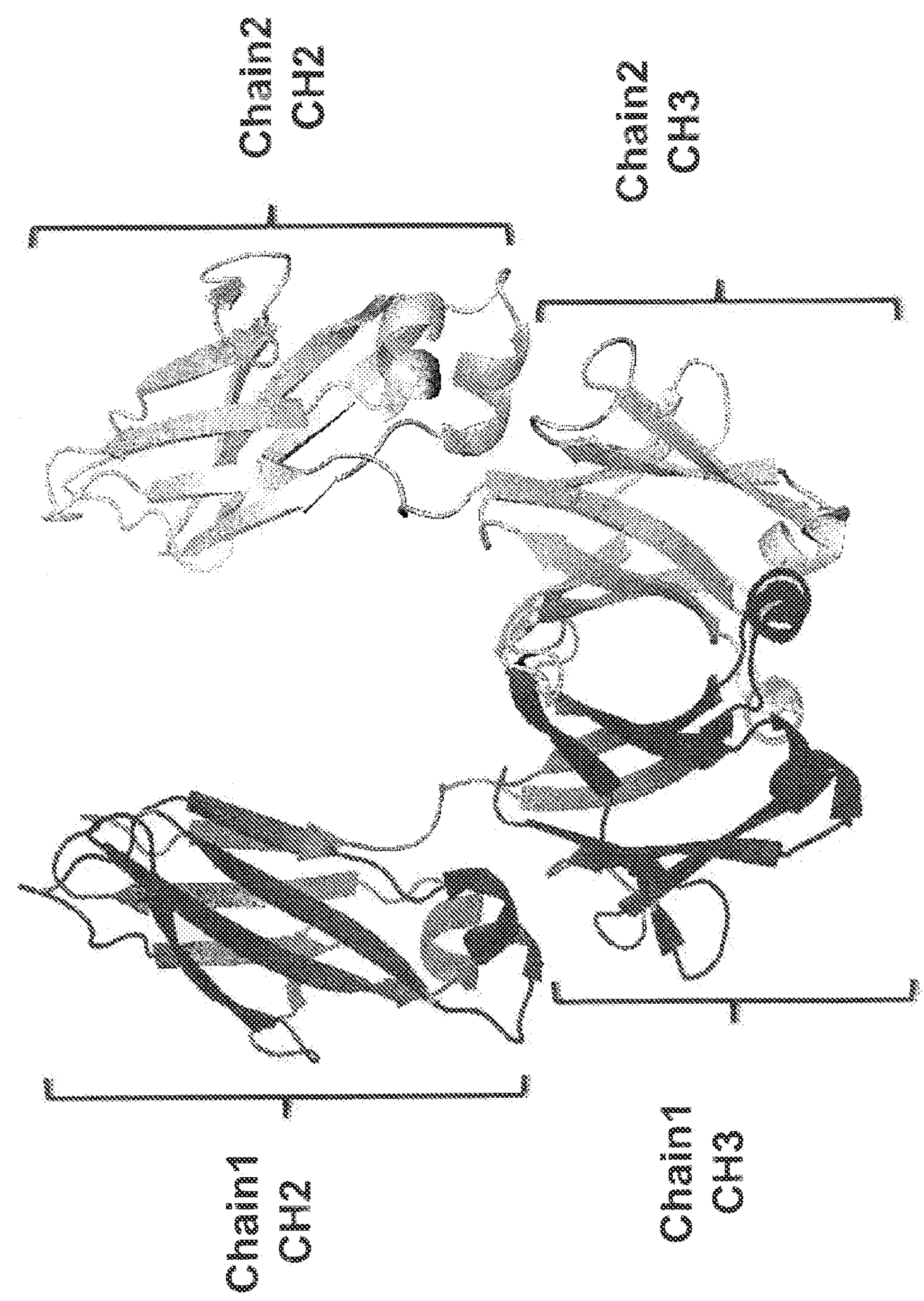

| | | | |
|---|---|---|---|
| 2008/0069820 | A1 | 3/2008 | Fuh et al. |
| 2008/0107648 | A1 | 5/2008 | Noguera et al. |
| 2008/0187532 | A1 | 8/2008 | Gurney et al. |
| 2010/0015133 | A1 | 1/2010 | Igawa et al. |
| 2010/0076178 | A1 | 3/2010 | Ghayur et al. |
| 2010/0129356 | A1 | 5/2010 | Yan |
| 2011/0123532 | A1 | 5/2011 | Gurney et al. |
| 2011/0172398 | A1 | 7/2011 | Borges et al. |
| 2011/0217237 | A1 | 9/2011 | Chen et al. |
| 2012/0116057 | A1 | 5/2012 | Kannan et al. |
| 2013/0253172 | A1 | 9/2013 | Gurney et al. |

FOREIGN PATENT DOCUMENTS

| | | | |
|---|---|---|---|
| CN | 1558916 | A | 12/2004 |
| CN | 1668636 | A | 9/2005 |
| WO | WO 98/50431 | A2 | 11/1998 |
| WO | WO 2004/110490 | | 12/2004 |
| WO | WO 2006/028936 | A2 | 3/2006 |
| WO | WO 2006/033386 | A1 | 3/2006 |
| WO | WO 2006/106905 | A1 | 10/2006 |
| WO | WO 2006/113665 | A2 | 10/2006 |
| WO | WO 2007/110205 | A2 | 10/2007 |
| WO | WO 2007/147901 | A1 | 12/2007 |
| WO | WO 2008/042236 | A2 | 4/2008 |
| WO | WO 2008/060705 | A2 | 5/2008 |
| WO | WO 2008/133706 | A2 | 11/2008 |
| WO | WO 2009/080251 | A1 | 7/2009 |
| WO | WO 2009/089004 | A1 | 7/2009 |
| WO | WO 2010/124009 | | 10/2010 |
| WO | WO 2010/129304 | A2 | 11/2010 |
| WO | WO 2011/047442 | | 4/2011 |

OTHER PUBLICATIONS

English language Abstract of Chinese Patent No. CN 1511850 A, European Patent Office, espacenet database- Worldwide, (2004) (Listed as document FP10 on the accompanying form PTO/SB/08A).

Yan, Wei, "The Design and Engineering of Fc Heterodimers for the Production of Bispecific Antibodies," Symposium Abstract, Eleventh Annual Phage Display of Antibodies and Peptides, Approaches for 2$^{nd}$ Generation Biologics, Apr. 6-Apr. 7, 2009, Boston, Massachusetts.

Yan, Wei, "Design and Engineering of Fc Heterodimers for the Production of Bispecific Antibodies," Symposium Abstract, Keystone Symposia on Molecular and Cellular Biology, Accelerating Life Science Discovery, Mar. 27-Apr. 1, 2009, Whistler, British Columbia.

Yan, Wei, "The Design and Engineering of Fc Heterodimers for the Production of Bispecific Antibodies and Other Heterodimer Fusion Proteins," Symposium Abstract. 20$^{th}$ Annual International Conference, Antibody Engineering, Antibody Engineering and Immunotherapeutics for the 21$^{st}$ Century, Dec. 6-10, 2009, San Diego, California.

Carter, P., "Bispecific human IgG by design," *J Immunol Methods* 248:7-15, Elsevier Science B.V., Netherlands (2001).

Burgess, W.H., et al.,"Possible dissociation of the heparin-binding and mitogenic activities of heparin-binding (acidic fibroblast) growth factor-1 from its receptor-binding activities by site-directed mutagenesis of a single lysine residue," *J Cell Biol* 111(5 Pt 1):2129-2138, Rockefeller University Press, United States (1990).

Colman, P.M., "Effects of amino acid sequence changes on antibody-antigen interactions," *Research in Immunology* 145(1):33-36, Elsevier Masson SAS, France (1994).

Lazar, E., et al., "Transforming growth factor α: mutation of aspartic acid 47 and leucine 48 results in different biological activities," *Mol Cell Biol* 8(3):1247-1252, American Society for Microbiology, United States (1988).

Merchant, A.M., et al., "An efficient route to human bispecific IgG," *Nat Biotechnol* 16(7):677-681, Nature American Publishing, United States (1998).

Paul, W.E., Fundamental Immunology, 3$^{rd}$ Edition, pp. 292-295, Lippincott Williams & Wilkins, United States (1993).

Portolano, S., et al., "Lack of promiscuity in autoantigen-specific H and L chain combinations as revealed by human H and L chain 'roulette'," *J Immunol* 150(3):880-887, American Association of Immunologists, United States (1993).

Rudikoff, S., et al., "Single amino acid substitution altering antigen-binding specificity," *Proc Nati Acad Sci USA* 79(6):1979-1983, National Academy of Science, United States (1982).

Skolnick, J. and Fetrow, J.S., "From genes to protein structure and function: novel applications of computational approaches in the genomic era," *Trends in Biotechnology* 18(1):34-39, Elsevier Science Publishers B.V., Netherlands (2000).

Office Action mailed Jul. 21, 2014, in U.S. Appl. No. 12/768,650, inventors Gurney, A.L., et al., filed Apr. 27, 2010.

Office Action mailed Jul. 17, 2012, in U.S. Appl. No. 12/768,650, inventors Gurney, A.L., et al., filed Apr. 27, 2010.

Office Action mailed Apr. 5, 2013, in U.S. Appl. No. 12/768,650, inventors Gurney, A.L., et al., filed Apr. 27, 2010.

Office Action mailed Oct. 8, 2013, in U.S. Appl. No. 12/768,650, inventors Gurney, A.L., et al., filed Apr. 27, 2010.

Office Action mailed Feb. 11, 2014, in U.S. Appl. No. 12/768,650, inventors Gurney, A.L., et al., filed Apr. 27, 2010.

Barbas, III, C., et al., "In vitro evolution of a neutralizing human antibody to human immunodeficiency virus type 1 to enhance affinity and broaden strain cross-reactivity," *Proc Nat. Acad. Sci. USA* 91:3809-3813, National Academy of Sciences, United States (1994).

Bloom, J., et al., "Intrachain disulfide bond in the core hinge region of human IgG4," *Protein Science* 6:407-415, Cambridge University Press, United States (1997).

Boerner P., et al., "Production of Antigen-Specific Human Monoclonal Antibodies From In Vitro-Primed Human Splenocytes," *J. Immunol.* 147:86-95, The American Association of Immunologists, United States (1991).

Brennan, M., et al., "Preparation of Bispecific Antibodies by Chemical Recombination of Monoclonal Immunoglobin $G_1$ Fragment," *Science* 229:81-83, Nationl Academy of Sciences, United States (1985).

Carter, P., "Humanization of an anti-p185$^{HER2}$ antibody for human cancer therapy," *Proc. Natl. Acad. Sci. USA* 89:4285-4289, Academy of Sciences, United States (1992).

Chothia, C., et al., "Domain Association in Immunoglobin Molecules: The Packing of Variable Domains," *J. Mol. Biol.* 186:651-663, Academic Press, United Kingdom (1985).

Chothia, C. and Lesk, A., "Canonical Structures for the Hypervariable Regions of Immunoglobins," *J. Mol. Biol.* 196:901-917, Academic Press Limited, United States (1987).

Chowdhury, P. and Pastan, I., "Improving antibody affinity by mimicking somatic hypermutation in vitro," *Nat. Biotechnol.* 17:568-572, Nature Publishing Co., United States (1999).

Cole, S., et al., "The EBV-Hybridoma Technique and Its Application to Human Lung Cancer," pp. 77-96, Monoclonal Antibodies and Cancer Therapy, Proceedings of the Roche-UCLA Symposium, Park City, Utah, USA, Alan R. Liss, Inc., Jan. 26-Feb. 2, 1985.

Deisenhofer, J., "Crystallagraphic Refinement and Atomic Models of a Human Fc Fragment Its Complex with Fragment B of Protein A from *Staphyloccocus aureus* at 2.9 and 2.8—A Resolution," *Biochemistry* 20:2361-2370, the American Chemical Society, United States (1981).

Dreher, M., et al., "Colony assays for antibody fragments expressed in bacteria," *J. Immunol. Methods* 139:197-205, Elsevier Science Publishers B.V., Netherlands (1991).

Eppstein, D., et al., "Biological activity of liposome-encapsulated murine interferon γ is mediated by a cell membrane receptor," *Proc. Natl. Acad. Sci. USA* 82:3688-3692, National Academy of Sciences, United States (1985).

Gruber, M., et al., "Efficient Tumor Cell Lysis Mediatd by a Bispecific Single Chain Antibody Expressed in *Escherichia coli," J. Immunol.* 152:5368-5374, The American Association of Immunologists, United States (1994).

Harlow, E. and Lane, D., "Chapter 14: Immunoassays," in *Antibodies: A Laboratory Manual*, pp. 553-612, Cold Spring Harbor Laboratory, Cold Spring Harbor, NY (1988).

(56) References Cited

OTHER PUBLICATIONS

Harris, W., "Therapeutic Monoclonals," *Biochem. Soc. Transactions* 23:1035-1038, Industrial Biochemistry and Biotechnology Group Colloquium, University of Manchester, United Kingdom (1995).
Hawkins, R., et al., "Selection of Phage Antibodies by Binding Affinity Mimicking Affinity Maturation," *J. Mol. Biol.* 226:889-896, Academic Press Limited, United States (1992).
Hermentin, P. and Seiler, F., "Investigations with Monoclonal Antibody Drug (Anthracycline) Conjugates," *Behring Inst. Mitt.* 82:197-215, Die Medizinische Verlagsgesellschaft mbH, W. Germany (1988).
Hoogenboom, H. and Winter, G., "By-passing Immunisation: Human Antibodies from Synthetc Reperoires of Germline $V_H$ Gene Segments Rearranged in Vitro," *J. Mol. Biol.* 227:381-388, Academic Press Limited, United States (1992).
Humphreys, D., et al., "Formation of dimeric Fabs in *Escherichia coli*: effect of hinge size and isotype, presence of interchain disulphide bond, Fab' expression levels, tail piece sequences and growth conditions," *J. Immunol. Methods* 209:193-202, Elsevier Science B.V., Netherlands (1997).
Hurle, M. and Gross, M., "Protein engineering techniques for antibody humanization," *Curr. Opin. Biotech.* 5:428-433, Current Biology Ltd., United States (1994).
Hwang, K., et al., "Hepatic uptake and degradation of unilamellar sphingomyelin/cholesterol liposomes: A kinetic study," *Proc. Natl. Acad. Sci. USA* 77:4030-4034, National Academy of Sciences, United States (1980).
Jackson, J., et al., "In Vitro Antibody Maturation," *J. Immunol.* 154:3310-3319, The American Association of Immunologists, United States (1995).
Jones, P., et al., "Replacing the complementarity-determining regions in a human antibody with those from a mouse," *Nature* 321:522-525, Nature Publishing Group, United Kingdom (1986).
Kingsman, A., et al., "Replication In *Saccharomyces cerevisiae* of Plasmid pBR313 Carrying DNA From the Yeast *trpl* Region," *Gene* 7:141-152, Elsevier/North-Holland Biomedical Press, Netherlands (1979).
Kostelny, S., et al., "Formation of a Bispecific Antibody by the Use of Leucine Zippers," *J. Immunol.* 148:1547-1553, The American Association of Immunologists, United States (1992).
Lee, H., et al., "Generation of characterization of a novel single-gene-encoded single-chain immunoglobulin molecular with antigen binding activity and effector functions," *Mol. Immunol.* 36:61-71, Elsevier Science Ltd., Netherlands (1999).
Maeda, H., et al., "Construction of reshaped human antibodies with HIV-neutralizing activity," *Hum. Antibod. Hybridomas* 2:124-134, Butterworth-Heinemann, United Kingdom (1991).
Marks, J., et al., "By-passing Immunization: Human Antibodies from V-gene Libraries Displayed on Phage," *J. Mol. Biol.* 222:581-597, Academic Press Limited, United Kingdom (1991).
Marks, J., et al., "By-Passing Immunization: Building High Affinity Human Antibodies By Chain Shuffling," *Bio/Technology* 10:779-783, Nature Publishing Co., United States (1992).
Milstein, C., et al., "Hybrid hybridomas and their use in immunohistochemistry," *Nature* 305:537-539, Nature Publishing Group, United Kingdom (1983).
Morimoto, K., et al., "Single-step purification of $F(ab')_2$ fragments of mouse monoclonal antibodies (immunoglobulins G1) by hydrophobic interaction high performance liquid chromatography using TSKgel Phenyl-5PW," *J. Biochem. Biophys. Methods* 24:107-117, Elsevier Science Publishers B.V., Netherlands (1993).
Morrison, S., et al., "Chimeric human antibody molecules: Mouse antigen-binding domains with human constant region domains," *Proc. Natl. Acad. Sci. USA* 81:6851-6855, National Academy of Sciences, United States (1984).
Nohaile, M., et al., "Altering dimerization specificity by changes in surface electrostatics," *Proc. Natl. Acad. Sci. U.S.A.* 98:3109-3114, United States National Academy of Sciences, United States (2001).
Novotny, J. and Haber, E., "Structural invariants of antigen binding: Comparison of immunoglobin $V_L$-$V_H$ and $V_L$-$V_L$ domain dimers," *Proc. Natl. Acad. Sci. USA* 82:4592-4596, National Academy of Sciences, United States (1985).
Presta, L., et al., "Humanization of an Antibody Directed Against IgE," *J. Immunol.* 151:2623-2632, The American Association of Immunologists, United States (1993).
Riechmann, L., et al., "Reshaping human antibodies for therapy," *Nature* 332:323-329, Nature Publishing Group, United States (1988).
Sal-Man, N., et al. "Arginine mutations within a transmembrance domain of Tar, an *Escherichia coli* aspartate receptor, can drive homodimer dissociation and heterodimer association in vivo," *Biochem. J.* 385:29-36, Portland Press, United Kingdom (2005).
Schier, R., et al., "Identification of function and structural amino-acid residues by parsimonious mutagenesis," *Gene* 169:147-155, Elsevier Science B.V., Netherlands (1996).
Shalaby, M., et al., "Development of Humanized Bispecific Antibodies Reactive with Cytotoxic Lymphocytes and Tumor Cells Overexpressing the *HER2* Protooncogene," *J. Exp. Med.*175:217-225, The Rockefeller Univeristy Press, United States (1992).
Sheets, M., et al., "Efficient construction of a large nonimmune phage antibody library: The production of high-affinity human single-chain antibodies to protein antigens," *Proc. Natl. Acad. Sci. USA* 95:6157-6162, National Academy of Sciences, United States (1998).
Sims, M., et al., "A Humanized CD18 Antibody Can Block Function without Cell Destruction," *J. Immunol.*151:2296-2308, The American Association of Immunologists, United States (1993).
Stinchcomb, D., et al., "Isolation and characterisation of a yeast chromosomal replicator," *Nature* 282:39-43, Nature Publishing Group, United Kingdom (1979).
Suresh, M., et al., "Bispecific Monoclonal Antibodies from Hybrid Hybridomas," *Methods Enzymol.* 121:210-228, Academic Press Inc., United Kingdom (1986).
Traunecker, A., et al., "Bispecific single chain molecules (Janusins) target cytotoxic lymphocytes on HIV infected cells," *EMBO J.*10:3655-3659, Oxford University Press, United Kingdom (1991).
Tutt, A., et al., "Trispecific $F(ab')_3$ Derivatives That Use Cooperative Signaling Via the TCR/CD3 Complex and CD2 to Activate and Redirect Resting Cytotoxic T Cells," *J. Immunol.* 147:60-69, The American Association of Immunologists, United States (1991).
Urlaub, G. and Chasin, L., "Isolation of Chinese hamster cell mutants deficient in dihydrofolate reductase activity," *Proc. Natl. Acad. Sci. USA* 77: 4216-4220, National Academy of Sciences, United States (1980).
Vaswani, S. and Hamilton, R., "Humanized antibodies as potential therapeutic drugs," *Ann. Allergy Asthma Immunol.* 81:105-119, American College of Allergy, Asthma, & Immunology, United States (1998).
Vaughan, T., et al., "Human Antibodies with Sub-nanomolar Affinities Isolated from a Large Non-immunized Phage Display Library," *Nat. Biotech.*14:309-314, Nature Publishing Co., United States (1996).
Verhoeyen, M., et al., "Reshaping Human Antibodies: Grafting an Antilysozyme Activity," *Science* 239:1534-1536, American Association for the Advancement of Science, United States (1988).
Ward, E., "Antibody Engineering Using *Escherichia coli* as Host," *Adv. Pharmacol.* 24:1-20, Academic Press, Inc., United Kingdom (1993).
Wu, C., et al., "Simultaneous targeting of multiple disease mediators by a dual-variable-domain immunoglobulin," *Nat. Biotech.* 25:1290-1297, Nature Publishing Co., United States (2007).
Yelton, D., et al., "Affinity Maturation of the BR96 Anti-Carcinoma Antibody by Codon-Based Mutagenesis," *J. Immunol.* 155:1994-2004, The American Association of Immunologists, United States (1995).
International Search Report with the Written Opinion of the International Searching Authority for International application No. PCT/US10/32625, mailed on Dec. 17, 2010, United States Patent and Trademark Office, United States, 12 pages.

* cited by examiner

Figure 4

Figure 9:
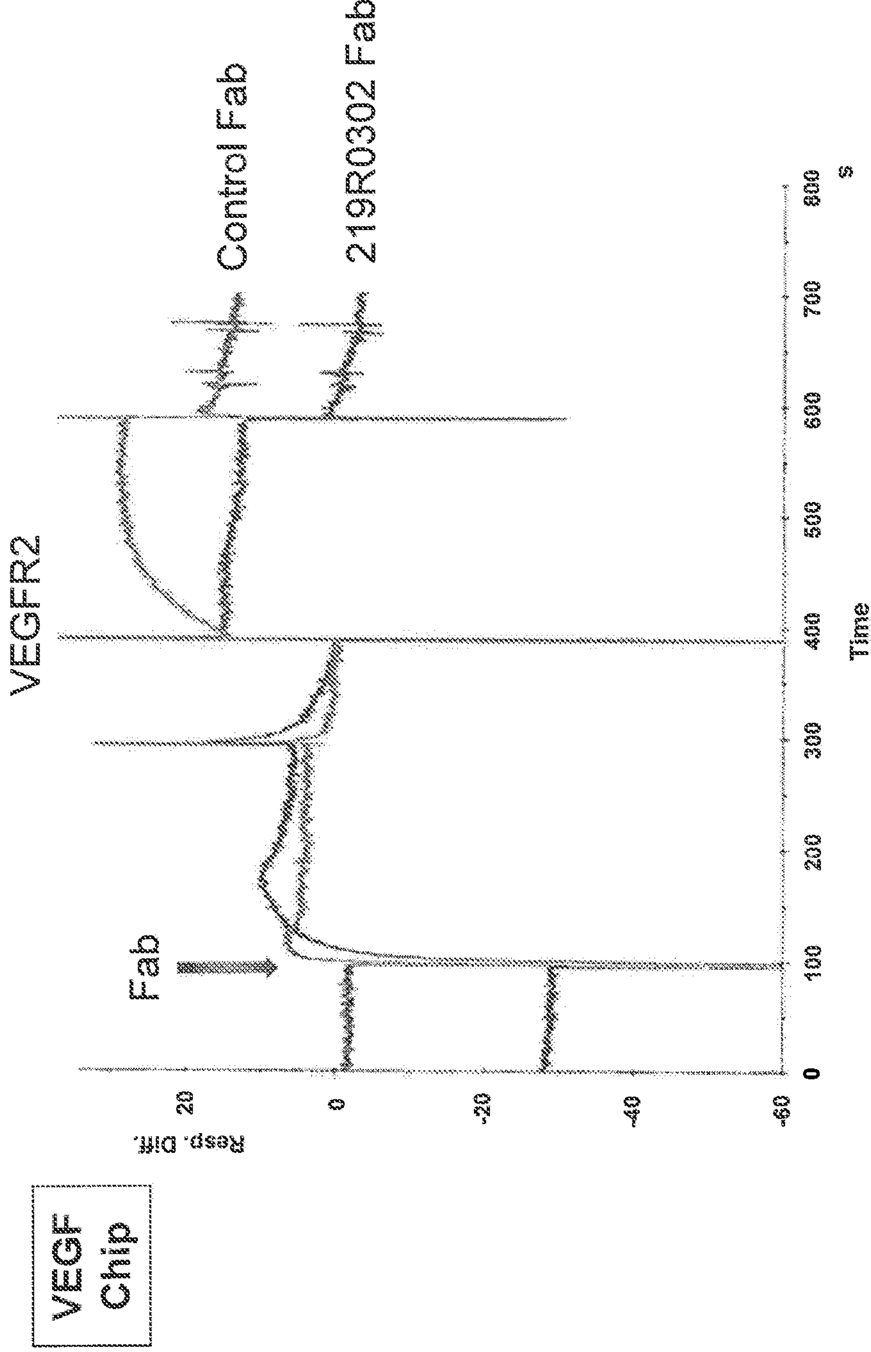

Figure 9: Anti-VEGF Fab (219R0302) blocks binding of VEGFR2 Fc to hVEGF biacore surface.

Figure 16:
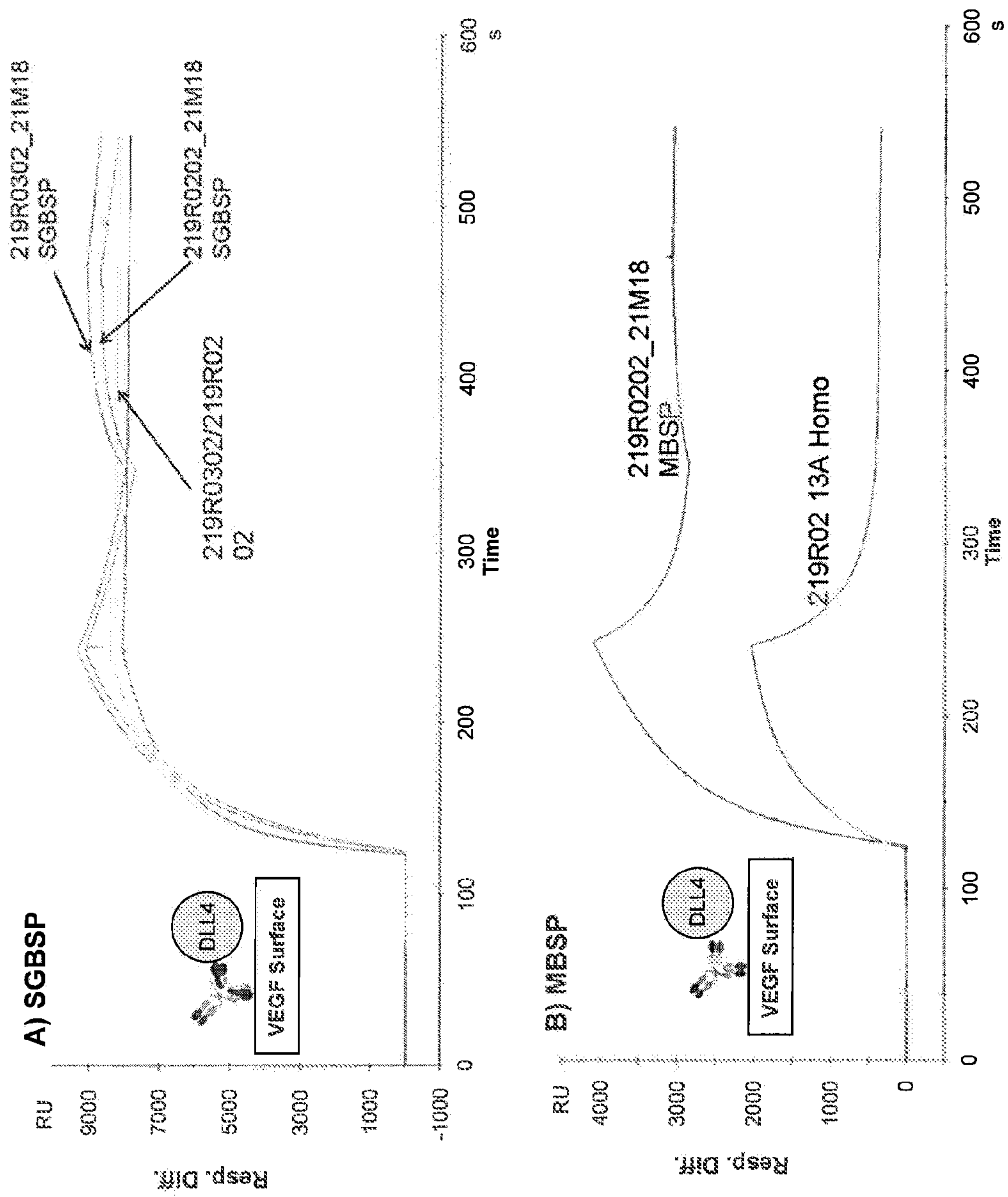

EVH_410 PE13 w various Bsp Abs
Mean Volume ± SEM, mm³
2000
1800
1600
1400
1200
1000
800
600
400
200
0
0
5
10
15
20
25
30
35
Day
PE13(P4) / LZ-1 15mg/kg
PE13(P4) / 219R0202 15mg/kg
PE13(P4) / 219R0302 15mg/kg
PE13(P4) / Avastin 15mg/kg Figure 16: Both SGBSPs and the MBSP bind both VEGF and DLL4 in a bispecific manner.

METHOD FOR MAKING HETEROMULTIMERIC MOLECULES

CROSS-REFERENCE TO RELATED APPLICATIONS

This application is a divisional of U.S. application Ser. No. 12/768,650, filed Apr. 27, 2010, which claims the priority benefit of U.S. Provisional Application No. 61/173,129, filed Apr. 27, 2009 and U.S. Provisional Application No. 61/177,412, filed May 12, 2009, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: 2293_0540003_SL.txt, Size: 71,363 bytes; and Date of Creation: Oct. 30, 2015) is herein incorporated by reference in its entirety.

BACKGROUND OF THE INVENTION

1. Field of the Invention

The present invention provides methods for making heteromultimeric molecules, such as bispecific antibodies, and compositions comprising said molecules. The methods include introducing substitutions in amino acids that are in contact at the interface between two polypeptides. Such substitutions include changes in amino acids that result in altered electrostatic and/or hydrophobic/hydrophilic interactions between the polypeptides that make up the heteromultimeric molecules. The substitutions result in multimeric molecules in which homomultimeric molecules are disfavored, and heteromultimeric molecules are preferentially formed.

2. Background Art

The hallmark of monoclonal antibodies is their ability to specifically bind to a particular antigen, which enables them to bind to their target in vivo but not antigen-negative sites. Once bound to a target, therapeutic monoclonal antibodies can deliver a toxic payload, act as agonists or antagonists of receptors, or as neutralizers of ligands. Monoclonal antibodies can also be modified to be more immunologically tolerated in various species. One such modification, that entails the replacement of amino acids in structural regions with amino acids found in humans, is humanization. Humanized antibodies can then be further modified. One such modification is arming the humanized antibody with additional cytotoxic mechanisms, be it radioisotopes, bacterial toxins, inflammatory cytokines, chemotherapeutics or prodrugs.

There is a growing number of approved cancer therapeutics that are efficacious either as a chimerized antibody (Rituximab) or humanized IgG1 (Herceptin and Campath-1H), as conjugate with chemotherapeutics (Mylotarg) or a radioisotope (Zevalin and Bexxar). In spite of this progress, the efficacy of monoclonal antibodies for cancer treatment is still limited, leaving great potential for further improvements. One class of antibody derivatives with the promise of enhanced potency for cancer treatment is bispecific antibodies.

Antibodies with a dual specificity in their binding arms usually do not occur in nature and, therefore, were developed through recombinant DNA or cell-fusion technology. Most bispecific antibodies are designed to recruit cytotoxic effector cells of the immune system effectively against pathogenic target cells. After more than 15 years of extensive research, many different types of bispecific antibodies have been developed but only a few have advanced to clinical trials.

Among the first bispecific antibodies were constructs designed to redirect T cells against cancer target cells. Target cells are killed when cytotoxic T lymphocytes (CTLs) are tethered to tumor cells and simultaneously triggered by one arm of the bispecific antibody that interact with the T-cell receptor (TCR)-CD3 complex. CTLs, which are considered to be the most potent killer cells of the immune system, cannot be engaged by monoclonal antibodies because they lack Fcγ-receptors.

Another type of bispecific antibody is those that simultaneously bind tumor cells and an activating Fcγ-receptor, for example, CD64/FcγRI on monocytes. Binding of this type of bispecific antibody to Fcγ-receptors can elicit effector cell activation, without being competed by simultaneously binding normal IgG.

One method for generating bispecific antibodies has been termed the "knobs-into-holes" strategy (see, e.g., WO 2006/028936). The mispairing of Ig heavy chains is reduced in this technology by mutating selected amino acids forming the interface of the CH3 domains in human IgG. At positions within the CH3 domain at which the two heavy chains interact directly, an amino acid with a small side chain (hole) is introduced into the sequence of one heavy chain and an amino acid with a large side chain (knob) into that of the other one. As a result, the protein interaction between knobs and holes has been described as leading to the formation of up to 90% of the correct bispecific human IgG by transfected mammalian host cells.

The present invention provides methods for preferentially forming heteromultimeric molecules by mutating selected amino acids that interact at the interface between two polypeptides by replacing an amino acid residue involved in hydrophilic interactions with a more hydrophobic amino acid residue and/or replacing an amino acid involved in a charge interaction with another amino acid.

BRIEF SUMMARY OF THE INVENTION

The present invention provides a method of preparing a heteromultimeric polypeptide comprising two human immunoglobulin CH3 domain-containing polypeptides, the method comprising substituting at least one amino acid within the CH3 domain of one of the polypeptides at a position corresponding to a position selected from the group consisting of positions 236, 245, 249, 278, 286, and 288 of human IgG2 with another amino acid, thereby promoting heteromultimer formation. In one embodiment, the invention provides a method of preparing a heteromultimeric polypeptide comprising two human immunoglobulin CH3 domain-containing polypeptides, the method comprising substituting at least one charged amino acid residue in the CH3 domain of each of the polypeptides with an amino acid of the opposite charge. In another embodiment, the pair of substituted amino acids form an ion pair in the heteromultimeric polypeptide.

In another embodiment, the invention provides a method of preparing a heteromultimeric polypeptide comprising two human immunoglobulin CH3 domain-containing polypeptides, the method comprising substituting at least one hydrophilic amino acid residue in the CH3 domain of one of the polypeptides with another amino acid. In one embodiment, the hydrophilic amino acid residue is substituted by a hydrophobic residue. In certain embodiments, the substitution causes replacement of an amino acid having a hydroxyl side chain is substituted with an amino acid that does not have a hydroxyl side chain. In a further embodiment, the method further comprises substituting at least one hydrophilic amino acid residue in the CH3 domain of one of the polypeptides with another amino acid at the interface of the two polypeptides in one of the polypeptides with another amino acid. In yet another embodiment, the substituted amino acid interacts with another amino acid at the interface of the two polypeptides. Representative amino acids that are predicted to interact at the interface include those listed in Table 1, or is an amino acid at a position corresponding to those listed in Table 1.

In one embodiment, the human immunoglobulin CH3 domain of both polypeptides is selected from the group consisting of IgG, IgA, and IgD CH3 domains. In a further embodiment, the immunoglobulin CH3 domain is an IgG2 CH3 domain.

In one embodiment, the first CH3-domain containing polypeptide comprises a first immunoglobulin heavy chain polypeptide that specifically binds to a first immunoglobulin light chain polypeptide, and the second CH3-domain containing polypeptide comprises a second immunoglobulin heavy chain polypeptide that specifically binds to a second immunoglobulin light chain polypeptide. In a further embodiment, the first immunoglobulin light chain polypeptide and the second immunoglobulin light chain polypeptide are identical in amino acid sequence.

In one embodiment, the method comprises substituting amino acids in one CH3 domain at positions corresponding to position 249 and position 288 of human IgG2. In a further embodiment, the amino acids at positions 249 and 288 are replaced with glutamate. In another embodiment, the amino acids at positions 249 and 288 are replaced with aspartate. In one embodiment, the method comprises substituting amino acids in one CH3 domain at positions corresponding to position 249, position 286, and position 288 of human IgG2. In a further embodiment, the amino acids at positions 249 and 288 are replaced with glutamate, and the amino acid at position 286 is replaced with phenylalanine. In one embodiment, the method further comprises substituting amino acids in the second CH3 domain at positions corresponding to position 236 and position 278 of human IgG2. In another embodiment, the amino acid at position 236 is replaced with a lysine, and the amino acid at position 278 is replaced with a lysine.

In one embodiment, the method comprises substituting amino acids in one CH3 domain at positions corresponding to position 236 and position 278 of human IgG2. In another embodiment, the amino acid at position 236 is replaced with a lysine, and the amino acid at position 278 is replaced with a lysine.

In one embodiment, the method comprises preparing a heteromultimeric polypeptide that is monovalent. In another embodiment, the method comprises preparing a monovalent heteromultimeric polypeptide comprising a detectable label or epitope.

In one embodiment, the method comprises preparing a heteromultimeric polypeptide that is bivalent. In another embodiment, the first polypeptide binds a target molecule through its immunoglobulin antigen binding domain, and the second polypeptide is an immunoadhesin. In one embodiment, the first and second polypeptides preferentially assemble with each other as heterodimers, relative to assembly of homodimers. In another embodiment, the first and second polypeptides assemble to form a bispecific antibody.

In one embodiment, the method comprises preparing a heteromultimeric molecule wherein the first CH3-domain containing polypeptide comprises a first immunoglobulin heavy chain polypeptide that specifically binds to a first immunoglobulin light chain polypeptide, and the second CH3-domain containing polypeptide comprises a second immunoglobulin heavy chain polypeptide that specifically binds to a second immunoglobulin light chain polypeptide. In another embodiment, the first immunoglobulin light chain polypeptide and the second immunoglobulin light chain polypeptide are identical in amino acid sequence. In another embodiment, the immunoglobulin light chain polypeptide is linked to the immunoglobulin heavy chain polypeptide.

In one embodiment, the method comprises preparing a bispecific antibody that specifically binds two different antigens. In another embodiment, the bispecific antibody binds two different epitopes on the same antigen.

In one embodiment, the method comprises preparing a heteromultimeric polypeptide that specifically binds an antigen selected from the group consisting of: DLL4, VEGF, VEGFR2, Notch1, Notch2, Notch3, Notch4, Notch(pan), JAG1, JAG2, DLL(pan), JAG(pan), EGFR, ERBB2, ERBB3, ERBB(pan), c-Met, IGF-1R, PDGFR, Patched, Hedgehog family polypeptides, Hedgehog(pan), WNT family polypeptides, WNT(pan), FZD1, FZD2, FZD3, FZD4, FZD5, FZD6, FZD7, FZD8, FZD9, FZD10, FZD(pan), LRP5, LRP6, CD20, IL-6, TNFalpha, IL-23, IL-17, CD80, CD86, CD3, CEA, Muc16, PSMA, PSCA, CD44, c-Kit, DDR1, DDR2, RSPO1, RSPO2, RSPO3, RSPO4, RSPO(pan), BMP family polypeptides, BMP (pan), BMPR1a, BMPR1b, and a combination thereof.

In one embodiment, the method comprises preparing a heteromultimeric polypeptide comprises the VEGF binding sequence comprising heavy chain sequence of SEQ ID NO:11 and the light chain sequence of SEQ ID NO:13 or SEQ ID NO:15. In another embodiment, the heteromultimeric polypeptide comprises the VEGF binding sequence comprising heavy chain sequence of SEQ ID NO:11 and the light chain sequence of SEQ ID NO:13. In another embodiment, the heteromultimeric polypeptide comprises the VEGF binding sequence comprising heavy chain sequence of SEQ ID NO:11 and the light chain sequence of SEQ ID NO:15. In yet another embodiment, the heteromultimeric polypeptide comprises the DLL4 binding sequence comprising SEQ ID NO:19.

In one embodiment, the method comprises preparing a heteromultimeric polypeptide is a bispecific antibody that binds DLL4 and VEGF. In one embodiment, the heteromultimeric polypeptide comprises light chain polypeptides that are identical in sequence. In another embodiment, the light chain polypeptides are linked to the heavy chain polypeptides. In another embodiment, the bispecific antibody comprises the VEGF binding sequence comprising heavy chain sequence of SEQ ID NO:11 and the light chain sequence of SEQ ID NO:13 or SEQ ID NO:15; and the DLL4 binding sequence comprising SEQ ID NO:19. In another embodiment, the heteromultimeric polypeptide comprises the VEGF binding sequence comprising heavy chain sequence of SEQ ID NO:11 and the light chain sequence of SEQ ID NO:13; and the DLL4 binding sequence comprising SEQ ID NO:19. In a further embodiment, the heteromultimeric polypeptide comprises the VEGF binding sequence comprising heavy chain sequence of SEQ ID NO:11 and the light chain sequence of SEQ ID NO:15; and the DLL4 binding sequence comprising SEQ ID NO:19.

The invention also provides an antibody that specifically binds VEGF, wherein the antibody comprises: (a) a heavy chain CDR1 comprising GYTFTNYWMH (SEQ ID NO:20), a heavy chain CDR2 comprising SINPSNGGTSYNEKFKR (SEQ ID NO:21), and a heavy chain CDR3 comprising HYYDNSYAMDY (SEQ ID NO:22); and/or (b) a light chain CDR1 comprising QASQDISNYVN (SEQ ID NO:23), a light chain CDR2 comprising DASNLQT (SEQ ID NO:24), and a light chain CDR3 comprising QQYDDLPP (SEQ ID NO:25). The invention also provides an antibody that specifically binds VEGF, wherein the antibody comprises: (a) a heavy chain CDR1 comprising GYTFTNYWMH (SEQ ID NO:20), a heavy chain CDR2 comprising SINPSNGGTSYNEKFKR (SEQ ID NO:21), and a heavy chain CDR3 comprising HYYDNSYAMDY (SEQ ID NO:22); and/or (b) a light chain CDR1 comprising RASQGINNHLAW (SEQ ID NO:26), a light chain CDR2 comprising AASNLHS (SEQ ID NO:27), and a light chain CDR3 comprising QQYDNLPL (SEQ ID NO:28).

In one embodiment, the antibody is an antagonist of human VEGF. In another embodiment, the anti-VEGF antibody is an antibody fragment. In one embodiment, the antibody is a monoclonal antibody or a humanized antibody.

In one embodiment, the anti-VEGF antibody inhibits tumor growth.

In one embodiment, the anti-VEGF antibody binds to human VEGF with a $K_D$ of about 100 nM or less.

The invention also provides a heteromultimeric polypeptide prepared by the methods described herein. In one embodiment, the heteromultimeric polypeptide has the characteristics of a heteromultimeric polypeptide prepared by the methods described herein.

In one embodiment, the heteromultimeric polypeptide is monovalent.

In another embodiment, the heteromultimeric polypeptide is bivalent. In a further embodiment, the heteromultimeric polypeptide is a bispecific antibody.

The invention also provides a polypeptide comprising an immunoglobulin CH3 domain, wherein the CH3 domain contains a glutamate at positions corresponding to positions 249 and 288 of human IgG2.

The invention also provides a polypeptide comprising an immunoglobulin CH3 domain, wherein the CH3 domain contains a glutamate at positions corresponding to positions 249 and 288 of human IgG2 and a phenylalanine at a position corresponding to position 286 of human IgG2.

The invention also provides a polypeptide comprising an immunoglobulin CH3 domain, wherein the CH3 domain contains a lysine at positions corresponding to positions 236 and 278 of human IgG2.

In one embodiment, the polypeptide immunoglobulin CH3 domain is an IgG CH3 domain.

In one embodiment, the heteromultimeric polypeptide comprises both (i) a polypeptide comprising an immunoglobulin CH3 domain, wherein the CH3 domain contains a glutamate at positions corresponding to positions 249 and 288 of human IgG2, or a polypeptide comprising an immunoglobulin CH3 domain, wherein the CH3 domain contains a glutamate at positions corresponding to positions 249 and 288 of human IgG2 and a phenylalanine at a position corresponding to position 286 of human IgG2, and (ii) a polypeptide comprising an immunoglobulin CH3 domain, wherein the CH3 domain contains a lysine at positions corresponding to positions 236 and 278 of human IgG2.

In one embodiment, the first and/or second CH3-domain containing polypeptide(s) further comprise an immunoglobulin CH2 domain.

In one embodiment, the polypeptide comprises the amino acid sequence of SEQ ID NO:1, SEQ ID NO:4, or SEQ ID NO:5.

In one embodiment, the polypeptide comprises the amino acid sequence of SEQ ID NO:2, SEQ ID NO:6, or SEQ ID NO:7.

In one embodiment, the polypeptide comprises the amino acid sequence of SEQ ID NO:3, SEQ ID NO:8, or SEQ ID NO:9.

In one embodiment, the heteromultimeric polypeptide comprises both a first amino acid sequence selected from the group consisting of SEQ ID NO:1, SEQ ID NO:2, SEQ ID NO:4, SEQ ID NO:5, SEQ ID NO:6, and SEQ ID NO:7; and a second amino acid sequence selected from the group consisting of SEQ ID NO:3, SEQ ID NO:8, and SEQ ID NO:9.

The invention further provides a heteromultimeric polypeptide comprising a polypeptide selected from SEQ ID NOs:1-9. In one embodiment, the heteromultimeric polypeptide is a heterodimer. In a further embodiment, the heteromultimeric polypeptide is a bispecific antibody. In another embodiment, the heteromultimeric polypeptide is a monovalent antibody.

In one embodiment, the heteromultimeric polypeptide specifically binds an antigen selected from the group consisting of: DLL4, VEGF, VEGFR2, Notch1, Notch2, Notch3, Notch4, Notch(pan), JAG1, JAG2, DLL(pan), JAG(pan), EGFR, ERBB2, ERBB3, ERBB(pan), c-Met, IGF-1R, PDGFR, Patched, Hedgehog family polypeptides, Hedgehog (pan), WNT family polypeptides, WNT(pan), FZD1, FZD2, FZD3, FZD4, FZD5, FZD6, FZD7, FZD8, FZD9, FZD10, FZD(pan), LRP5, LRP6, CD20, IL-6, TNFalpha, IL-23, IL-17, CD80, CD86, CD3, CEA, Muc16, PSMA, PSCA, CD44, c-Kit, DDR1, DDR2, RSPO1, RSPO2, RSPO3, RSPO4, RSPO(pan), BMP family polypeptides, BMP(pan), BMPR1a, BMPR1b, and a combination thereof.

In one embodiment, the heteromultimeric polypeptide comprises the VEGF binding sequence comprising heavy chain sequence of SEQ ID NO:11 and the light chain sequence of SEQ ID NO:13 or SEQ ID NO:15. In another embodiment, the heteromultimeric polypeptide comprises the VEGF binding sequence comprising heavy chain sequence of SEQ ID NO:11 and the light chain sequence of SEQ ID NO:13. In one embodiment, the heteromultimeric polypeptide comprises the VH sequence of SEQ ID NO:10 and the VL sequence of SEQ ID NOs: 31 or 32. In another embodiment, the heteromultimeric polypeptide comprises the VEGF binding sequence comprising heavy chain sequence of SEQ ID NO:11 and the light chain sequence of SEQ ID NO:15. In yet another embodiment, the heteromultimeric polypeptide comprises the DLL4 binding sequence comprising SEQ ID NO:19.

In one embodiment, the heteromultimeric polypeptide is a bispecific antibody that binds DLL4 and VEGF. In one embodiment, the VEGF binding sequence comprises SEQ ID NO:17 or SEQ ID NO:18. In one embodiment, the DLL4 binding sequence comprises SEQ ID NO:19. In another embodiment, the bispecific antibody comprises the VEGF binding sequence comprising heavy chain sequence of SEQ ID NO:11 and the light chain sequence of SEQ ID NO:13 or SEQ ID NO:15; and the DLL4 binding sequence comprising SEQ ID NO:19. In another embodiment, the heteromultimeric polypeptide comprises the VEGF binding sequence comprising heavy chain sequence of SEQ ID NO:11 and the light chain sequence of SEQ ID NO:13; and the DLL4 binding sequence comprising SEQ ID NO:19. In a further embodiment, the heteromultimeric polypeptide comprises the VEGF binding sequence comprising heavy chain sequence of SEQ ID NO:11 and the light chain sequence of SEQ ID NO:15; and the DLL4 binding sequence comprising SEQ ID NO:19.

In one embodiment, the heteromultimeric polypeptide comprises light chain polypeptides are identical in amino acid sequence. In another embodiment, heteromultimeric polypeptide comprises light chain polypeptides that are linked to the heavy chain polypeptides.

In one embodiment, the heteromultimeric polypeptide comprises substituting amino acids in one CH3 domain at positions corresponding to position 249 and position 288 of human IgG2. In one embodiment, the heteromultimeric polypeptide the amino acids at positions 249 and 288 are replaced with glutamate. In another embodiment, the amino acids at positions 249 and 288 are replaced with aspartate.

In one embodiment, the heteromultimeric polypeptide comprises substituting amino acids in the second CH3 domain at positions corresponding to position 236 and position 278 of human IgG2. In one embodiment, the heteromultimeric polypeptide the amino acid at position 236 is replaced with a lysine, and the amino acid at position 278 is replaced with a lysine. In one embodiment, the heteromultimeric polypeptide comprises substituting amino acids in one CH3 domain at positions corresponding to position 236 and position 278 of human IgG2.

The invention also provides an isolated polypeptide comprising an amino acid sequence selected from the group consisting of SEQ ID NOs: 10, 31, and 32. In one embodiment, the isolated polypeptide is an antibody.

In one embodiment, the first and/or second CH3-domain containing polypeptide(s) further comprise a single chain Fv.

In one embodiment, the heteromultimeric polypeptide further comprises a cytotoxin or a radioisotope.

The invention also provides a polynucleotide encoding the polypeptides or antibodies of the invention. The invention also provides polynucleotides that hybridize under conditions of high stringency to the polynucleotides encoding the polypeptides or antibodies of the invention.

The invention also provides a host cell comprising a polynucleotide of the invention.

The invention also provides a method of making a heteromultimeric polypeptide comprising culturing the host cell under conditions that result in expression of the polypeptide.

The invention also provides for a pharmaceutical composition comprising the heteromultimeric polypeptide of the invention and a pharmaceutically acceptable carrier.

The invention also provides a method of treating a disorder comprising administering the heteromultimeric polypeptide or a composition of the invention to a patient in need thereof. In one embodiment, the disorder is cancer. In another embodiment, the method further comprises administering a second therapeutic compound. In one embodiment, the second therapeutic compound is used to treat a side effect caused by administration of the heteromultimeric polypeptide in the patient. In another embodiment, the second therapeutic compound is an anti-cancer agent. In yet another embodiment, the heteromultimeric polypeptide and the second therapeutic compound are administered simultaneously or sequentially.

BRIEF DESCRIPTIONS OF THE DRAWINGS

FIG. 1: The structure of antibody CH2 and CH3 domains. The structure is shown in ribbon view using the Pymol software program (DeLano Scientific LLC, California USA) of the antibody fc domain structure deposited in structure deposited in PDB (file 1FC1) (Deisenhofer .J. (1981) *Biochemistry,* 20, 2361-2370). The CH2 and CH3 domains of each chain in the dimeric structure are shown. The dimerization of the Fc fragment is mediated through interactions between CH3 domains.

Figure 2:
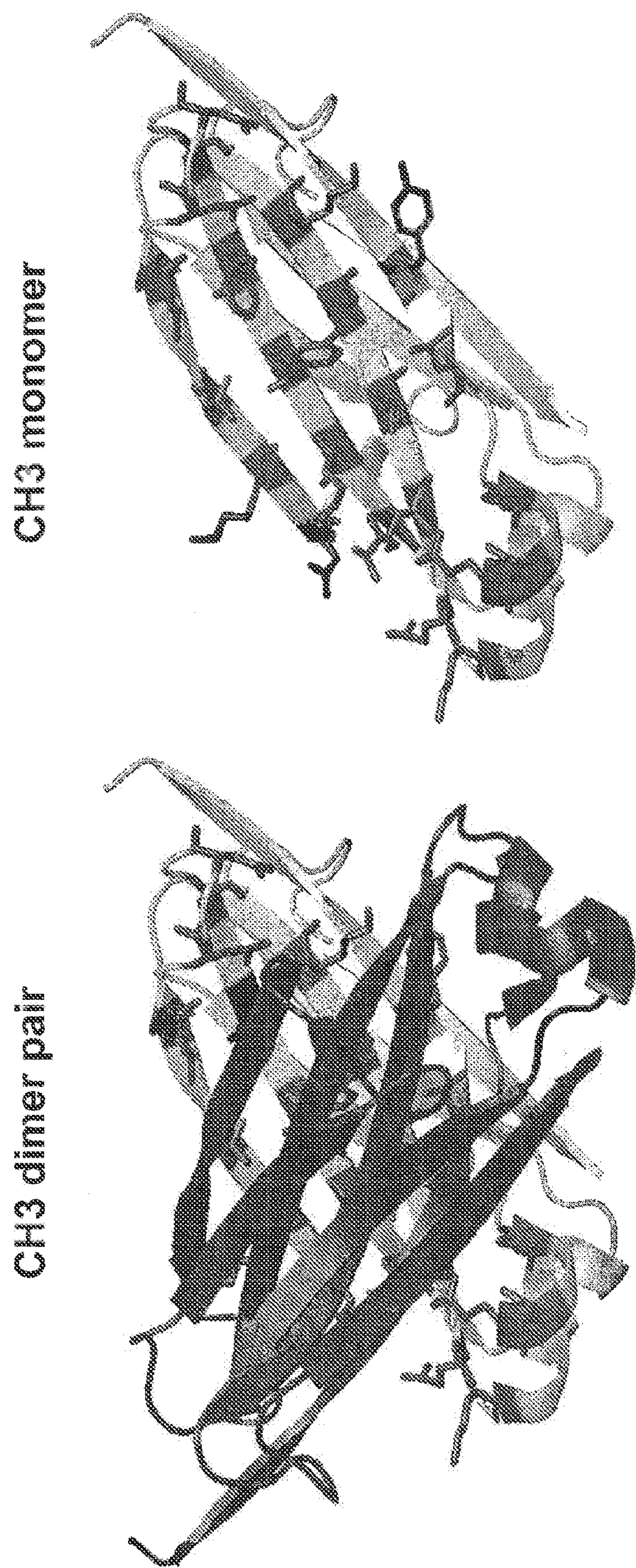

FIG. 2: The CH3 dimer interface. Shown is a ribbon structure view of the CH3 domain. On the left is an image of the dimer of two CH3 domains. On the right is an image of a single CH3 domain with depiction of the side chains of amino acids with potential to participate in inter-chain interactions.

Figure 3:
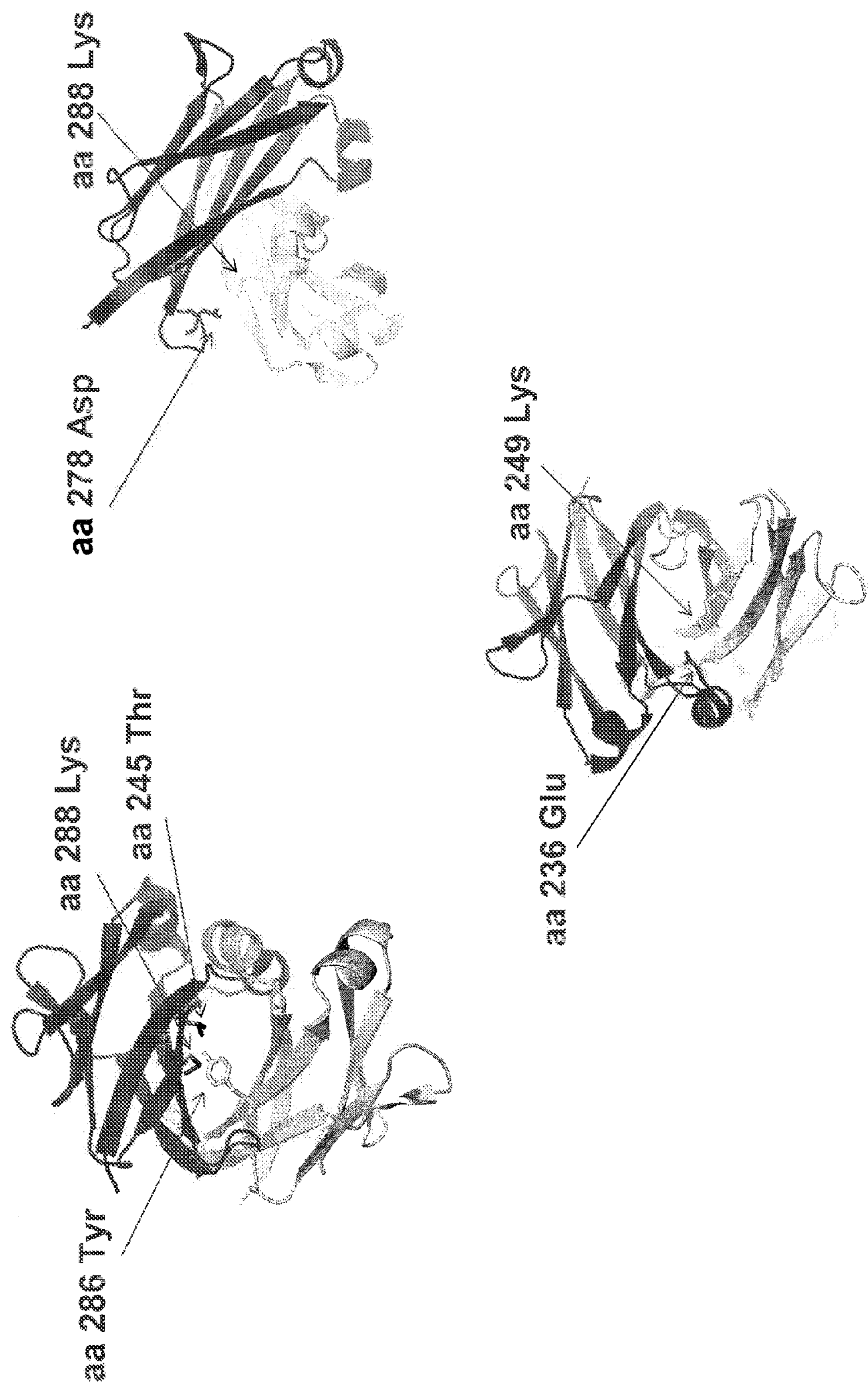

FIG. 3: Select amino acids are involved in inter-chain interactions. Shown are three separate views of dimerized CH3 domain chosen to best view particular amino acid residues. The structure is shown in ribbon view using the Pymol software program (DeLano Scientific LLC, California USA). Each view highlights selected amino acids that are postulated to contribute to inter-chain pairing. Individual amino acids are highlighted by depiction of the side chains and by notation of amino acid and position. The numbering scheme is relative to human IgG2 constant region.

Figure 4:
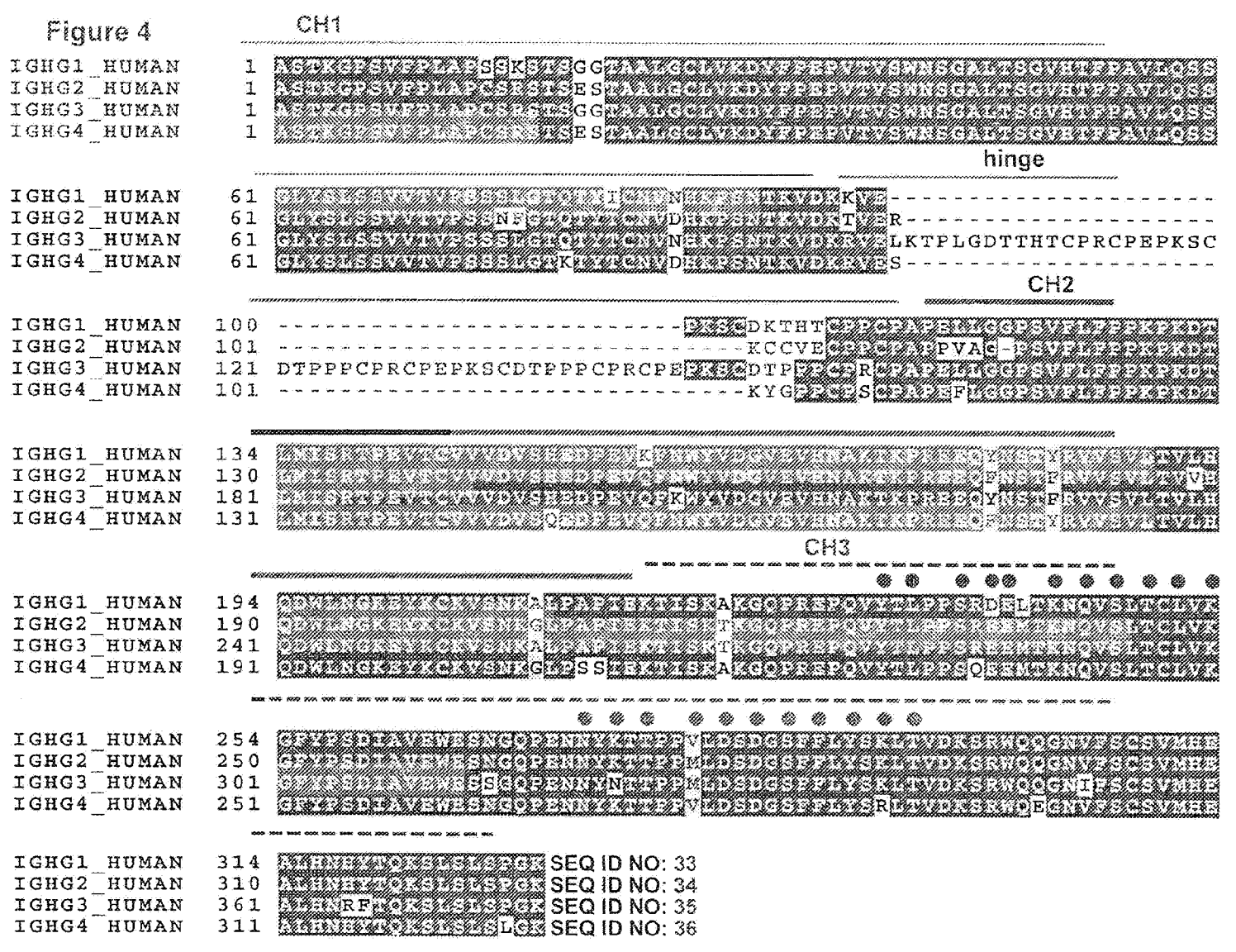

FIG. 4: The alignment of human IgG isotypes. Shown is an alignment of the constant region of human IgG isotypes IgG1 (SEQ ID NO: 33), IgG2 (SEQ ID NO: 34), IgG3 (SEQ ID NO: 35), and IgG4 (SEQ ID NO: 36). The CH3 domain is indicated by a bold dotted line. Individual amino acids that were highlighted in FIG. 2 and FIG. 3 and are postulated to play roles in inter-chain interactions are denoted by filled circles.

Figure 5:
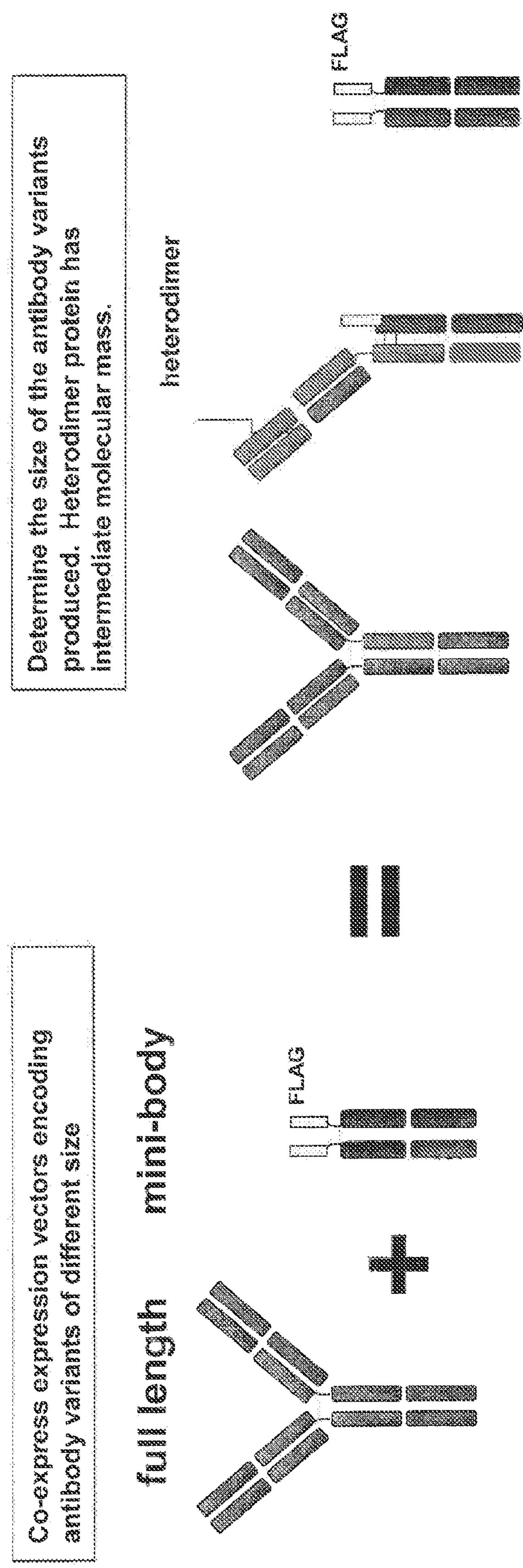

FIG. 5: An assay format for assessing homodimerization and heterodimerization. In order to determine the relative propensity of an Fc variant to homodimerize or heterodimerize with another Fc variant we generated a “mini-body” expression construct encoding the linker region and CH2-CH3 domains (amino acids 103-326 of the human IgG2 constant region) of IgG2 linked to an N terminal signal sequence and FLAG epitope. This construct, when transfected cells directs the expression of a secreted dimeric Fc domain (here termed “minibody”). As revealed by western blot analysis, the size of the minibody is substantially smaller than the size of an intact antibody produced by transfecting cells with expression vectors encoding heavy and light chains. Heterodimer formation can be assessed by transfecting a cell with vectors encoding both the intact antibody and the minibody Fc domain construct. Heterodimer formation will result in an intermediate size molecule containing one chain of minibody and one full length heavy chain complexed with light chain.

Figure 6:
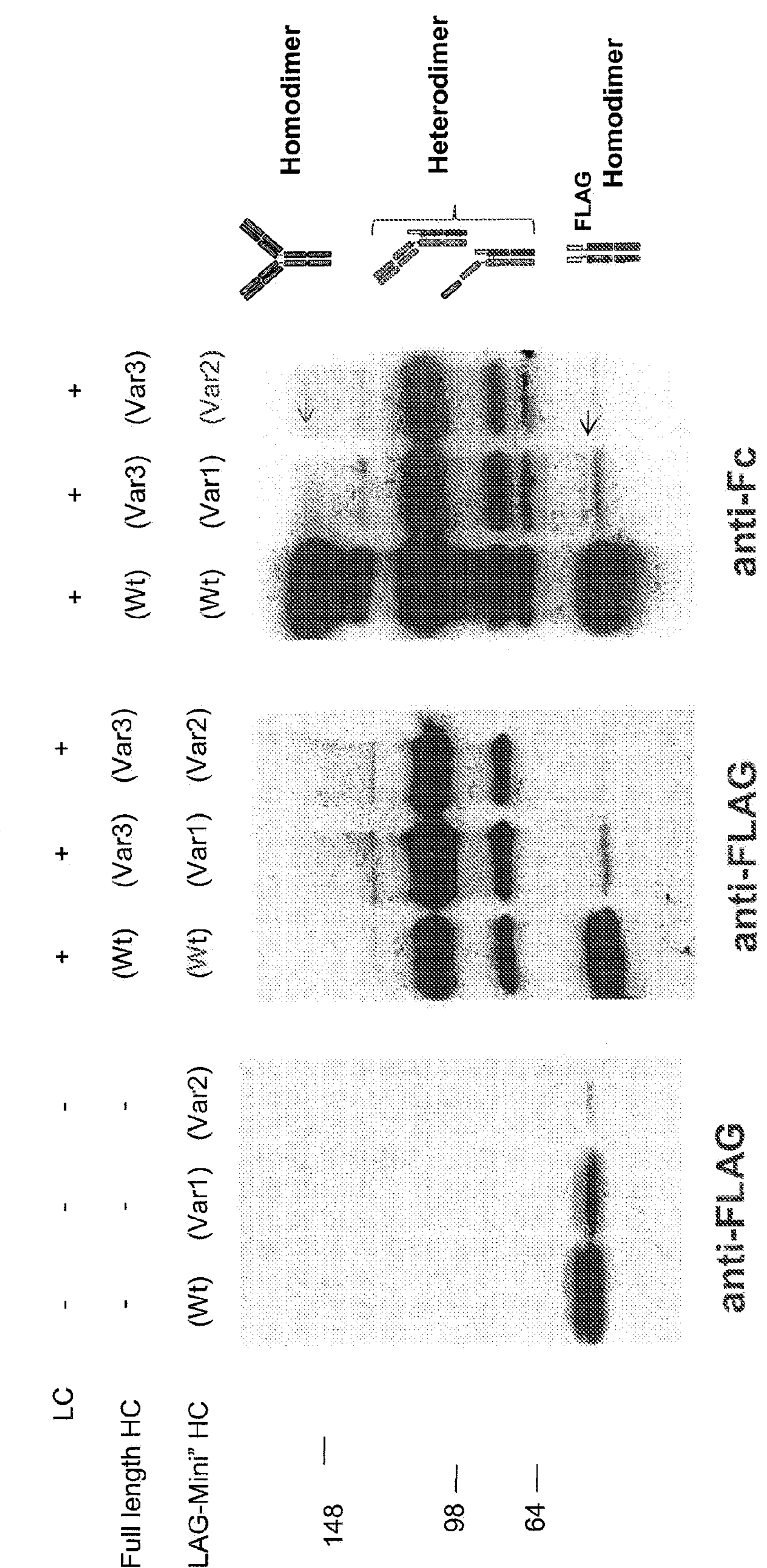

FIG. 6: Antibody variants that efficiently form heterodimeric Fc domains. Expression vector plasmids were generated that encode FLAG tagged minibody with wild type human IgG2 CH2 and CH3 domains (WT), and variants (Var1, also referred to as 13B, and Var2), a full length heavy chains with wild type human IgG2 CH2 and CH3 domains (WT), or a variant (Var3/13A), and a full length light chain (L2). Var1 contains amino acid 249 Lys to Glu substitution and amino acid 288 Lys to Glu substitution within the CH3 domain. Antibody Var2 contains substitutions of amino acid 249 Lys to Glu substitution, amino acid 286 Tyr to Phe, and amino acid 288 Lys to Glu within the CH3 domain. Antibody Var3 (also referred to as 13A) contains substitutions of amino acid 236 Glu to Ls and amino acid 278 Asp to Lys. HEK293 cells were transiently transfected with combinations of expression vectors as indicated. Non-reducing Western blot analysis was conducted with an anti-FLAG antibody to reveal the size of the secreted antibody products. Wild type human IgG2 readily exhibits homodimerization, as shown in the right panel where expressed Flag tagged “minibody” containing wild type human CH2-CH3 domain is readily detected. Antibody Var1 (13B) has greatly reduced ability to homodimerize. Antibody Var2 exhibits little to no ability to homodimerize. In the middle panel and left panel minibody variants are co-expressed with full length heavy chain variants, and heterodimer antibody forms are produced. Co-expression of wild-type full length heavy chain and wild type minibody results in production of both homodimer (as clearly demonstrated by the anti-FLAG western blot in the middle panel and by the intermediate mass bands observed in the anti-Fc Western blot in the right panel). These data show that coexpression of Var1 (13B) and Var3 (13A) results in preferential homodimerization, and that co-expression of Var2 and Var3 results in almost exclusive formation of heterodimer.

Figure 7:
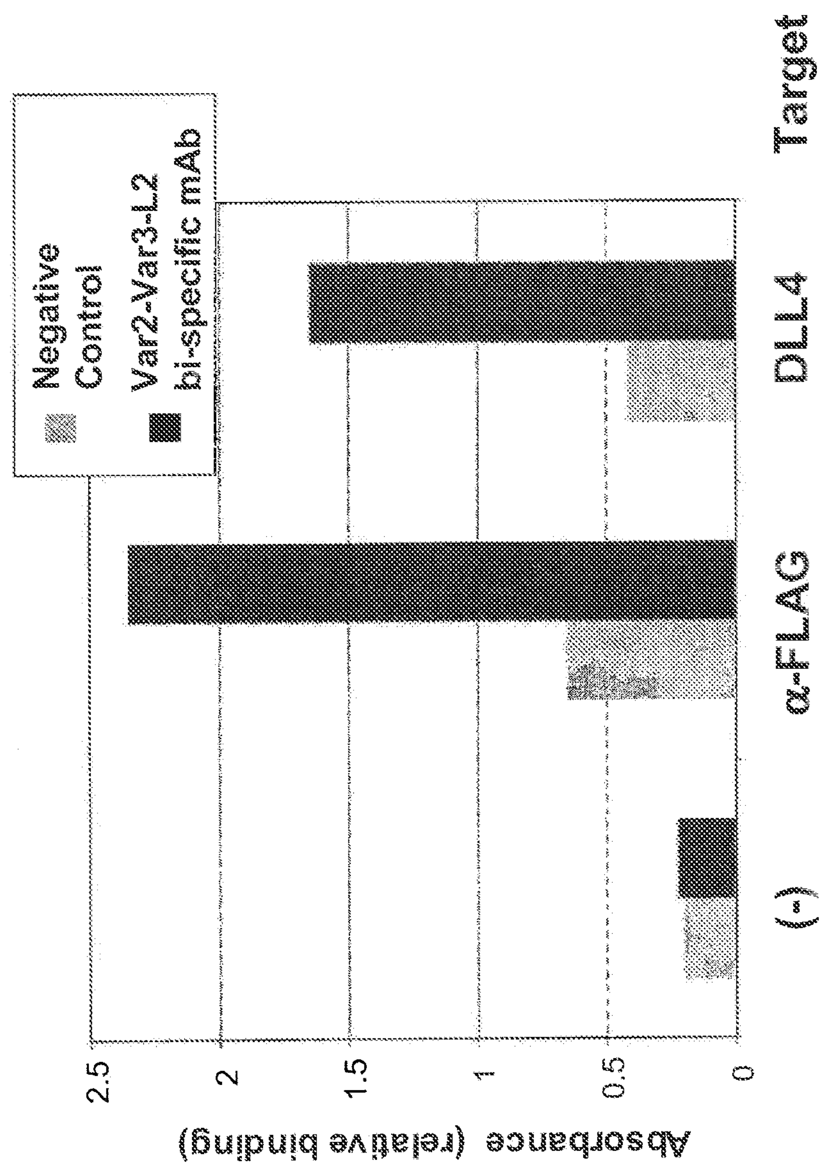

FIG. 7: The binding of a bispecific antibody binds to two targets. Enyzme-linked immunosorbent assay (ELISA) was conducted to examine the ability of bispecific antibody variant (Var2-Var3) to bind to antigens. ELISA plates were coated with either no antigen (–), anti-FLAG antibody (0.05 mg/ml, clone M2 from SIGMA), or recombinant human DLL4 (0.1 mg/ml) (amino acids 27-519 with a carboxy-terminal 8×His tag). Coated plates were then incubated with control cell culture medium (negative control) or conditioned medium from cells transfected with expression vectors encoding Var2, Var3, and light chain L2 as indicated. The results show that the bispecific antibody variant produced by co-expression of Var2 and Var3 heavy chains and L2 light chain is able to bind to DLL4, the antibody recognized by the parental wild-type antibody used to generate Var3, and also to bind the anti-FLAG antibody due to the FLAG epitope tag presented by the Var2 heavy chain variant arm.

Figure 8:
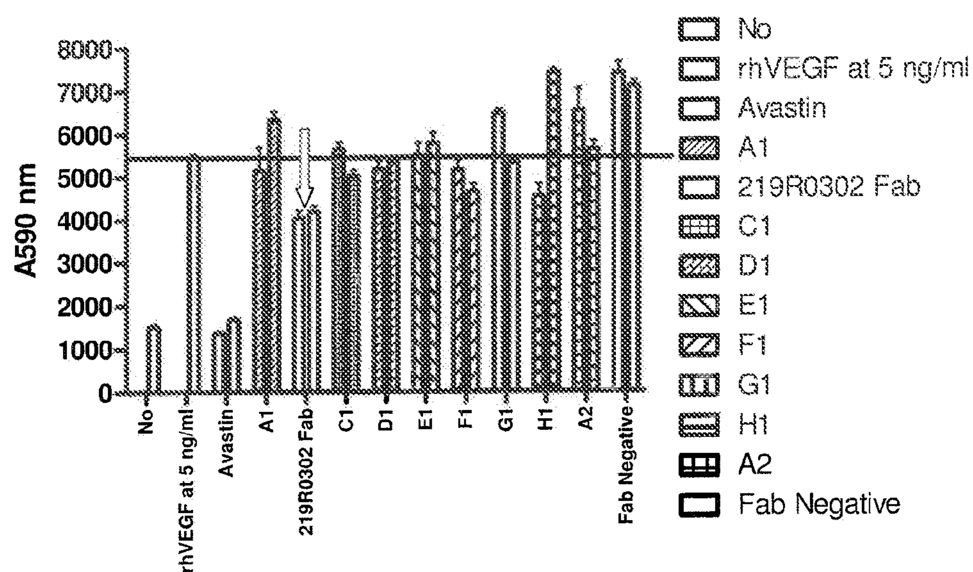

FIG. 8: Anti-VEGF Fab (219R0302) partially blocks VEGF-induced HUVEC proliferation. Day 7 HUVEC cells were screened for inhibition of proliferation against the anti-VEGF Fab fragment 219R0302. M199–+2% FBS was used as the starvation media and the volume was normalized to the lowest concentration of the testing sample. 219R0302 Fab was tested against various test antibodies, bevacizumab (Avastin), and recombinant human VEGF as a control.

FIG. 9: Anti-VEGF Fab (219R0302) blocks binding of VEGFR2 Fc to hVEGF biacore surface. A VEGF surface was generated using standard NHS/EDC chemistry on a CM5 chip. 219R0302 Fab or a control non-binding Fab were flowed over the surface and then immediate thereafter VEGFR2 was injected. As shown, VEGFR2 bound well to VEGF in the control Fab experiment and was blocked in the 219R0302 Fab experiment.

Figure 10:
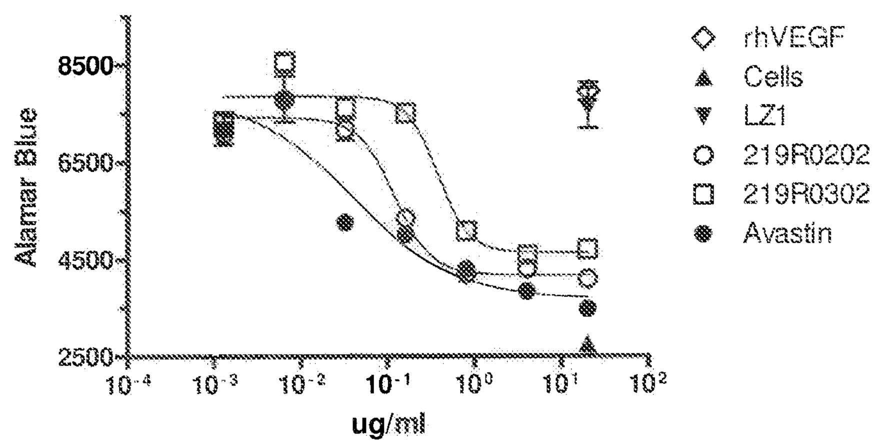

FIG. 10: Anti-VEGF IgGs (219R0302 and 219R0202) block VEGF-induced HUVEC proliferation to similar extent as bevacizumab (Avastin). 21R0302 and 219R0202 IgGs were reformatted to IgG2, expressed, and purified for confirmatory in vitro testing.

Figure 11:
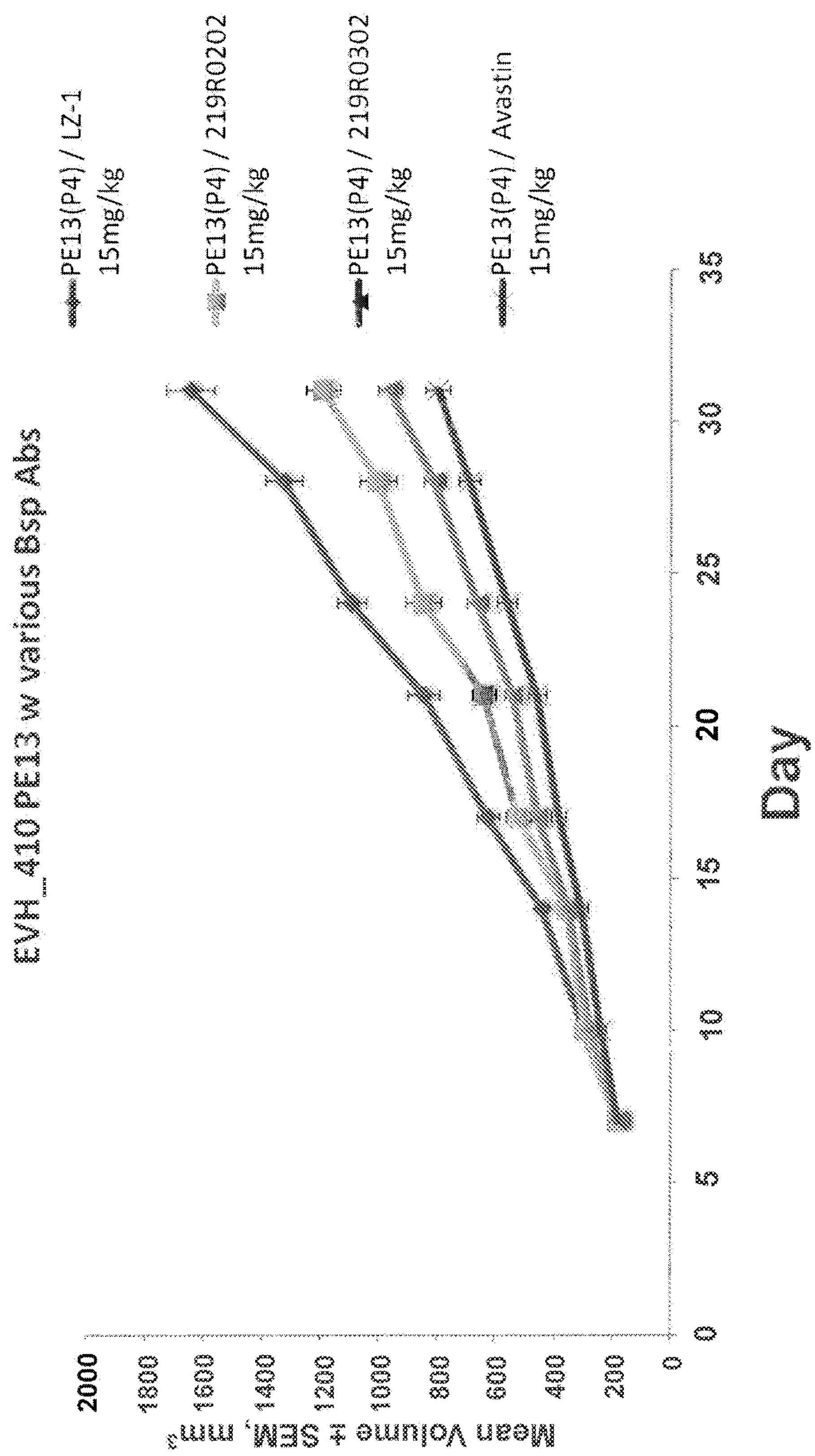

FIG. 11: Anti-VEGF antibodies 219R0302 and 219R0202 inhibit tumor growth in PE13 breast tumor xenograft model. Mice were subcutaneously injected on the right flank with 300,000 viable PE13 cells. 219R0302 induced stronger tumor-growth delay than 219R0202. Avastin showed the most potent growth-delay, which was indistinguishable from 219R0302, indicating that 219R0302 and Avastin have nearly equivalent potency in this model. Unlike 219R0302, 219R0202 was statistically different from both Avastin and 219R0302.

Figure 12:
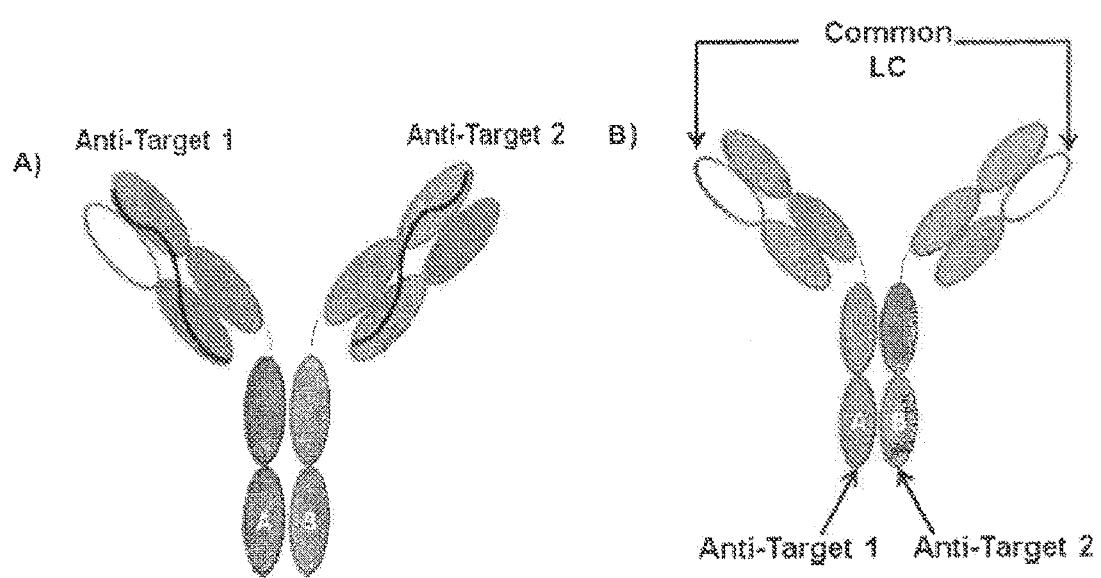

FIG. 12: Bispecific antibody formats. A) Single Gene Bispecific Antibody (SGBSP). In this format, each light chain is tethered to its respective heavy chain via a 30 amino acid linker (6XGGGGS) SEQ ID NO: 37); B) Monovalent Bispecific Antibody (MBSP). In this format, a common light chain is used, which may be derived from either parental antibody. One or both of the heavy chains must be able to bind its target in combination with a common light chain.

Figure 13:
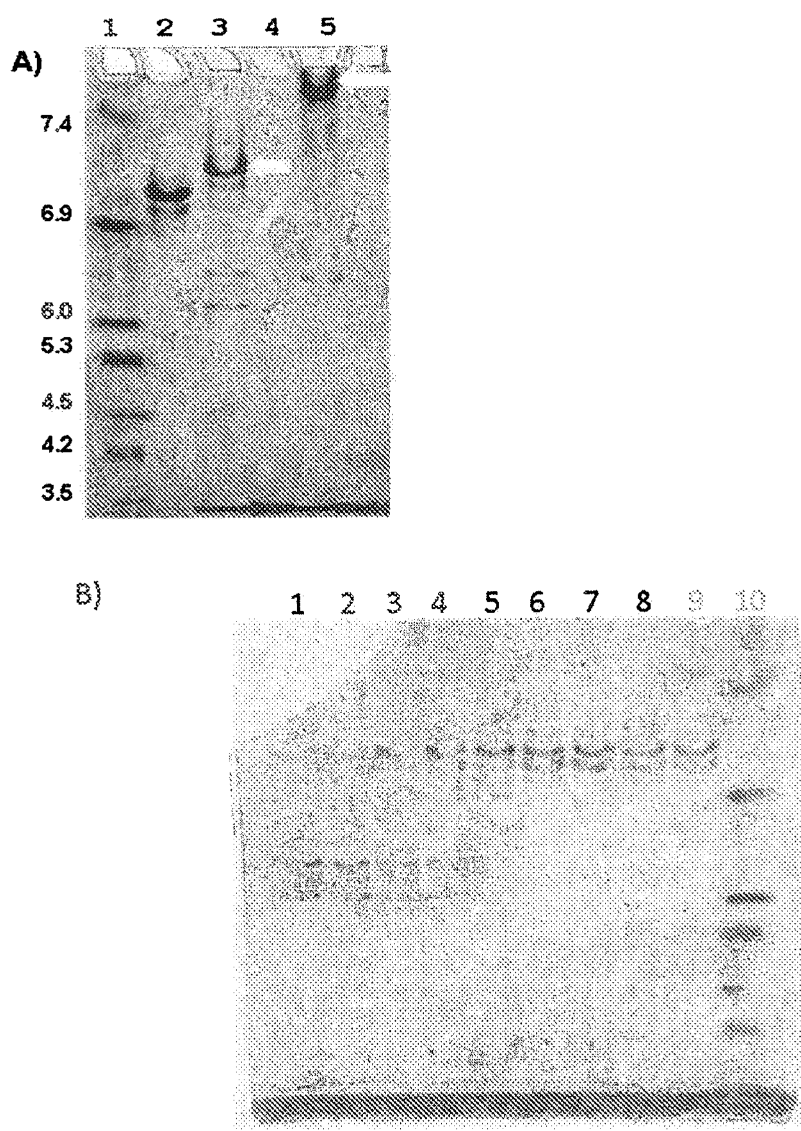

FIG. 13: SGBSP and MBSP are greater than 90% heterodimer and homodimer can be eliminated by varying Var3Var1 ratio. A) Protein A purified SGBSP (219R0202_21M18) and MBSP (219R0202 heavy chain (13A/Var3), 21M18 heavy chain (13B/Var1), 21M18 light chain) are >90% pure and contain a small fraction of Var1 homodimer (SBBSP: 21M18 SGBSP homodimer (13B/Var1); MBSP: 21M18 heavy chain (13B/Var1) with 21M18 light chain). Lane 1: Standard, Lane 2: 21M18, Lane 3: MBSP, Lane 4: Blank, Lane 5: SGBSP. MBSP heterodimer pI~7.1; MBSP 13A homodimer pI~8.3; MBSP 13B homodimer pI~6.2; SGBSP heterodimer pI~7.8; SGBSP 13A homodimer pI~8.6; SGBSP 13B homodimer pI~6.4. B) The fraction of MBSP 13B/Var1 homodimer can be minimized by using at least 2:1 fold molar excess of 219R0202 heavy chain (13A/Var3) to 21M18 heavy chain (13B/Var1). 13A:13B HC Ratio: lane 1, 1:8; lane 2, 1:6; lane 3, 1:4; lane 4, 1:2; lane 5, 1:1; lane 6, 2:1; lane 7, 4:1; lane 8, 6:1; lane 9, 8:1; lane 10, ladder.

Figure 14:
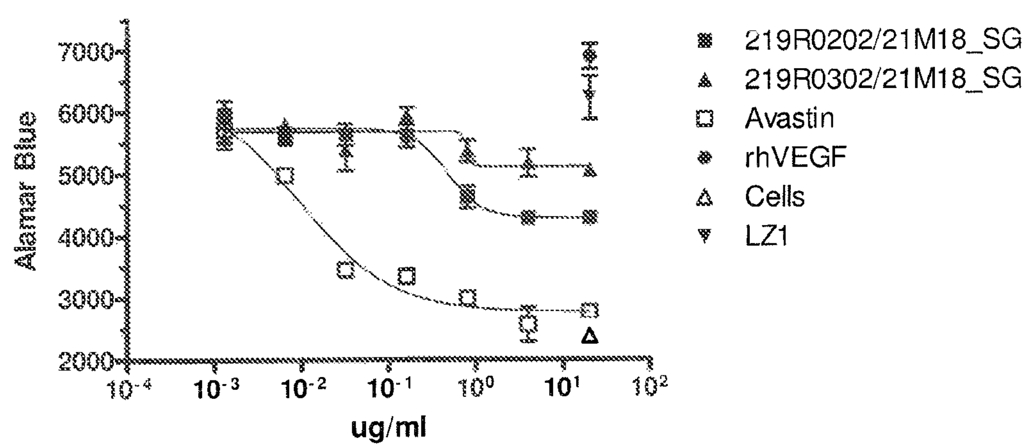

FIG. 14: SGBSPs partially block VEGF-induced HUVEC proliferation. Both 219R0302_21M18 and 219R0202_21M18 SGBSPs partially inhibited VEGF-induced HUVEC proliferation with the latter showing significantly better activity over the former.

Figure 15:
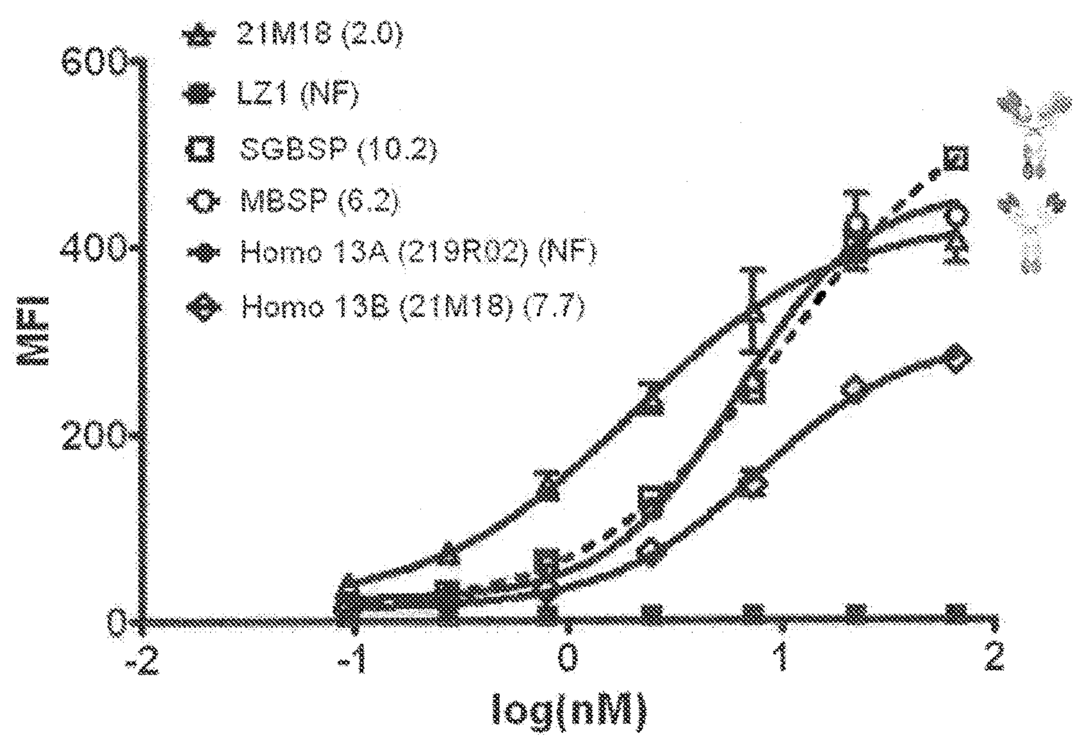

FIG. 15: Bispecific antibodies bind well to hDLL4 transfected cells. LZ1, non-specific antibody control; SGBSP, 219R0202_21M18 single gene bispecific antibody; MBSP, 219R0202_21M18 monovalent bispecific antibody with common 21M18 LC; Homo 13A, 219R0202 HC (with 13A mutation) expressed only with 21M18 LC; Homo 13B, 21M18 HC (with 13B mutation) expressed only with 21M18 LC. The binding curves were fit to a non-linear transform to yield an EC50 value, which is indicated in parentheses (NF, indicates no fit).

FIG. 16: Both SGBSPs and the MBSP bind both VEGF and DLL4 in a bispecific manner. Using the dual targeting assay both 219R0302_21M18 and 219R0202_21M18 both SGBSPs (panel A) and MBSP (panel B) displayed binding to both VEGF and DLL4.

Figure 17:
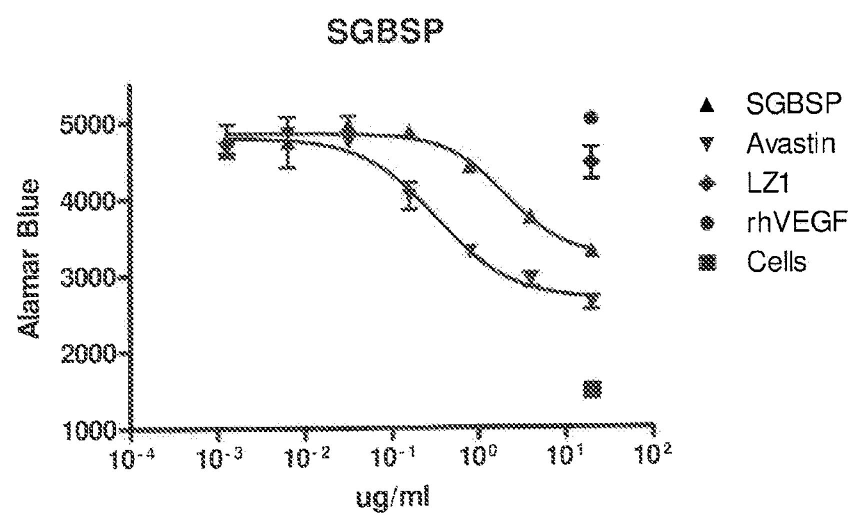

FIG. 17: SGBSP shows partial inhibition in VEGF-induced proliferation assay. SGBSP showed partial inhibition of VEGF-induced proliferation compared to the bevacizumab (Avastin) and rhVEGF controls.

DETAILED DESCRIPTION OF THE INVENTION

The invention provides methods, compositions, and kits for generating heteromultimeric polypeptides, such as bispecific antibodies. The invention enables the generation of predominately (and in certain embodiments, almost exclusively) heteromultimeric molecules having high yields. Details of methods, compositions, and kits are provided herein.

A “heteromultimer”, “heteromultimeric complex”, “heteromultimeric polypeptide”, or “heteromultimeric molecule” are used interchangeably herein to refer to a molecule comprising at least a first polypeptide and a second polypeptide, wherein the second polypeptide differs in amino acid sequence from the first polypeptide by at least one amino acid residue. The heteromultimer can comprise a “heterodimer” formed by the first and second polypeptide or can form higher order tertiary structures where polypeptides in addition to the first and second polypeptide are present.

Except where indicated otherwise by context, the terms “first” polypeptide and “second” polypeptide, and variations thereof, are merely generic identifiers, and are not to be taken as identifying a specific or a particular polypeptide or component of heteromultimers of the invention.

The terms “polypeptide,” “peptide,” “protein,” and “protein fragment” are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid. Negatively charged amino acids include aspartic acid (or aspartate) and glutamic acid (or glutamate). Positively charged amino acids include arginine, histidine, and lysine.

As used herein, the terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and antibody fragments as described herein. The term "bispecific antibody" is intended to include any antibody that has two different binding specificities, i.e. the antibody binds two different epitopes, which can be located on the same target antigen or, more commonly, on different target antigens.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82, 4592-4596 (1985)). Five human immunoglobulin classes are defined on the basis of their heavy chain composition, and are named IgG, IgM, IgA, IgE, and IgD. The IgG-class and IgA-class antibodies are further divided into subclasses, namely, IgG1, IgG2, IgG3, and IgG4, and IgA1 and IgA2. The heavy chains in IgG, IgA, and IgD antibodies have three constant region domains, that are designated CH1, CH2, and CH3, and the heavy chains in IgM and IgE antibodies have four constant region domains, CH1, CH2, CH3, and CH4. Thus, heavy chains have one variable region and three or four constant regions. Immunoglobulin structure and function are reviewed, for example, in Harlow et al., Eds., Antibodies: A Laboratory Manual, Chapter 14, Cold Spring Harbor Laboratory, Cold Spring Harbor (1988).

"Antibody fragments" comprise only a portion of an intact antibody, wherein the portion preferably retains at least one, preferably most or all, of the functions normally associated with that portion when present in an intact antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific and bind a single antigen. Furthermore, in contrast to polyclonal antibody preparations that typically include different antibodies directed against different determinants (epitopes), each monoclonal antibody is directed against a single determinant on the antigen. That an antibody "selectively binds" or "specifically binds" means that the antibody reacts or associates more frequently, more rapidly, with greater duration, with greater affinity, or with some combination of the above to an epitope than with alternative substances, including unrelated proteins. "Selectively binds" or "specifically binds" means, for instance, that an antibody binds to a protein with a $K_D$ of at least about 0.1 mM, but more usually at least about 1 μM. "Selectively binds" or "specifically binds" means at times that an antibody binds to a protein at times with a $K_D$ of at least about 0.1 μM or better, and at other times at least about 0.01 μM or better. Because of the sequence identity between homologous proteins in different species, specific binding can include an antibody that recognizes a tumor cell marker protein in more than one species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

The antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al, Nature 321:522-525 (1986); Riechmann et al, Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23: 1035-1038 (1995); Hurle and Gross, Curr. Op. Biotech. 5:428-433 (1994).

A "human antibody" is one that possesses an amino acid sequence that corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof that result in an improvement in the affinity of the antibody for antigen, compared to a parent antibody that does not possess those alteration(s). Preferred affinity matured antibodies will have nanomolar or even picomolar affinities for the target antigen. Affinity matured antibodies are produced by procedures known in the art. Marks et al., Bio/Technology 10:779-783 (1992), describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region can comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. The Fc sequence of an immunoglobulin generally comprises two constant domains, a CH2 domain and a CH3 domain, and optionally comprises a CH4 domain. By "Fc polypeptide" herein is meant one of the polypeptides that make up an Fc region. An Fc polypeptide can be obtained from any suitable immunoglobulin, such as IgG1, IgG2, IgG3, or IgG4 subtypes, IgA, IgE, IgD, or IgM. In some embodiments, an Fc polypeptide comprises part or all of a wild type hinge sequence (generally at its N terminus). In some embodiments, an Fc polypeptide does not comprise a functional or wild type hinge sequence.

The "hinge region," "hinge sequence", and variations thereof, as used herein, includes the meaning known in the art, which is illustrated in, for example, Janeway et al., Immuno Biology: the immune system in health and disease, (Elsevier Science Ltd., NY) (4th ed., 1999); Bloom et al., Protein Science (1997), 6:407-415; Humphreys et al., J. Immunol. Methods (1997), 209:193-202.

As used herein, the term "hybridizes under stringent conditions" is intended to describe conditions for hybridization and washing under which nucleotide sequences at least 60% homologous to each other typically remain hybridized to each other. In some embodiments, the conditions are such that sequences at least about 70%, at least about 80%, at least about 85% or 90% homologous to each other typically remain hybridized to each other. Such stringent conditions are known to those skilled in the art and can be found in Current Protocols in Molecular Biology, John Wiley & Sons, N.Y. (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50-65° C.

The term "cytotoxin" or "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable vehicle" refers to a diluent, adjuvant, excipient, or carrier with which at least one antibody of the present disclosure is administered.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. To the extent the drug prevents growth and/or kills existing cancer cells, it can be referred to as cytostatic and/or cytotoxic.

As used herein, the terms "polynucleotide" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA, including, but not limited to, 4 acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl 2-thiouracil, 5-carboxymethylaminomethyluracil, dihydrouracil, inosine, N6-isopentenyladenine, 1-methyladenine, 1-methylpseudouracil, 1-methylguanine, 1 -methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2 thiouracil, 2-thiouracil, 4-thiouracil, 5-methyluracil, N-uracil 5-oxyacetic acid methylester, uracil 5-oxyacetic acid, pseudouracil, queosine, 2-thiocytosine, and 2,6-diaminopurine.

The term "vector," as used herein, is intended to refer to a nucleic acid molecule capable of transporting another nucleic acid to which it has been linked. One type of vector is a "plasmid", that refers to a circular double stranded DNA loop into which additional DNA segments can be ligated. Another type of vector is a phage vector. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" can be used interchangeably as the plasmid is the most commonly used form of vector.

The heteromultimeric polypeptides of the present invention can be used to treat a variety of disorders. A "disorder" is any condition that would benefit from treatment with an antibody or method of the invention. This includes chronic and acute disorders or diseases including those pathological conditions that predispose the mammal to the disorder in question. Non-limiting examples of disorders to be treated herein include cell proliferative disorders; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders. The terms "cell proliferative disorder" and "proliferative disorder" refer to disorders that are associated with some degree of abnormal cell proliferation. In one embodiment, the cell proliferative disorder is cancer. "Tumor", as used herein, refers to all neoplastic cell growth and proliferation, whether malignant or benign, and all pre-cancerous and cancerous cells and tissues.

In general, specific antigens are used as targets for the heteromultimeric polypeptides of the invention. In one embodiment, the antigen is a tumor antigen. A "tumor antigen," as used herein, includes any molecule that is differentially expressed on a tumor cell compared to a normal cell. In some embodiments, the molecule is expressed at a detectably or significantly higher or lower level in a tumor cell compared to a normal cell. In some embodiments, the molecule exhibits a detectably or significantly higher or lower level of biological activity in a tumor cell compared to a normal cell. In some embodiments, the molecule is known or thought to contribute to a tumorigenic characteristic of the tumor cell. Numerous tumor antigens are known in the art. Whether a molecule is a tumor antigen can also be determined according to techniques and assays well known to those skilled in the art, such as for example clonogenic assays, transformation assays, in vitro or in vivo tumor formation assays, gel migration assays, gene knockout analysis, etc.

The terms "cancer" or "cancerous" refer to or describe the physiological condition in mammals that is typically characterized by unregulated cell growth/proliferation. Examples of cancer include but are not limited to, carcinoma, lymphoma (e.g., non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result. A "therapeutically effective amount" of an antibody of the invention can vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects.

In one aspect, the invention provides heteromultimeric polypeptides that contain substitutions within their immunoglobulin Fc CH3 domain, wherein the substitutions promote heterodimerization. These substitutions comprise replacement of at least one amino acid in one of the CH3 domain containing polypeptides. In one embodiment, the amino acid that is substituted is a charged amino acid, or a hydrophobic/hydrophilic amino acid.

In certain embodiments, substitutions within the first or second polypeptides of the present invention occur within at least one amino acid in which the side chain projects from or is otherwise positioned at the interface of a first polypeptide with the second polypeptide and is therefore positioned to interact with an amino acid of the second polypeptide that is also positioned at the interface of the two polypeptides. By "interface" is meant the place at which independent polypeptides come into contact with one another. Predicted examples of amino acids located at the interface of two CH3 domain containing polypeptides are shown in Table 1. In one embodiment, changing the amino acid side chain so that the electrostatic interaction between the first and second polypeptides is altered, serves to stabilize the heteromultimer, and thereby favor heteromultimer formation over homomultimer formation. Homomultimer molecules will contain like charged molecules and will naturally repel one another. Heteromultimer molecules contain amino acid pairings having side chains that will attract, thus favoring heteromultimer formation.

In one aspect, the present invention demonstrates that substitution of one or more of the amino acids located at positions 236, 245, 249, 278, 286, and 288, in one of the CH3 domain-containing polypeptides, leads to preferential heteromultimer formation, relative to the amount of homodimer formed. The amino acid positions listed above are positions located within the CH3 domain of IgG2 when the amino acids are numbered beginning with the start of the human IgG2 heavy chain constant domain (i.e., the N-terminus of the CH1 sequence). Amino acid position is variable within the four IgG isotypes, as well as between IgG, IgA, and IgD. Therefore, the specific amino acid positions are not meant to be limiting to the amino acid located at that specific position in any one immunoglobulin, but rather are meant to encompass the amino acid residues in all immunoglobulin isotypes at positions corresponding to those mentioned for the human IgG2 CH3 domain. Such variability of amino acid positioning within the four IgG isotypes is shown in Table 1, and graphically shown in FIGS. 2-4.

Preferential formation of heteromultimeric polypeptides is accomplished by selecting substitutions that differ significantly in their effect on maintaining the charge and/or hydrophobicity of the polypeptide at the target site. Amino acids can be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (Q)

(3) acidic: Asp (D), Glu (E)

(4) basic: Lys (K), Arg (R), His (H)

Alternatively, naturally occurring residues can be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

In some embodiments of the invention, amino acids having basic side chains are replaced with amino acids having acidic side chains, or vice versa. For example, the basic amino acids lysine, arginine, or histidine are replaced with aspartic acid or glutamic acid.

In some embodiments, a hydrophilic amino acid (or at least a relatively hydrophilic amino acid) is substituted with a hydrophobic amino acid. An example of this type of substitution is replacement of a tyrosine residue with a phenylalanine. In certain embodiments, the replacement results in the removal of aa hydroxyl side chain at a specific amino acid position at or near the interface between CH3 domain-containing polypeptides and increasing the hydrophobicity at that site.

As used herein, "Var3" and "13A" are used interchangeably to describe a variant containing a substitution of lysine for glutamate at position 236 and a lysine for aspartate at position 278. Also as used herein, "Var1" and "13B" are used interchangeably to describe a variant containing a substitution of glutamate for lysine at position 249 and a glutamate for lysine at position 288.

In one embodiment, the nucleic acid encoding an amino acid located at the interface is altered for the first polypeptide to change the charge of the amino acid ion pairing. To achieve this, the nucleic acid encoding at least one "original" amino acid residue in the interface of the first polypeptide is replaced with a nucleic acid encoding at least one amino acid residue that has an oppositely charged side chain relative to the original amino acid residue. It will be appreciated that there can be more than one original and corresponding substituted residue. The upper limit for the number of original residues that are replaced is the total number of residues in the interface of the first and second polypeptide.

By "original nucleic acid" is meant the nucleic acid encoding a first or second polypeptide that can be "altered" (i.e. genetically engineered). The original or starting nucleic acid can be a naturally occurring nucleic acid or can comprise a nucleic acid that has been subjected to prior alteration (e.g. a humanized antibody fragment). By "altering" the nucleic acid is meant that the original nucleic acid is modified by replacing at least one codon encoding an amino acid residue of interest. Techniques for genetically modifying a DNA in this manner have been reviewed in Mutagenesis: a Practical Approach, M J. McPherson, Ed., (IRL Press, Oxford, UK. (1991), and include site-directed mutagenesis, cassette mutagenesis and polymerase chain reaction (PCR) mutagenesis, for example. By modifying an original nucleic acid, an original polypeptide encoded by the original nucleic acid is thus correspondingly altered.

In one embodiment of the invention, the heteromultimeric polypeptide is a bispecific antibody. In certain embodiments, the bispecific antibody contains the first polypeptide that is a heavy chain polypeptide paired with a light chain polypeptide, and the second polypeptide that is a second heavy chain polypeptide paired with a second light chain polypeptide.

Heteromultimeric polypeptides with more than two valencies are contemplated. For example, trispecific antibodies can also be prepared using the methods described herein. (Tutt et al., *J. Immunol.,* 147:60 (1991)).

In one embodiment of the present invention, the method comprises producing a heteromultimeric molecule, such as a bispecific antibody, that utilizes a single light chain that can pair with both heavy chain variable domains present in the bispecific molecule. To identify this light chain, various strategies can be employed. In one embodiment, a series of monoclonal antibodies are identified to each antigen that can be targeted with the bispecific antibody, followed by a determination of which of the light chains utilized in these antibodies is able to function when paired with the heavy chain any of the antibodies identified to the second target. In this manner a light chain that can function with two heavy chains to enable binding to both antigens can be identified. In another embodiment, display techniques, such as phage display, can enable the identification of a light chain that can function with two or more heavy chains. In one embodiment, a phage library is constructed which consists of a diverse repertoire of heavy chain variable domains and a single light chain variable domain. This library can further be utilized to identify antibodies that bind to various antigens of interest. Thus, in certain embodiments, the antibodies identified will share a common light chain.

In certain embodiments of the present invention, the heteromultimeric polypeptides comprise at least one single chain Fv (scFv). In certain embodiments the heteromultimeric polypeptide comprise two scFvs. For example, a scFv may be fused to one or both of a CH3 domain-containing polypeptide contained within a heteromultimeric polypeptide. Some methods comprise producing a bispecific molecule wherein one or both of the heavy chain constant regions comprising at least a CH3 domain is utilized in conjunction with a single chain Fv domain to provide antigen binding.

The heteromultimeric molecules can comprise two antigen binding arms of different specificity. For example, heteromultimeric molecules can be generated comprising a first polypeptide which is an antigen binding arm (such as a classical immunoglobulin molecule) and a second polypeptide that is an immunoglobulin fusion protein. An example of immunoglobulin fusion proteins useful in the present invention are immunoadhesins.

As used herein, the term "immunoadhesin" designates antibody-like molecules that combine the "binding domain" of a heterologous protein (an "adhesin", e.g. a receptor, ligand or enzyme) with the effector component of immunoglobulin constant domains. Structurally, immunoadhesins comprise a fusion of the adhesin amino acid sequence with the desired binding specificity, that is other than the antigen recognition and binding site (antigen combining site) of an antibody (i.e. is "heterologous") and an immunoglobulin constant domain sequence. The immunoglobulin constant domain sequence in the immunoadhesin can be obtained from any immunoglobulin, such as IgG1, IgG2, IgG3, or IgG4 subtypes, IgA, IgE, IgD or IgM.

The heteromultimeric polypeptides of the invention can be generated to bind any antigen(s). In some embodiments, the heteromultimeric polypeptides bind one or more antigens selected from the group consisting of: DLL4, VEGF, VEGFR2, Notch1, Notch2, Notch3, Notch4, Notch(pan), JAG1, JAG2, DLL(pan), JAG(pan), EGFR, ERBB2, ERBB3, ERBB(pan), c-Met, IGF-1R, PDGFR, Patched, Hedgehog family polypeptides, Hedgehog(pan), WNT family polypeptides, WNT(pan), FZD1, FZD2, FZD3, FZD4, FZD5, FZD6, FZD7, FZD8, FZD9, FZD10, FZD(pan), LRP5, LRP6, CD20, IL-6 TNFalpha, IL-23, IL-17, CD80, CD86, CD3, CEA, Muc16, PSMA, PSCA, CD44, c-Kit, DDR1, DDR2, RSPO1, RSPO2, RSPO3, RSPO4, RSPO(pan), BMP family polypeptides, BMP(pan), BMPR1a, BMPR1b, and a combination thereof. As used herein, "pan" is meant to describe heteromultimeric polypeptides that bind multiple antigens from within the same family. For example, "Notch(pan)" is meant to describe a heteromultimeric polypeptide that binds more than one of the group of Notch1, Notch2, Notch3, or Notch4.

In one embodiment, the heteromultimeric polypeptide specifically binds DLL4 and VEGF. The 21M18 antibody is produced by the hybridoma deposited with the American Type Culture Collection (ATCC), at 10801 University Boulevard, Manassas, Va., 20110, under the conditions of the Budapest Treaty on Sep. 28, 2007 and having ATCC deposit number PTA-8670.

In one embodiment, one of the polypeptides in a heteromultimeric polypeptide binds DLL4 with the same specificity as the 21M18 antibody described in copending U.S. application Ser. No. 11/905,392, filed Sep. 28, 2007, which is herein incorporated by reference.

In one embodiment, the invention provides antibodies that binds VEGF. In one embodiment, the invention provides an antibody (219R0302) that specifically binds VEGF, wherein the antibody comprises: (a) a heavy chain CDR1 comprising GYTFTNYWMH (SEQ ID NO:20), a heavy chain CDR2 comprising SINPSNGGTSYNEKFKR (SEQ ID NO:21), and a heavy chain CDR3 comprising HYYDNSYAMDY (SEQ ID NO:22); and/or (b) a light chain CDR1 comprising QASQDISNYVN (SEQ ID NO:23), a light chain CDR2 comprising DASNLQT (SEQ ID NO:24), and a light chain CDR3 comprising QQYDDLPP (SEQ ID NO:25). In another embodiment, the invention provides an antibody (219R0202) that specifically binds VEGF, wherein the antibody comprises: (a) a heavy chain CDR1 comprising GYTFTNYWMH (SEQ ID NO:20), a heavy chain CDR2 comprising SINPSNGGTSYNEKFKR (SEQ ID NO:21), and a heavy chain CDR3 comprising HYYDNSYAMDY (SEQ ID NO:22); and/or (b) a light chain CDR1 comprising RASQGINNHLAW (SEQ ID NO:26), a light chain CDR2 comprising AASNLHS (SEQ ID NO:27), and a light chain CDR3 comprising QQYDNLPL (SEQ ID NO:28).

In one embodiment, the VEGF and DLL4 heteromultimeric polypeptides comprise an antibody with the same specificity as 21M18 and either 219R0302 or 219R0202. These heteromultimeric polypeptides can be produced having the light chain linked to the heavy chain, or using an identical light chain. In one embodiment, the antibodies comprise the 13A/13B substitutions, as described herein, in their Fc region.

In one embodiment, the VEGF binding sequence comprises SEQ ID NO:17 or SEQ ID NO:18. In one embodiment, the DLL4 binding sequence comprises SEQ ID NO:19. In another embodiment, the heteromultimeric polypeptide comprises the VEGF binding sequence comprising heavy chain sequence of SEQ ID NO:11 and the light chain sequence of SEQ ID NO:13 or SEQ ID NO:15; and the DLL4 binding sequence comprising SEQ ID NO:19. In another embodiment, the heteromultimeric polypeptide comprises the VEGF binding sequence comprising heavy chain sequence of SEQ ID NO:11 and the light chain sequence of SEQ ID NO:13; and the DLL4 binding sequence comprising SEQ ID NO:19. In a further embodiment, the heteromultimeric polypeptide comprises the VEGF binding sequence comprising heavy chain sequence of SEQ ID NO:11 and the light chain sequence of SEQ ID NO:15; and the DLL4 binding sequence comprising SEQ ID NO:19.

In another embodiment, the VEGF binding sequence comprises a polypeptide selected from the group consisting of SEQ ID NOs:10, 31, and 32. In one embodiment, the VEGF polypeptide is an antibody.

In some embodiments, the heteromultimeric polypeptides or antibodies are intact antibodies such as monoclonal or humanized antibodies. In another embodiment, they antibodies are antibody fragments, such as Fab or scFv. In one embodiment, the anti-VEGF antibodies/polypeptides inhibit tumor growth.

Heteromultimeric polypeptides of the invention can have dual specificity (bivalent) and are capable of binding to two different antigens simultaneously. In one embodiment, the heteromultimeric polypeptides contain two antibody combining sites. In another embodiment, the heteromultimeric polypeptides are bivalent immunoadhesins. The different antigens can be located on different cells or on the same cell. Cross linking of antigen can be shown in vitro, for example by providing a solid surface to which a first antigen has been bound, adding a bispecific antibodies specific for the first antigen and a second antigen for which the binding protein is also specific and detecting the presence of bound second antigen.

Heteromultimeric polypeptides of the invention can, in certain embodiments, block the interaction between two receptors and their respective ligands. For example, a bispecific antibody specific for DLL4 and VEGF inhibits VEGF induced cell migration as well as Notch receptor signaling. In this case, combination of two receptor binding specificities is more efficacious in inhibiting cell migration that the individual parent antibodies.

Heteromultimeric molecules of the invention can also be monovalent, meaning they have one antigen binding site. In one embodiment, the monovalent heteromultimeric polypeptides possess one variable domain, and the second CH3 domain containing polypeptide is truncated such that it does not contain a variable domain. These second CH3 domain containing polypeptides can possess a detectable label. In one embodiment, the monovalent heteromultimeric polypeptide contains a FLAG epitope. The FLAG epitope is a synthetic epitope that consists of eight amino acid residues (DYKDDDDK (SEQ ID NO: 38)). In another embodiment, the monovalent heteromultimeric polypeptide is an immunoadhesin.

In one embodiment, the heteromultimeric molecules of the invention are produced in a first format called single gene bispecific (SGBSP). To generate SBGSPs, a 30 amino acid linker is used to genetically tether, or link, the light chain to its heavy chain (see, Lee et al. *Mol. Immunol.* 36:61-71 (1999). Therefore, each SGBSP binding unit can use its own light chain to form a Fab binding unit that binds its respective target. In one embodiment, the single genes also comprise the Var3/13A and Var1/13B mutations. In one embodiment, anti-DLL4 and anti-VEGF antibodies are used to produce SGBSPs. In one embodiment, the 21M18 and 219R0302/219R0202 heavy chains are produced as SGBSP. In a further embodiment, the 21M18 and 219R0302/219R0202 heavy chains are cloned with the 13B and 13A mutants, respectively.

In another embodiment, the heteromultimeric molecules of the invention are produced in a second format called monovalent bispecific (MBSP). MBSPs use a common light chain with two different heavy chains that comprise the Var3/13A and Var1/13B mutations. For MBSPs, one or both of the heavy chains must bind its target in combination with a common light chain. In some embodiments, the common light chain is the parental light chain for one of the heavy chains. In one embodiment, anti-DLL4 and anti-VEGF antibodies are used to produce SGBSPs. In one embodiment, the 21M18 and 219R0302/219R0202 heavy chains are produced as SGBSP. In a further embodiment, the 21M18 and 219R0302/219R0202 heavy chains are cloned with the 13B and 13A mutants, respectively.

To express heteromultimeric molecules of the invention with selected or random combinations of $V_L$ and $V_H$ domains, V genes encoding those domains are assembled into a bacterial expression vector. For example, a vector can be used that has sequences encoding a bacterial secretion signal sequence and a peptide linker and that has convenient restriction sites for insertion of $V_L$ and $V_H$ genes. Alternatively, it might be desired to first assemble all necessary coding sequences (e.g., secretion signal, $V_L$, $V_H$ and linker peptide) into a single sequence, for example by PCR amplification using overlapping primers, followed by ligation into a plasmid or other vector. Where it is desired to provide a specific combination of $V_L$ and $V_H$ domains, PCR primers specific to the sequences encoding those domains are used. Where it is desired to create diverse combinations of a large number of $V_L$ and $V_H$ domain, mixtures of primers are used to amplify multiple sequences.

Vectors for construction and expression of heteromultimeric polypeptides of the invention in bacteria are available that contain secretion signal sequences and convenient restriction cloning sites. $V_L$ and $V_H$ gene combinations encoding binding sites specific for a particular antigen are isolated from cDNA of B cell hybridomas. Alternatively, random combinations of $V_L$ and $V_H$ genes are obtained from genomic DNA and the products then screened for binding to an antigen of interest. Typically, the polymerase chain reaction (PCR) is employed for cloning, using primers that are compatible with restriction sites in the cloning vector. See, e.g., Dreher, M. L. et al. (1991) J. Immunol. Methods 139:197-205; Ward, E. S. (1993) Adv. Pharmacol. 24:1-20; Chowdhury, P. S. and Pastan, I. (1999) Nat. Biotechnol. 17:568-572.

In one embodiment, the invention provides polynucleotides that express the polypeptides or antibodies described herein. In one embodiment, the invention provides polynucleotides that hybridize under stringent conditions to the polynucleotides that encode the polypeptides or antibodies of the invention. In one embodiment, the polynucleotide comprise the sequences of SEQ ID NOs: 12, 14, or 16.

In one embodiment, bispecific antibodies of the invention are made by expressing 1) a first polypeptide comprising a heavy chain variable domain corresponding to a first specificity connected to a light chain variable domain of a second specificity; and 2) a second polypeptide comprising a light chain variable domain corresponding to the first specificity connected to the heavy chain variable domain of the second specificity.

For certain heteromultimeric polypeptides of the invention, expression in other host cells may be desired. For example, heteromultimeric polypeptides comprising constant domains are often more efficiently expressed in eukaryotic cells, including yeast, insect, vertebrate and mammalian cells. It will be necessary to use such cells where it is desired that the expressed product be glycosylated. The DNA fragments coding for the first and second polypeptides can be cloned, e.g., into HCMV vectors designed to express human light chains of human heavy chains in mammalian cells. (See, eg., Bendig, et al., U.S. Pat. No. 5,840,299; Maeda, et al. (1991) Hum. Antibod. Hybridomas 2, 124-134). Such vectors contain the human cytomegalovirus (HCMV) promoter and enhancer for high level transcription of the light chain and heavy chain constructs. In a preferred embodiment, the light chain expression vector is pKN100 (gift of Dr. S. Tarran Jones, MRC Collaborative Center, London, England), that encodes a human kappa light chain, and the heavy chain expression vector is pG1D105 (gift of Dr. S. Tarran Jones), that encodes a human gamma-1 heavy chain. Both vectors contain HCMV promoters and enhancers, replication origins and selectable: markers functional in mammalian cells and *E. coli.*

A selectable marker is a gene that encodes a protein necessary for the survival or growth of transformed host cells grown in a selective culture medium. Typical selectable markers encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli. A particularly useful selectable marker confers resistance to methotrexate. For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin (1980) Proc. Natl. Acad. Sci. USA 77, 4216. The transformed cells are then exposed to increased levels of methotrexate. This leads to the synthesis of multiple copies of the DHFR gene, and, concomitantly, multiple copies of other DNA comprising the expression vectors, such as the DNA encoding the antibody or antibody fragment. In another example, mutant myeloma cells that are deficient for thymidine kinase (TK) are unable to use exogenously supplied thymidine when aminopterin is used to block DNA synthesis. Useful vectors for transfection carry an intact TK gene that allows growth in media supplemented with thymidine.

Where it is desired to express a gene construct in yeast, a suitable selection gene for use in yeast is the trp1 gene present in the yeast plasmid YRp7. Stinchcomb et al., 1979 Nature, 282, 39; Kingsman et al., 1979, Gene 7, 141. The trp1 gene provides a selection marker for a mutant strain of yeast lacking the ability to grow in tryptophan, for example, ATCC No.44076 or PEP4-1. Jones (1977) Genetics 85,12. The presence of the tip I lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

Preferred host cells for transformation of vectors and expression of antibodies of the present invention are bacterial cells, yeast cells and mammalian cells, e.g., COS-7 cells, Chinese hamster ovary (CHO) cells, and cell lines of lymphoid origin such as lymphoma, myeloma, or hybridoma cells. The transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The heteromultimeric molecules find use in the diagnostic and therapeutic methods described herein. In certain embodiments, the molecules of the present invention are used to detect the expression of a tumor cell marker protein in biological samples such as, for example, a patient tissue biopsy, pleural effusion, or blood sample. Tissue biopsies can be sectioned and protein detected using, for example, immunofluorescence or immunohistochemistry. In addition, individual cells from a sample can be isolated, and protein expression detected on fixed or live cells by FACS analysis. In certain embodiments, heteromultimeric molecules can be used on protein arrays to detect expression of a tumor cell marker, for example, on tumor cells, in cell lysates, or in other protein samples. In certain embodiments, the heteromultimeric molecules of the present invention are used to inhibit the growth of tumor cells by contacting the heteromultimeric molecules with tumor cells in in vitro cell based assays, in vivo animal models, etc. In certain embodiments, the heteromultimeric molecules are used to treat cancer in a patient by administering a therapeutically effective amount of an heteromultimeric molecule against one or more tumor cell markers.

In some embodiments of the present invention, the heteromultimeric molecule is a humanized bispecific antibody. Humanized antibodies are antibodies that contain minimal sequences from non-human (e.g rodent) antibodies within the antigen determination or hypervariable region that comprise the three complementary determination regions (CDRs) within each antibody chain. Such antibodies are used therapeutically to reduce antigenicity and HAMA (human anti-mouse antibody) responses when administered to a human subject. In practice, humanized antibodies are typically human antibodies with minimum to virtually no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDRs of a human antibody with those of a non-human antibody (e.g. mouse, rat, rabbit, hamster, etc.) having the desired specificity, affinity, and capability following the methods of Jones et al., 1986, *Nature,* 321:522-525; Riechmann et al., 1988, *Nature,* 332:323-327; Verhoeyen et al., 1988, *Science,* 239:1534-1536. The humanized antibody can be further modified by the substitution of additional residue either in the variable human framework region and/or within the replaced non-human residues to refine and optimize antibody specificity, affinity, and/or capability.

The choice of human heavy and/or light chain variable domains to be used in making humanized antibodies can be important for reducing antigenicity. According to the "best-fit" method, the sequence of the variable domain of a rodent antibody is screened against the entire library of known human variable-domain amino acid sequences. Thus in certain embodiments, the human amino acid sequence that is most homologous to that of the rodent antibody from which the CDRs are taken is used as the human framework region (FR) for the humanized antibody (Sims et al., 1993, *J. Immunol.,* 151: 2296; Chothia et al., 1987, *J. Mol. Biol.,* 196: 901). Another method uses a particular FR derived from the consensus sequence of all human antibodies of a particular subgroup of light or heavy chains and can be used for several difference humanized antibodies (Carter et al., 1992, *PNAS,* 89; 4285; Presta et al., 1993, *J. Immunol.,* 151: 2623). In certain embodiments, a combination of methods is used to pick the human variable FR to use in generation of humanized antibodies.

It is further understood that antibodies (e.g. rodent) to be humanized must retain high affinity for the antigen as well as other favorable biological properties. To achieve this goal, humanized antibodies can be prepared by a process of analysis of the parental sequence from the rodent antibody to be humanized and the various candidate humanizing sequences. Three-dimensional immunoglobulin models are available and familiar to those skilled in the art. Computer programs can be used to illustrate and display probable three-dimensional conformational structures of selected candidate antibody sequences. Use of such models permits analysis of the likely role of the residues in the function of the antibody to be humanized, i.e., the analysis of residues that influence the ability of the candidate antibody to bind its antigen. In this way, FR residues can be selected and combined from the parental antibody to the recipient humanized antibody so that the desired antibody characteristics are achieved. In general, the residues in the CDRs of the antigen determination region (or hypervariable region) are retained from the parental antibody (e.g. the rodent antibody with the desired antigen binding properties) in the humanized antibody for antigen binding. In certain embodiments, at least one additional residue within the variable FR is retained from the parental antibody in the humanized antibody. In certain embodiments, up to six additional residues within the variable FR are retained from the parental antibody in the humanized antibody.

Amino acids from the variable regions of the mature heavy and light chains of immunoglobulins are designated Hx and Lx respectively, where x is a number designating the position of an amino acid according to the scheme of Kabat, Sequences of Proteins of Immunological Interest, U.S. Department of Health and Human Services, 1987, 1991. Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Moreover, any two antibody sequences can be uniquely aligned, for example to determine percent identity, by using the Kabat numbering system so that each amino acid in one antibody sequence is aligned with the amino acid in the other sequence that has the same Kabat number. In some embodiments, after alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

In addition to humanized antibodies, fully human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, *J. Immunol.,* 147 (1):86-95; and U.S. Pat. No. 5,750,373). Also, the human antibody can be selected from a phage library, where that phage library expresses human antibodies (Vaughan et al., 1996, *Nat. Biotech.,* 14:309-314; Sheets et al., 1998, *Proc. Nat'l. Acad. Sci.,* 95:6157-6162; Hoogenboom and Winter, 1991, *J. Mol. Biol.,* 227:381; Marks et al., 1991, *J. Mol. Biol.,* 222:581). Human antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In one embodiment, the heteromultimeric polypeptides comprise a heavy chain polypeptide of SEQ ID NO:29, or a polypeptide encoded by the nucleic acid of SEQ ID NO:30.

This invention also encompasses bispecific antibodies that specifically recognize an antigen of interest, including but not limited to a tumor cell marker. Bispecific antibodies are antibodies that are capable of specifically recognizing and binding at least two different epitopes (See, e.g., Wu et al., *Simultaneous Targeting of Multiple Disease Mediators by a Dual-Variable-Domain Immunoglobulin*, Nature Biotech., 25(11): 1290-97). The different epitopes can either be within the same molecule (e.g. the same tumor marker polypeptide) or on different molecules such that both, for example, can specifically recognize and bind a tumor cell marker as well. Bispecific antibodies can be intact antibodies or antibody fragments.

Exemplary bispecific antibodies can bind to two different epitopes. Bispecific antibodies can also be used to direct cytotoxic agents to cells that express a particular antigen. These antibodies possess an antigen-binding arm and an arm that binds a cytotoxic agent or a radionuclide chelator, such as EOTUBE, DPTA, DOTA, or TETA. Techniques for making bispecific antibodies are common in the art (Millstein et al., 1983, *Nature* 305:537-539; Brennan et al., 1985, *Science* 229:81; Suresh et al, 1986, *Methods in Enzymol.* 121:120; Traunecker et al., 1991, *EMBO J.* 10:3655-3659; Shalaby et al., 1992, *J. Exp. Med.* 175:217-225; Kostelny et al., 1992, *J. Immunol.* 148:1547-1553; Gruber et al., 1994, *J. Immunol.* 152:5368; and U.S. Pat. No. 5,731,168). Antibodies with more than two valencies are also contemplated. For example, trispecific antibodies can be prepared (Tutt et al., *J. Immunol.* 147:60 (1991))

In certain embodiments are provided a fragment of the heteromultimeric polypeptide to, for example, increase tumor penetration. Various techniques are known for the production of antibody fragments: Traditionally, these fragments are derived via proteolytic digestion of intact antibodies (for example Morimoto et al., 1993, Journal of Biochemical and Biophysical Methods 24:107-117; Brennan et al., 1985, *Science,* 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

It can further be desirable, especially in the case of antibody fragments, to modify a heteromultimeric molecule in order to increase its serum half-life. This can be achieved, for example, by incorporation of a salvage receptor binding epitope into the heteromultimeric molecule by mutation of the appropriate region or by incorporating the epitope into a peptide tag that is then fused to the heteromultimeric molecule at either end or in the middle (e.g., by DNA or peptide synthesis).

For the purposes of the present invention, it should be appreciated that modified antibodies can comprise any type of variable region that provides for the association of the heteromultimer with the polypeptides of interest. In this regard, the variable region can comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

The variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S.

Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified heteromultimers of this invention can comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified heteromultimers disclosed herein can comprise alterations or modifications to one or more of the three heavy chain constant domains (CH1, CH2 or CH3) and/or to the light chain constant domain (CL). In some embodiments of the invention modified constant regions wherein one or more domains are partially or entirely deleted are contemplated. In some embodiments the modified antibodies will comprise domain deleted constructs or variants wherein the entire CH2 domain has been removed (ΔCH2 constructs). In some embodiments the omitted constant region domain will be replaced by a short amino acid spacer (e.g. 10 residues) that provides some of the molecular flexibility typically imparted by the absent constant region.

While not limiting the scope of the present invention, it is believed that heteromultimeric polypeptides comprising constant regions modified as described herein provide for altered effector functions that, in turn, affect the biological profile of the administered polypeptide. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well known biochemical or molecular engineering techniques well within the purview of the skilled artisan.

The invention also pertains to heteromultimeric molecules comprising a heteromultimeric polypeptide conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. In some embodiments, the heteromultimeric molecules can be conjugated to radioisotopes, such as $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re using anyone of a number of well known chelators or direct labeling. In other embodiments, the disclosed compositions can comprise heteromultimeric molecules coupled to drugs, prodrugs or lymphokines such as interferon. Conjugates of the heteromultimeric molecule and cytotoxic agent are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used. In some embodiments, the heteromultimeric polypeptides can be complexed with other immunologically active ligands (e.g. antibodies or fragments thereof) wherein the resulting molecule binds to both the neoplastic cell and an effector cell such as a T cell.

Regardless of how useful quantities are obtained, the heteromultimeric polypeptides of the present invention can be used in any one of a number of conjugated (i.e. an immunoconjugate) or unconjugated forms. Alternatively, the heteromultimeric polypeptides of this invention can be used in a nonconjugated or "naked" form to harness the subject's natural defense mechanisms including complement-dependent cytotoxicity (CDC) and antibody dependent cellular toxicity (ADCC) to eliminate the malignant cells. The selection of which conjugated or unconjugated heteromultimeric polypeptide to use will depend of the type and stage of cancer, use of adjunct treatment (e.g., chemotherapy or external radiation) and patient condition. It will be appreciated that one skilled in the art could readily make such a selection in view of the teachings herein.

The heteromultimeric polypeptides of the present invention can be assayed for immunospecific binding by any method known in the art. The immunoassays which can be used include, but are not limited to, competitive and noncompetitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In some embodiments, the immunospecificity of a heteromultimeric polypeptide against a tumor cell marker is determined using ELISA. An ELISA assay comprises preparing antigen, coating wells of a 96 well microtiter plate with antigen, adding the antibody against a tumor cell marker conjugated to a detectable compound such as an enzymatic substrate (e.g. horseradish peroxidase or alkaline phosphatase) to the well, incubating for a period of time and detecting the presence of the antigen. In some embodiments, the heteromultimeric molecule that binds a tumor cell marker is not conjugated to a detectable compound, but instead a second conjugated antibody that recognizes the heteromultimeric polypeptide against a tumor cell marker is added to the well. In some embodiments, instead of coating the well with the antigen, the antibody against a tumor cell marker can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art (see e.g. Ausubel et al, eds, 1994, Current Protocols in Molecular Biology, Vol. 1, John Wiley & Sons, Inc., New York at 11.2.1).

The binding affinity of a heteromultimeric polypeptide to a tumor cell antigen and the off-rate of an heteromultimer-antigen interaction can be determined by competitive binding assays. One example of a competitive binding assay is a radioimmunoassay comprising the incubation of labeled antigen (e.g. $^{3}H$ or $^{125}I$), or fragment or variant thereof, with the heteromultimeric polypeptide of interest in the presence of increasing amounts of unlabeled antigen followed by the detection of the heteromultimeric polypeptide bound to the labeled antigen. The affinity of the heteromultimeric polypeptide against a tumor cell marker and the binding off-rates can be determined from the data by scatchard plot analysis. In some embodiments, BIAcore kinetic analysis is used to determine the binding on and off rates of heteromultimeric polypeptide against a tumor cell marker. BIAcore kinetic analysis comprises analyzing the binding and dissociation of antibodies from chips with immobilized tumor cell marker antigens on their surface.

In another aspect of the invention, the antibodies can be chemically or biosynthetically linked to anti-tumor agents or detectable signal-producing agents. Anti-tumor agents linked to an antibody include any agents that destroy or damage a tumor to which the antibody has bound or in the environment of the cell to which the antibody has bound. For example, an anti-tumor agent is a toxic agent such as a chemotherapeutic agent or a radioisotope. Suitable chemotherapeutic agents are known to those skilled in the art and include anthracyclines (e.g. daunomycin and doxorubicin), methotrexate, vindesine, neocarzinostatin, cis-platinum, chlorambucil, cytosine arabinoside, 5-fluorouridine, melphalan, ricin and calicheamicin. The chemotherapeutic agents are conjugated to the antibody using conventional methods (See, e.g., Hermentin and Seiler (1988) Behring Inst. Mitt. 82, 197-215).

Detectable signal-producing agents are useful in vivo and in vitro for diagnostic purposes. The signal producing agent produces a measurable signal which is detectible by external means, usually the measurement of electromagnetic radiation. For the most part, the signal producing agent is an enzyme or chromophore, or emits light by fluorescence, phosphorescence or chemiluminescence. Chromophores include dyes that absorb light in the ultraviolet or visible, region, and can be substrates or degradation products of enzyme catalyzed reactions.

The invention further contemplates heteromultimeric polypeptides to which target or reporter moieties are linked. Target moieties are first members of binding pairs. Anti-tumor agents, for example, are conjugated to second members of such pairs and are thereby directed to the site where the antibody is bound. A common example of such a binding pair is avidin and biotin. In one embodiment, biotin is conjugated to a heteromultimeric polypeptide of the invention, and thereby provides a target for an anti-tumor agent or other moiety that is conjugated to avidin or streptavidin. Alternatively, biotin or another such moiety is linked to a heteromultimeric polypeptide of the invention and used as a reporter, for example in a diagnostic system where a detectable signal-producing agent is conjugated to avidin or streptavidin.

The heteromultimeric polypeptides can be administered for therapeutic treatments to a patient suffering from a tumor in an amount sufficient to prevent or reduce the progression of the tumor, e.g, the growth, invasiveness, metastases and/or recurrence of the tumor. An amount adequate to accomplish this is defined as a therapeutically effective dose. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition. Antibodies of the invention can be administered in a single dosages as high as 40 mg/kg body-weight or higher. More preferably, the antibodies are administered in dosages that range from 0.2 mg/kg to 20 mg/kg body-weight. It should be noted, however, that the present invention is not limited to any particular dose.

The present invention can be used to treat any suitable tumor, including, for example, tumors of the breast, heart, lung, small intestine, colon, spleen, kidney, bladder, head and neck, ovary, prostate, brain, pancreas, skin, bone, bone marrow, blood, thymus, uterus, testicles, cervix or liver.

Formulations are prepared for storage and use by combining a purified heteromultimeric polypeptide of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial subcutaneous, intraperitoneal or intramuscular injection or infusion; or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include heteromultimeric polypeptides of the present invention complexed with liposomes (Epstein, et al., 1985, *Proc. Natl. Acad. Sci. USA* 82:3688; Hwang, et al., 1980, *Proc. Natl. Acad. Sci. USA* 77:4030; and U.S. Pat. No. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The heteromultimeric polypeptides can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington, The Science and Practice of Pharmacy 20th Ed. Mack Publishing (2000).

In addition sustained-release preparations can be prepared. Suitable examples of sustained-release preparations include semipermeable matrices of solid hydrophobic polymers containing the antibody, which matrices are in the form of shaped articles (e.g. films, or microcapsules). Examples of sustained-release matrices include polyesters, hydrogels such as poly (2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In some embodiments, the treatment involves the combined administration of a heteromultimeric polypeptides of the present invention and a chemotherapeutic agent or cocktail of multiple different chemotherapeutic agents. Treatment with a heteromultimeric polypeptides can occur prior to, concurrently with, or subsequent to administration of chemotherapies. Chemotherapies contemplated by the invention include chemical substances or drugs that are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine, Gemcitabine, Irinotecan, and Carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In other embodiments, the treatment involves the combined administration of a heteromultimeric polypeptide of the present invention and radiation therapy. Treatment with heteromultimeric polypeptide can occur prior to, concurrently with, or subsequent to administration of radiation therapy. Any dosing schedules for such radiation therapy can be used as determined by the skilled practitioner.

In other embodiments, the treatment can involve the combined administration of heteromultimeric polypeptides of the present invention with antibodies against tumor associated antigens including, but not limited to, antibodies that bind to the EGF receptor (EGFR) (cetuximab/Erbitux®), the erbB2 receptor (HER2) (trastuzumab/Herceptin®), and vascular endothelial growth factor (VEGF) (bevacizumab/Avastin®). Furthermore, treatment can include administration of one or more cytokines, can be accompanied by surgical removal of cancer cells or any other therapy deemed necessary by a treating physician.

In other embodiments, the treatment can involve the combined administration of heteromultimeric polypeptides of the present invention and a second therapeutic. In some embodiments, the second therapeutic is administered to treat a side effect caused by administration of the heteromultimeric polypeptide.

For the treatment of the disease, the appropriate dosage of a heteromultimeric polypeptide of the present invention depends on the type of disease to be treated, the severity and course of the disease, the responsiveness of the disease, whether the heteromultimeric polypeptide is administered for therapeutic or preventative purposes, previous therapy, patient's clinical history, and so on all at the discretion of the treating physician. The heteromultimeric polypeptide can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody. The administering physician can easily determine optimum dosages, dosing methodologies and repetition rates. In general, dosage is from 0.01 μg to 100 mg per kg of body weight, and can be given once or more daily, weekly, monthly or yearly. The treating physician can estimate repetition rates for dosing based on measured residence times and concentrations of the drug in bodily fluids or tissues.

The present invention provides kits comprising the heteromultimeric polypeptides described herein and that can be used to perform the methods described herein. In certain embodiments, a kit comprises at least one purified heteromultimeric polypeptide against a tumor marker in one or more containers. In certain embodiments, a kit comprises at least two heteromultimeric polypeptides. One skilled in the art will readily recognize that the disclosed antibodies of the present invention can be readily incorporated into one of the established kit formats that are well known in the art.

Embodiments of the present disclosure can be further defined by reference to the following examples that describe in detail preparation of heteromultimeric polypeptides of the present disclosure and methods for using heteromultimeric polypeptides of the present disclosure. It will be apparent to those skilled in the art that many modifications, both to materials and methods, can be practiced without departing from the scope of the present disclosure. Wherever possible, the same reference numbers will be used throughout the drawings to refer to the same or like parts. As used herein and in the appended claims, the singular forms "a," "or," and "the" include plural referents unless the context clearly dictates otherwise. Thus, for example, reference to "an antibody" includes a plurality of such antibodies or one or more antibodies and equivalents thereof known to those skilled in the art. Furthermore, all numbers expressing quantities of ingredients, reaction conditions, purity, polypeptide and polynucleotide lengths, and so forth, used in the specification, are modified by the term "about," unless otherwise indicated. Accordingly, the numerical parameters set forth in the specification and claims are approximations that can vary depending upon the desired properties of the present invention.

All of the various embodiments or options described herein can be combined in any and all variations.

EXAMPLES

Example 1

Identification of Candidate Interactions Within the Antibody Dimerization Interface.

In order to better understand the nature of the dimerization interface between antibody heavy chain CH3 domains, the crystal structure of an antibody CH3 domain (structure first reported by Deisenhofer. J. (1981) *Biochemistry,* 20, 2361-2370) was examined. In this structure, the dimerization of the two Fc fragments is mediated by inter-chain interactions between CH3 domains (FIG. 1). The CH3 domain interaction surface contains a central region of hydrophobic residues flanked by residues of both hydrophilic or charged character. Within the core hydrophobic region there are conserved tyrosines which present hydroxyl groups for potential hydrophilic interactions, thus serving both as hydrophobic residues and also serving to enable hydrophilic interactions. FIG. 2 shows depictions of the structure of the ditnerized CH3 domain. One strand is shaded darker than the other for clarity. The side chains of the amino acids which line the interaction surface between CH3 domains are shown. FIG. 3 highlights select amino acids within the CH3 domain involved in potential inter-chain interactions in three separate views of the structure. The amino acid position numbers in FIG. 3 are relative to the constant region of human IgG2. FIG. 4 shows an alignment of the constant domains of the human IgG isotypes. The particular residues that can participate in interchain interactions and that are noted in FIG. 2 are highlighted. Table 1 lists the amino acid position corresponding to these residues that are potentially involved in inter-chain interactions for each of the human IgG isotypes with numbering nomenclature relative to the human IgG germline constant domains.

TABLE 1

| Amino Acid | Human IgG1 Residue # | Human IgG2 Residue # | Human IgG3 Residue # | Human IgG4 Residue # |
|---|---|---|---|---|
| Tyr | 232 | 228 | 279 | 229 |
| Leu | 234 | 230 | 281 | 231 |
| Ser | 237 | 233 | 284 | 234 |
| Glu or Asp | 239 | 235 | 286 | 236 |
| Glu | 240 | 236 | 287 | 237 |
| Lys | 243 | 239 | 290 | 240 |
| Gln | 245 | 241 | 292 | 242 |
| Ser | 247 | 243 | 294 | 244 |
| Thr | 249 | 245 | 296 | 246 |
| Leu | 251 | 247 | 298 | 248 |
| Lys | 253 | 249 | 300 | 250 |
| Asn | 273 | 269 | 320 | 270 |
| Lys or Asn | 275 | 271 | 322 | 272 |
| Thr | 277 | 273 | 324 | 274 |
| Val or Met | 280 | 276 | 327 | 277 |
| Asp | 282 | 278 | 329 | 279 |
| Asp | 284 | 280 | 331 | 281 |
| Ser | 286 | 282 | 333 | 283 |
| Phe | 288 | 284 | 335 | 285 |
| Tyr | 290 | 286 | 337 | 287 |
| Lys or Arg | 292 | 288 | 339 | 289 |
| Thr | 294 | 290 | 341 | 291 |

Example 2

Identification of Fc Variants that Selectively Heterodimerize

The ability of several types of modifications in the CH3 domain of an antibody was analyzed for their ability to generate spontaneously heterodimeric antibodies. It was reasoned that by selectively reducing hydrophilic interactions that occur between each CH3 strand it might be possible to make antibody homodimerization less favorable, and that by simultaneously introducing substitutions that render homodimerization unfavorable, but heterodimerization permissible, it might be possible to generate pairs of compatible Fc variants that selectively heterodimerize, but have very little propensity to homodimerize.

Therefore, a series of variant pairs were created and assessed for their ability to selectively form heterodimeric antibody. Amino acid substitutions were introduced into either a truncated heavy chain (termed mini-body) containing the linker and CH2-CH3 region of a heavy chain, or a full length antibody heavy chain heavy chain. The use of two different sized heavy chains enabled the visualization of the heterodimer species as a molecule of intermediate molecular mass and provided an assay for assessment of the relative propensity of variant antibodies to form heterodimer. This assay format is depicted in cartoon form in FIG. 5. Several variants pairs of antibodies were tested. Amino acid substitutions were introduced into antibody expression vectors that varied the identity of selected amino acids that have the potential to participate in inter-chain interactions. Expression vectors encoding these variant antibody sequences were then transfected alone or in combination with other partner chains into mammalian cells (human HEK 293 cells). After 48 hours, conditioned media from the transfected cells was collected and subjected to western blot analysis and probed with an antibody directed towards the human Fc domain.

As shown in FIG. 6, pairs of variants in which each variant possessed little, if any, propensity for homodimerization were designed, but when co-expressed were able to efficiently contribute to heterodimer formation. Co-expression of antibody variant Var2 (containing amino acid substitutions 249 K to E; 286 Y to F; and 288 K to E) with antibody variant Var3 (13A)

(containing amino acid substitutions 236 E to K; 278 D to K) results in almost exclusive formation of heterodimer. The simultaneous combination of both the alteration of charged amino acids to manipulate attractive and repulsive forces to favor heterodimerization and the alteration of amino acid interactions within the "core" of the antibody ditnerization interface, here accomplished by the elimination of the hydroxyl actions mediated by the central tyrosine through its replacement by the non-polar phenylalanine amino acid residue, to reduce homodimerization propensity. This combination of manipulations enables both the effective reduction of homodimerization and the retention of heterodimerization.

Example 3

Binding of Bispecific Antibody to Two Different Targets

Enyzme-linked immunosorbent assay (ELISA) was conducted to examine the ability of bispecific antibody variant (Var2-Var3) to bind to antigens. ELISA plates were coated with either no antigen (−), anti-FLAG antibody (0.05 mg/ml, clone M2 from SIGMA), or recombinant human delta-like ligand 4 (DLL4) (0.1 mg/ml) (amino acids 27-519 with a carboxy-terminal 8×His tag). Coated plates were then incubated with control cell culture medium (negative control) or conditioned medium from cells transfected with expression vectors encoding Var2, Var3 and light chain L2 as indicated. After allowing binding to occur for 1 hour at room temperature, the plates were washed and bound antibody was detected by use of HRP-conjugated anti-human IgG secondary antibody. The bispecific antibody variant produced by co-expression of variants Var2 and Var3 possesses functional activity (FIG. 7). The Var3 (13A) heavy chain and paired light chain are able to bind to DLL4, the antigen recognized by the parent homodimeric antibody utilized to develop Var3, and the Var2 heavy chain arm displays a FLAG epitope tag and is able to interact with anti-FLAG antibody cy ELISA. Thus, the bispecific antibody is able to interact with two different targets, with each heavy chain being involved in a distinct interaction.

Example 4

Development of Anti-VEGF Antibodies

Mice were immunized with human VEGF and the spleens isolated. The heavy chains were PCR amplified and inserted into a phagemid library of human light chain kappa genes. The phagemid library was rescued and selected against human VEGF for three successive rounds. A panel of VEGF (+) Fabs were isolated and tested in a series of assays to find VEGF antagonists (HUVEC proliferation assay, Biacore blocking assay).

In a HUVEC proliferation assay, one VEGF (+) Fab (219R0302) partially inhibited VEGF-induced HUVEC proliferation (FIG. 8). Briefly, frozen HUVEC cells (Lonza CC-2517) were passaged in ECGM (Lonza CC-3124) and mini-banked. Cells were directly thawed from mini-banked HUVEC in growth media, M199+10% Heat inactivated FBS (Gibco Cat#10082139)+50 μg/ml of EGS (BD:354006)+1X Heparin+1 mM L-Gln. To conduct a proliferation assay, a 96 well plate (Greiner Bio-One Cat#655098) was precoated with 50 μl of 10 μg/ml of Rat Tail Collegen Type I solution (BD: 354236, collegen I was made in 0.02N Acetic Acid) at 4° C. overnight. The next day, the plate was thoroughly aspirated to remove collegen I solution and washed once with 200 μl DPBS. The HUVEC cells were trypsinized off the flask using endothelial cell sub-clone reagent (Lonza: CC-5034). All cells were collected from the flask and isolated via centrifugation at 1200 rpm for 5 minutes at 4° C. The cells were resuspended in starvation/assay media (M199+2% H. I.FBS+1XHeparine+1 mM L+5 units/ml Heparin-Gln) at a density $10^5$ cells/ml. The cells were seeded into the assay plate at 5000/well, 50 μl/well. The cells were then allowed to rest for 3 hours in a 37° C. incubator. The cells were washed carefully once with DPBS by drop-wise adding DPBS 200 μl, and then 100 μl of starvation media was added. Cells were allowed to incubate at 37° C. overnight. The next morning (assay d=0), the testing antibodies (or control: Avastin and LZ1) were prepared in combination with rhVEGF (R&D 293-VE-010). In cases where a titration of different antibody concentrations were tested, 5-fold dilutions (starting from 20 μg/ml of final concentration) were prepared in combination with rhVEGF (5 ng/μl of final concentration) in assay media. These solutions were preincubated at 37° C. for 2 hours. The media from the assay plate was carefully aspirated and 100 μl of the Ab:VEGF mixes were added to the cells. After 3-4 day incubation in a 37° C. incubator, additional Ab+rhVEGF mix (the same final concentration for Ab and rhVEGF were kept) was added to each well and allowed to incubate for another 4 days. On day 7, 20 μl of Alamar Blue reagent (InvitrogenCat#DAL1025) was added to 200 μl culture and incubated at 37° C. for 5 to 6 hours. The plate was read with a fluorescence microplate reader (Ex=530 nm/Em=590 nm).

Fabs were also tested to see if they blocked VEGF-VEGFR2 interaction using the Biacore 2000. Briefly, VEGF was immobilized on a CM5 chip using standard amine based chemistry (NHS/EDC). Anti-VEGF Fabs or control Fab were flowed over the surface at 25 μg/ml and then immediately thereafter, recombinant VEGFR2 was flowed over the surface at 10 μg/ml. Upon further screening and sequencing, an additional light chain variant of this Fab (219R0202) was also discovered and shown to have similar properties (data not shown). The sequences for the 219R0302 and 219R0202 are shown as SEQ ID NOs: 10-16. The 219R0302 Fab completely blocked the binding of VEGFR2 to a VEGF in a Biacore blocking experiment (FIG. 9).

Both IgGs were reformatted to IgG2, expressed, and purified for confirmatory in vitro testing. Both 219R0202 and 219R0302 completely inhibited VEGF induced activation of HUVECS to nearly the same extent as bevacizumab (Avastin) (FIG. 10), an approved anti-VEGF agent.

IgG affinities were determined using a Biacore 2000 instrument. Briefly, recombinant proteins were immobilized on a CM5 chip using standard amine based chemistry (NHS/EDC). For each Fab and IgG, different concentrations (100−1 nM) were injected over the surface and kinetic data were collected over time. The data was fit using the simultaneous global fit equation to yield affinity constants (KD) for each Fab and IgG. 219R0202/219R0302 human and mouse VEGF affinities were determined and compared to Avastin. Unlike Avastin, 219R0202 and 219R0302 bind both human and mouse VEGF (Table 2). This data suggests that 219R0202/219R0302 epitope is not the same as Avastin, which only binds human VEGF.

TABLE 2

219R0302 and 219R0202 bind both human and mouse VEGF

| IgG | hVEGF (nM) | mVEGF (nM) |
|---|---|---|
| 219R0302 | 2.1 | 21 |
| 219R0202 | 1.5 | 23 |
| Avastin | 1.3 | NB |

Both antibodies were also tested in a breast tumor xenograft model (UM-PE13) and exhibited significant inhibition of tumor growth (FIG. 11). Briefly, UM-PE13, a breast tumor xenograft lines, was established at the University of Michigan. Immunocompromised male NOD/SCID mice were used for the establishment of UM-PE13 tumor xenografts. Mice were subcutaneously injected on the right flank with 300,000 viable cells. Once the tumor reached a size between 65 and 200 $mm^3$, mice were randomized. As shown in FIG. 11, 219R0302 induced stronger tumor-growth delay than 219R0202. Avastin showed the most potent growth-delay, which was indistinguishable from 219R0302, indicating that 219R0302 and Avastin have nearly equivalent potency in this model. Unlike 219R0302, 219R0202 was statistically different from both Avastin and 219R0302.

Example 5

Development of Bispecific Antibody Formats

Using the discovered heterodimerization mutations (13A/13B, FIG. 12A), two formats were used to generate a bispecific antibody targeting hDLL4 (21M18) and VEGF (219R0302, 219R0202).

In the first format called Single Gene Bispecific (SGBSP), a 30 amino acid linker (6×GGGGS) SEQ ID NO: 37) linker was used to genetically tether the light chain to its heavy chain as done previously by Lee et al. (Mol. Immunol. 36:61-71 (1999)) (FIG. 12A). In doing so, each binding unit uses its own light chain to form a Fab binding unit that binds its respective target. When coupled with the bispecific mutations (13A/13B) described above, two different single genes are brought together to form a bispecific antibody.

In the second format called Monovalent Bispecific (MBSP), a common light chain was used in concert with two different heavy chains, one harboring the 13A mutation and the other harboring the 13B mutation (FIG. 12B). For this approach, one or both of the heavy chains must be able to bind its target in combination with a common light chain. In some instances, the common light chain is the parental light chain for one of the heavy chains.

Both antibody formats were constructed using 21M18 (anti-human DLL4) and 219R0302/219R0202 (anti-VEGF) as building blocks. The 21M18 and 219R0202/0302 heavy chains were cloned with the 13B and 13A Fc mutants, respectively. Once expressed and purified, each bispecific antibody was tested for anti-DLL4 and anti-VEGF activity compared to control antibody.

To assess dual targeting in the Biacore, a high density VEGF surface was generated as described previously and the bispecific was flowed over at a high concentration to saturate the surface (25 μg/ml). Immediately after bispecific binding to the surface, DLL4-Fc fusion protein was flowed over the same surface at 10 μg/ml. If both arms of the bispecific are functional, then DLL4 should bind to the unbound anti-DLL4 arm of the bound bispecific.

Example 6

Development of Anti-DLL4/Anti-VEGF Single Gene Bispecific (SGBSP) Antibody

A SGBSP was created using 21M18 and either 219R0302 or 219R0202. Both SGBSPs expressed well and were purified by protein A chromatography. To assess the level of homo- vs. heterodimeric species, each SGBSP was assayed using isoelectric focusing. Since the homodimeric species (13A/13B homodimers) have different pI's from the heterodimeric species, the gel clearly shows that both SGBSPs were greater than 90% heterodimer based on gel densitometry (FIG. 13A).

To test their anti-VEGF activity, the antibodies were tested in the same VEGF-induced proliferation assay. As shown in FIG. 14, both 219R0302_21M18 and 219R0202_21M18 SGBSPs partially inhibited VEGF-induced HUVEC proliferation with the latter showing significantly better activity over the former. Since the VEGF binding unit is monomeric in the context of the bispecific, reduced activity is expected due to loss in avidity when compared to Avastin or the parental antibodies (219R0302/219R0202).

Both 219R0302_21M18 and 219R0202_21M18 SGBSPs were also assayed for their VEGF affinity. The 219R0202_21M18 SGBSP binding affinity was approximately 5-fold weaker (6.9 nM) than 219R0202 (1.5 nM), which consistent with a loss in avidity (Table 3). The 219R0302_21M18 SGBSP binding affinity was approximately 4-fold weaker (7.6 nM) than 219R0302 (2.1 nM), which consistent with a loss in avidity (Table 3).

TABLE 3

SGBSP and MBSP VEGF Biacore Analysis.

| IgG | VEGF (nM) |
|---|---|
| 219R0302 | 2.1 |
| 219R0202 | 1.5 |
| 219R0302_21M18 SGBSP | 7.6 |
| 219R0202_21M18 SGBSP | 6.9 |
| 219R0202_21M18 MBSP | 21 |

The 219R0202_21M18 SGBSP was also tested for binding to human DLL4 transfected cells in a FACS binding assay (FIG. 15). When compared to 21M18, there was an approximately 5-fold loss in DLL4 binding activity due to the avidity loss. Briefly, Human 293 HEK cells were transfected using Fugene 6 transfection reagent as recommended by the manufacturer (Roche Inc.). Cells were transfected with cDNA expression vector encoding full length human DLL4, as well as a second vector encoding green fluorescent protein, pcDNA-GFP, to mark the transiently transfected cells. Twenty-four to forty-eight hours post-transfection, cells were incubated with different SGBSP concentrations for 1 hour at 37° C. Cells were then rinsed twice with Staining Medium (HBSS with 2% FCS) and incubated with fluorescent secondary antibody, goat-anti-human IgG H/L-phycoerythrin (PE), at 1:200 dilution in PBS for 1 hour. Cells were then analyzed by flow cytometry using a FACS Caliber instrument (BD Bioscience). Specific SBGSP binding was assessed by determining the presence of cells positive for GFP signal and PE signal.

Using the dual targeting assay described above, both 219R0302_21M18 and 219R0202_21M18 SGBSPs displayed binding to both VEGF and DLL4 as expected (FIG. 16A). The SGBSP also displayed partial inhibition of VEGF-induced proliferation (FIG. 17). Thus, the assays confirm that the bispecific mutations were indeed bringing together each binding unit in a heterodimeric manner and that each binding arm is functional.

Example 7

Development of Anti-DLL4/Anti-VEGF Monovalent Bispecific (MBSP) Antibody

In the second example, a MBSP was created using 21M18 heavy chain, the common 219R0302/219R0202 heavy chain, and 21M18 light chain. The MBSP expressed well and was purified by protein A chromatography. To assess the level of homo- vs. heterodimeric species, the MBSP was assayed using isoelectric focusing. Since the homodimeric species (13A/13B homodimer) have different pI's from the heterodimeric one, IEF gel analysis showed the MBSP was greater than 90% heterodimer based on gel densitometry (FIG. 13A). As shown in FIG. 13B, the remaining 21M18 13B homodimer could be eliminated by increasing the rano of 21R0202 heavy chain (13A) to 21M18 heavy chain (13B).

Since the VEGF binding unit is monomeric and has lost its parental LC in the context of the bispecific, reduced binding activity is expected due to loss in avidity and light chain contribution to binding. As confirmation of this observation, MBSP binding affinity was approximately 14-fold weaker (21 nM) than 219R0202 (1.5 nM), which is consistent with the loss in avidity and light chain binding compared to the parental antibody (Table 3).

The MBSP was also tested for binding to human DLL4 transfected cells in a FACS binding assay (FIG. 15). When compared to 21M18, there was an approximately 3-fold loss in DLL4 binding activity due to the avidity loss.

Using the dual targeting assay as described previously, the MBSP displayed binding to both VEGF and DLL4 as expected (FIG. 16B). This assay confirmed that the bispecific mutations were indeed bringing together each binding unit in a heterodimeric manner and that each binding arm is functional.

SEQUENCES

Sequence Var 1 (13B) (SEQ ID NO: 1) (amino acid substitutions shown in bold)
ASTKGPSVFPLAPCSRSTSESTAALGCLVKDYFPEPVTVSWNSGALTSGVH
TFPAVLQSSGLYSLSSVVTVPSSNFGTQTYTCNVDHKPSNTKVDKTVERKC
CVECPPCPAPPVAGPSVFLFPPKPKDTLMISRTPEVTCVVVDVSHEDPEVQ
FNWYVDGVEVHNAKTKPREEQFNSTFRVVSVLTVVHQDWLNGKEYKCKVSN
KGLPAPIEKTISKTKGQPREPQVYTLPPSREEMTKNQVSLTCLVEGFYPSD
IAVEWESNGQPENNYKTTPPMLDSDGSFFLYSELTVDKSRWQQGNVFSCSV
MHEALHNHYTQKSLSLSPGK Sequence Var 1 (13B) - without CH1 or hinge (SEQ ID NO: 4) (amino acid substitutions shown in bold)
PSVFLFPPKPKDTLMISRTPEVTCVVVDVSHEDPEVQFNWYVDGVEVHNAK
TKPREEQFNSTFRVVSVLYVVHQDWLNGKEYKCKVSNKGLPAPIEKTISKT
KGQPREPQVYTLPPSREEMTKNQVSLTCLVEGFYPSDIAVEWESNGQPENN
YKTTPPMLDSDGSFFLYSELTVDKSRWQQGNVFSCSVMHEALHNHYTQKSL
SLSPGK Sequence Var 1 (13B) - CH3 only (SEQ ID NO: 5) (amino acid substitutions shown in bold)
KTKGQPREPQVYTLPPSREEMTKNQVSLTCLVEGFYPSDIAVEWESNGQPE
NNYKTTPPMLDSDGSFFLYSELTVDKSRWQQGNVFSCSVMHEALHNHYTQK
SLSLSPGK Sequence Var 2 (SEQ ID NO: 2)
ASTKGPSVFPLAPCSRSTSESTAALGCLVKDYFPEPVTVSWNSGALTSGVH
TFPAVLQSSGLYSLSSVVTVPSSNFGTQTYTCNVDHKPSNTKVDKTVERKC
CVECPPCPAPPVAGPSVFLFPPKPKDTLMISRTPEVTCVVVDVSHEDPEVQ
FNWYVDGVEVHNAKTKPREEQFNSTFRVVSVLTVVHQDWLNGKEYKCKVSN
KGLPAPIEKTISKTKGQPREPQVYTLPPSREEMTKNQVSLTCLVEGFYPSD -continued

SEQUENCES

IAVEWESNGQPENNYKTTPPMLDSDGSFFLFSELTVDKSRWQQGNVFSCSV
MHEALHNHYTQKSLSLSPGK

Sequence Var 2 - without CH1 or hinge (SEQ ID NO: 6)
PSVFLFPPKPKDTLMISRTPEVTCVVVDVSHEDPEVQFNWYVDGVEVHNAK
TKPREEQFNSTFRVVSVLTVVHQDWLNGKEYKCKVSNKGLPAPIEKTISKT
KGQPREPQVYTLPPSREEMTKNQVSLTCLVEGFYPSDIAVEWESNGQPENN
YKTTPPMLDSDGSFFLFSELTVDKSRWQQGNVFSCSVMHEALHNHYTQKSL
SLSPGK Sequence Var 2 - CH3 only (SEQ ID NO: 7)
KTKGQPREPQVYTLPPSREEMTKNQVSLTCLVEGFYPSDIAVEWESNGQPE
NNYKTTPPMLDSDGSFFLFSELTVDKSRWQQGNVFSCSVMHEALHNHYTQK
SLSLSPGK Sequence Var3 (13A) (SEQ ID NO: 3) (amino acid substitutions shown in bold)
ASTKGPSVFPLAPCSRSTSESTAALGCLVKDYFPEPVTVSWNSGALTSGVH
TFPAVLQSSGLYSLSSVVTVPSSNFGTQTYTCNVDHKPSNTKVDKTVERKC
CVECPPCPAPPVAGPSVFLFPPKPKDTLMISRTPEVTCVVVDVSHEDPEVQ
FNWYVDGVEVHNAKTKPREEQFNSTFRVVSVLTVVHQDWLNGKEYKCKVSN
KGLPAPIEKTISKTKGQPREPQVYTLPPSREKMTKNQVSLTCLVKGFYPSD
IAVEWESNGQPENNYKTTPPMLKSDGSFFLYSKLTVDKSRWQQGNVFSCSV
MHEALHNHYTQKSLSLSPGK Sequence Var3 (13A) - without CH1 or hinge (SEQ ID NO: 8) (amino acid substitutions shown in bold)
PSVFLFPPKPKDTLMISRTPEVTCVVVDVSHEDPEVQFNWYVDGVEVHNAK
TKPREEQFNSTFRVVSVLTVVHQDWLNGKEYKCKVSNKGLPAPIEKTISKT
KGQPREPQVYTLPPSREKMTKNQVSLTCLVKGFYPSDIAVEWESNGQPENN
YKTTPPMLKSDGSFFLYSKLTVDKSRWQQGNVFSCSVMHEALHNHYTQKSL
SLSPGK Sequence Var3 (13A) - CH3 only (SEQ ID NO: 9) (amino acid substitutions shown in bold)
KTKGQPREPQVYTLPPSREKMTKNQVSLTCLVKGFYPSDIAVEWESNGQPE
NNYKTTPPMLKSDGSFFLYSKLTVDKSRWQQGNVFSCSVMHEALHNHYTQK
SLSLSPGK 219R0302/0202 VH Amino Acid Sequence (SEQ ID NO: 10)
QVQLKQSGAELVKPGASVKLSCKASGYTFTNYWMHWVKLRPGQGFEWIGDI
NPSNGGTSYNEKFKRKATLTVDKSSSTAYMQLSSLTSEDSAVYYCTIHYYD
NSYAMDYWGQGTSVTVSSAST 219R0302/0202 HC Amino Acid Sequence (SEQ ID NO: 11)
QVQLKQSGAELVKPGASVKLSCKASGYTFTNYWMHWVKLRPGQGFEWIGDI
NPSNGGTSYNEKFKRKATLTVDKSSSTAYMQLSSLTSEDSAVYYCTIHYYD
NSYAMDYWGQGTSVTVSSASTKGPSVFPLAPCSRSTSESTAALGCLVKDYF
PEPVTVSWNSGALTSGVHTFPAVLQSSGLYSLSSVVTVPSSNFGTQTYTCN

SEQUENCES

VDHKPSNTKVDKTVERKCCVECPPCPAPPVAGPSVFLFPPKPKDTLMISRT

PEVTCVVVDVSHEDPEVQFNWYVDGVEVHNAKTKPREEQFNSTFRVVSVLT

VVHQDWLNGKEYKCKVSNKGLPAPIEKTISKTKGQPREPQVYTLPPSREEM

TKNQVSLTCLVKGFYPSDIAVEWESNGQPENNYKTTPPMLDSDGSFFLYSK

LTVDKSRWQQGNVFSCSVMHEALHNHYTQKSLSLSPGK

219R0302/0202 HC DNA Sequence (SEQ ID NO: 12)
CAGGTGCAATTGAAGCAGTCTGGGGCTGAACTGGTGAAGCCTGGGGCTTCA

GTGAAGTTGTCCTGCAAGGCTTCTGGCTACACCTTCACCAACTACTGGATG

CACTGGGTGAAGCTGAGGCCTGGACAAGGCTTTGAGTGGATTGGAGATATT

AATCCCAGCAATGGTGGTACTAGCTACAATGAGAAGTTCAAGAGAAAGGCC

ACACTGACTGTAGACAAATCCTCCAGCACAGCCTACATGCAACTCAGCAGC

CTGACATCTGAGGACTCTGCGGTCTATTACTGTACAATACACTACTATGAT

AATTCCTATGCTATGGACTACTGGGGTCAAGGAACCTCAGTCACCGTCAGC

TCAGCCAGCACAAAGGGCCCTAGCGTCTTCCCTCTGGCTCCCTGCAGCAGG

AGCACCAGCGAGAGCACAGCCGCCCTGGGCTGCCTGGTCAAGGACTACTTC

CCCGAACCGGTGACGGTGTCGTGGAACTCAGGCGCTCTGACCAGCGGCGTG

CACACCTTCCCAGCTGTCCTACAGTCCTCAGGACTCTACTCCCTCAGCAGC

GTGGTGACCGTGCCCTCCAGCAACTTCGGCACCCAGACCTACACCTGCAAC

GTAGATCACAAGCCCAGCAACACCAAGGTGGACAAGACAGTTGAGCGCAAA

TGTTGTGTCGAGTGCCCACCGTGCCCAGCACCACCTGTGGCAGGACCGTCA

GTCTTCCTCTTCCCCCCAAAACCCAAGGACACCCTCATGATCTCCCGGACC

CCTGAGGTCACGTGCGTGGTGGTGGACGTGAGCCACGAAGACCCCGAGGTC

CAGTTCAACTGGTACGTGGACGGCGTGGAGGTGCATAATGCCAAGACAAAG

CCACGGGAGGAGCAGTTCAACAGCACGTTCCGTGTGGTCAGCGTCCTCACC

GTTGTGCACCAGGACTGGCTGAACGGCAAGGAGTACAAGTGCAAGGTCTCC

AACAAAGGCCTCCCAGCCCCCATCGAGAAAACCATCTCCAAAACCAAAGGG

CAGCCCCGAGAACCACAGGTGTACACCCTGCCCCCATCCCGGGAGGAGATG

ACCAAGAACCAGGTCAGCCTGACCTGCCTGGTCAAAGGCTTCTACCCCAGC

GACATCGCCGTGGAGTGGGAGAGCAATGGGCAGCCGGAGAACAACTACAAG

ACCACACCTCCCATGCTGGACTCCGACGGCTCCTTCTTCCTCTACAGCAAG

CTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTG

TCTCCGGGTAAA

219R0302 LC Amino Acid Sequence (SEQ ID NO: 13)
DIQMTQSPSSLSASVGDRVTITCQASQDISNYVNWYQQKPGKAPKLLIYDA

SNLQTGVPSRFSGRGSGTHFTFTISSLQPEDLATYYCQQYDDLPPTFGRGT

KLEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

SEQUENCES

219R0302 LC DNA Sequence (SEQ ID NO: 14)
GATATCCAGATGACCCAGTCTCCATCCTCCCTGTCTGCATCTGTCGGAGAC

AGAGTCACCATCACTTGCCAGGCGAGTCAGGACATTAGCAACTATGTAAAT

TGGTATCAACAAAAACCAGGGAAAGCCCCTAAGCTCCTGATCTACGATGCA

TCCAACTTGCAAACAGGGGTCCCATCAAGGTTCAGTGGAAGGGGATCTGGG

ACACATTTTACTTTCACCATCAGCAGCCTGCAGCCTGAAGATCTGGCAACA

TATTACTGTCAACAATATGATGATCTTCCTCCCACTTTTGGCAGAGGGACC

AAGCTGGAGATCAAACGTACGGTGGCTGCACCATCTGTCTTCATCTTCCCG

CCATCTGATGAGCAGTTGAAATCTGGAACTGCCTCTGTTGTGTGCCTGCTG

AATAACTTCTATCCCAGAGAGGCCAAAGTACAGTGGAAGGTGGATAACGCC

CTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAG

AAACACAAAGTCTACGCCTGCGAAGTCACCCATCAGGGCCTGAGCTCGCCC

GTCACAAAGAGCTTCAACAGGGGAGAGTGT

219R0202 LC Amino Acid Sequence (SEQ ID NO: 15)
DIQLTQSPSSLSASVGDRVTITCRASQGINNHLAWYQQKPGKVPKSLIYAA

SNLHSGVPSKFSGSGSGTHFTLIISSLQPEDIATYYCQQYDNLPLTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

219R0202 LC DNA Sequence (SEQ ID NO: 16)
GATATCCAGTTGACCCAGTCTCCATCCTCACTGTCTGCATCTGTCGGAGAC

AGAGTCACCATCACTTGTCGGGCGAGTCAGGGCATCAATAATCATTTAGCC

TGGTATCAGCAGAAACCAGGGAAAGTCCCTAAGTCCCTCATATATGCTGCA

TCCAATCTCCATAGTGGCGTCCCATCAAAGTTCAGCGGCAGTGGATCTGGG

ACACACTTCACTCTCATCATCAGCAGCCTGCAGCCTGAAGATATTGCAACA

TATTACTGTCAACAGTATGATAATCTCCCCCTCACTTTCGGCGGAGGGACC

AAGGTGGAAATCAAACGTACGGTGGCTGCACCATCTGTCTTCATCTTCCCG

CCATCTGATGAGCAGTTGAAATCTGGAACTGCCTCTGTTGTGTGCCTGCTG

AATAACTTCTATCCCAGAGAGGCCAAAGTACAGTGGAAGGTGGATAACGCC

CTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAG

AAACACAAAGTCTACGCCTGCGAAGTCACCCATCAGGGCCTGAGCTCGCCC

GTCACAAAGAGCTTCAACAGGGGAGAGTGT

219R0202_SG (Var3/13A) Amino Acid Sequence (SEQ ID NO: 17) (linker sequence is bold underlined) (13A substitutions shown in bold)
DIQLTQSPSSLSASVGDRVTITCRASQGINNHLAWYQQKPGKVPKSLIYAA

SNLHSGVPSKFSGSGSGTHFTLIISSLQPEDIATYYCQQYDNLPLTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGECGGGGSGGGGSGGGGSGGGGSGGGGSGGGGSQVQLKQSGAE

-continued

| SEQUENCES |
|---|
| LVKPGASVKLSCKASGYTFTNYWMHWVKLRPGQGFEWIGDINPSNGGTSYN |
| EKFKRKATLTVDKSSSTAYMQLSSLTSEDSAVYYCTIHYYDNSYAMDYWGQ |
| GTSVTVSSASTKGPSVFPLAPCSRSTSESTAALGCLVKDYFPEPVTVSWNS |
| GALTSGVHTFPAVLQSSGLYSLSSVVTVPSSNFGTQTYTCNVDHKPSNTKV |
| DKTVERKCCVECPPCPAPPVAGPSVFLFPPKPKDTLMISRTPEVTCVVVDV |
| SHEDPEVQFNWYVDGVEVHNAKTKPREEQFNSTFRVVSVLTVVHQDWLNGK |
| EYKCKVSNKGLPAPIEKTISKTKGQPREPQVYTLPPSRE**K**MTKNQVSLTCL |
| VKGFYPSDIAVEWESNGQPENNYKTTPPML**K**SDGSFFLYSKLTVDKSRWQQ |
| GNVFSCSVMHEALHNHYTQKSLSLSPGK |
| 219R0302_SG (Var3/13A) Amino Acid Sequence (SEQ ID NO: 18) (linker sequence is **bold underlined**) (13A substitutions shown in **bold**) |
| DIQMTQSPSSLSASVGDRVTITCQASQDISNYVNWYQQKPGKAPKLLIYDA |
| SNLQTGVPSRFSGRGSGTHFTFTISSLQPEDLATYYCQQYDDLPPTYGRGT |
| KLEIKRTVAAPSVFIFPPSDEQLKSGTASVVCLLNNFYPREAKVQWKVDNA |
| LQSGNSQESVTEQDSKDSTYSLSSTLTLSKADYEKHKVYACEVTHQGLSSP |
| VTKSFNRGEC**GGGGSGGGGSGGGGSGGGGSGGGGSGGGGS**QVQLKQSGAE |
| LVKPGASVKLSCKASGYTFTNYWMHWVKLRPGQGFEWIGDINPSNGGTSYN |
| EKFKRKATLTVDKSSSTAYMQLSSLTSEDSAVYYCTIHYYDNSYAMDYWGQ |
| GTSVTVSSASTKGPSVFPLAPCSRSTSESTAALGCLVKDYFPEPVTVSWNS |
| GALTSGVHTFPAVLQSSGLYSLSSVVTVPSSNFGTQTYTCNVDHKPSNTKV |
| DKTVERKCCVECPPCPAPPVAGPSVFLFPPKPKDTLMISRTPEVTCVVVDV |
| SHEDPEVQFNWYVDGVEVHNAKTKPREEQFNSTFRVVSVLTVVHQDWLNGK |
| EYKCKVSNKGLPAPIEKTISKTKGQPREPQVYTLPPSRE**K**MTKNQVSLTCL |
| VKGFYPSDIAVEWESNGQPENNYKTTPPML**K**SDGSFFLYSKLTVDKSRWQQ |
| GNVFSCSVMHEALHNHYTQKSLSLSPGK |
| 21M18_SG (Var1/13B) Amino Acid Sequence (SEQ ID NO: 19) (linker sequence is **bold underlined**) (13B substitutions shown in **bold**) |
| DIVMTQSPDSLAVSLGERATISCRASESVDNYGISFMKWFQQKPGQPPKLL |
| IYAASNQGSGVPDRFSGSGSGTDFTLTISSLQAEDVAVYYCQQSKEVPWTF |
| GGGTKVEIKRTVAAPSVFIFPPSDEQLKSGTASVVCLLNNFYPREAKVQWK |
| VDNALQSGNSQESVTEQDSKDSTYSLSSTLTLSKADYEKHKVYACEVTHQG |
| LSSPVTKSFNRGEC**GGGGSGGGGSGGGGSGGGGSGGGGSGGGGS**QVQLVQS |
| GAEVKKPGASVKISCKASGYSFTAYYIHWVKQAPGQGLEWIGYISSYNGAT |
| NYNQKFKGRVTFTTDTSTSTAYMELRSLRSDDTAVYYCARDYDYDVGMDYW |
| GQGTLVTVSSASTKGPSVFPLAPCSRSTSESTAALGCLVKDYFPEPVTVSW |
| NSGALTSGVHTFPAVLQSSGLYSLSSVVTVPSSNFGTQTYTCNVDHKPSNT |
| KVDKTVERKCCVECPPCPAPPVAGPSVFLFPPKPKDTLMISRTPEVTCVVV |
| DVSHEDPEVQFNWYVDGVEVHNAKTKPREEQFNSTFRVVSVLTVVHQDWLN |
| GKEYKCKVSNKGLPAPIEKTISKTKGQPREPQVYTLPPSREEMTKNQVSLT |

-continued

| SEQUENCES |
|---|
| CLV**E**GFYPSDIAVEWESNGQPENNYKTTPPMLDSDGSFFLYS**E**LTVDKSRW |
| QQGNVFSCSVMHEALHNHYTQKSLSLSPGK |
| 21R0302/0202 Heavy chain CDR1 (SEQ ID NO: 20)<br>GYTFTNYWMH |
| 219R0302/0202 Heavy chain CDR2 (SEQ ID NO: 21)<br>SINPSNGGTSYNEKFKR |
| 219R0302/0202 Heavy chain CDR3 (SEQ ID NO: 22)<br>HYYDNSYAMDY |
| 219R0302 Light chain CDR1 (SEQ ID NO: 23)<br>QASQDISNYVN |
| 219R0302 Light chain CDR2 (SEQ ID NO: 24)<br>DASNLQT |
| 219R0302 Light chain CDR3 (SEQ ID NO: 25)<br>QQYDDLPP |
| 219R0202 Light chain CDR1 (SEQ ID NO: 26)<br>RASQGINNHLAW |
| 219R0202 Light chain CDR2 (SEQ ID NO: 27)<br>AASNLHS |
| 219R0202 Light chain CDR3 (SEQ ID NO: 28)<br>QQYDNLPL |
| 219R0202/0302 Humanized HC Amino Acid Sequence (VH1) (SEQ ID NO: 29)<br>QVQLVQSGAEVKKPGASVKVSCKASGYTFTNYWMHWVRQAPGQGLEWMGDI |
| NPSNGGTSYNEKFKRRVTLSVDKSSSTAYMELSSLRSEDTAVYFCTIHYYD |
| NSYAMDYWGQGTLVTVSSASTKGPSVFPLAPCSRSTSESTAALGCLVKDYF |
| PEPVTVSWNSGALTSGVHTFPAVLQSSGLYSLSSVVTVPSSNFGTQTYTCN |
| VDHKPSNTKVDKTVERKCCVECPPCPAPPVAGPSVFLFPPKPKDTLMISRT |
| PEVTCVVVDVSHEDPEVQFNWYVDGVEVHNAKTKPREEQFNSTFRVVSVLT |
| VVHQDWLNGKEYKCKVSNKGLPAPIEKTISKTKGQPREPQVYTLPPSREEM |
| TKNQVSLTCLVKGFYPSDIAVEWESNGQPENNYKTTPPMLDSDGSFFLYSK |
| LTVDKSRWQQGNVFSCSVMHEALHNHYTQKSLSLSPGK |
| 219R0202/0302 Humanized DNA Amino Acid Sequence (VH1) (SEQ ID NO: 30)<br>CAGGTGCAGCTGGTGCAGTCTGGCGCCGAAGTGAAGAAACCTGGCGCCTCC |
| GTGAAGGTGTCCTGCAAGGCCTCCGGCTACACCTTCACCAACTACTGGATG |
| CACTGGGTCCGCCAGGCTCCAGGACAGGGCCTGGAATGGATGGGCGACATC |
| AACCCTTCCAACGGCGGCACCTCCTACAACGAGAAGTTCAAGCGGAGAGTG |
| ACCCTGTCCGTGGACAAGTCCTCCTCCACCGCCTACATGGAACTGTCCTCC |
| CTGCGGTCTGAGGACACCGCCGTGTATTTCTGCACCATCCACTACTACGAC |
| AACTCCTACGCCATGGACTACTGGGGCCAGGGCACCCTGGTCACCGTGTCC |
| TCTGCCTCTACCAAGGGCCCCTCCGTGTTCCCTCTGGCCCCTTGCTCCCGG |
| TCCACCTCTGAGTCTACCGCCGCTCTGGGCTGCCTGGTGAAGGACTACTTC |
| CCTGAGCCTGTGACCGTGTCCTGGAACTCTGGCGCCCTGACCTCTGGCGTG |
| CACACCTTCCCTGCCGTGCTGCAGTCCTCCGGCCTGTACTCCCTGTCCTCC |
| GTGGTGACCGTGCCTTCCTCCAACTTCGGCACCCAGACCTACACCTGCAAC |

-continued

| SEQUENCES |
|---|
| GTGGACCACAAGCCTTCCAACACCAAGGTGGACAAGACCGTGGAGCGGAAG |
| TGCTGCGTGGAGTGCCCTCCTTGTCCTGCTCCTCCTGTGGCTGGCCCTTCT |
| GTGTTCCTGTTCCCTCCTAAGCCTAAGGACACCCTGATGATCTCCCGGACC |
| CCTGAAGTGACCTGCGTGGTGGTGGACGTGTCCCACGAGGACCCTGAGGTG |
| CAGTTCAATTGGTACGTGGACGGCGTGGAGGTGCACAACGCCAAGACCAAG |
| CCTCGGGAGGAACAGTTCAACTCCACCTTCCGGGTGGTGTCTGTGCTGACC |
| GTGGTGCACCAGGACTGGCTGAACGGCAAAGAATACAAGTGCAAGGTGTCC |
| AACAAGGGCCTGCCTGCCCCTATCGAAAAGACCATCTCTAAGACCAAGGGC |
| CAGCCTCGCGAGCCTCAGGTCTACACCCTGCCTCCTAGCCGGGAGGAAATG |
| ACCAAGAACCAGGTGTCCCTGACCTGTCTGGTGAAGGGCTTCTACCCTTCC |
| GATATCGCCGTGGAGTGGGAGTCTAACGGCCAGCCTGAGAACAACTACAAG |
| ACCACCCCTCCTATGCTGGACTCCGACGGCTCCTTCTTCCTGTACTCCAAG |
| CTGACAGTGGACAAGTCCCGGTGGCAGCAGGGCAACGTGTTCTCCTGCTCC |
| HTGATGCACGAGGCCCTGCACAACCACTACACCCAGAAGTCCCTGTCCCTG |
| TCTCCTGGCAAG |
| 219R0302 VL Amino Acid Sequence (SEQ ID NO: 31)<br>DIQMTQSPSSLSASVGDRVTITCQASQDISNYVNWYQQKPGKAPKLLIYDA |
| SNLQTGVPSRFSGRGSGTHFTFTISSLQPEDLATYYCQQYDDLPPTFGRGT |
| KLEIKRT |
| 219R0202 VL Amino Acid Sequence (SEQ ID NO: 32)<br>DIQLTQSPSSLSASVGDRVTITCRASQGINNHLAWYQQKPGKVPKSLIYAA |
| SNLHSGVPSKFSGSGSGTHFTLIISSLQPEDIATYYCQQYDNLPLTFGGGT |
| KVEIKRT |

What is claimed is:

1. A method of preparing a bispecific antibody that specifically binds VEGF and DLL4, wherein the bispecific antibody comprises a first and a second human immunoglobulin heavy chain polypeptide and a first and a second immunoglobulin light chain polypeptide, wherein the first and second immunoglobulin heavy chain polypeptide each comprise a CH3 domain and the CH3 domains comprise substitutions that promote heterodimerization of the first and second immunoglobulin heavy chain polypeptides, and wherein the first and second light chain polypeptides are identical in amino acid sequence, the method comprising substituting amino acids residues within the immunoglobulin heavy chain CH3 domains, and wherein the bispecific antibody is selected from the group consisting of:

(a) a human IgG1, wherein the substitutions consist of: a glutamate or aspartate at positions in the first immunoglobulin heavy chain polypeptide corresponding to positions 253 and 292 of SEQ ID NO:33, and a lysine at positions in the second immunoglobulin heavy chain polypeptide corresponding to positions 240 and 282 of SEQ ID NO:33;

(b) a human IgG2, wherein the substitutions consist of: a glutamate or aspartate at positions in the first immunoglobulin heavy chain polypeptide corresponding to positions 249 and 288 of SEQ ID NO:34 and a lysine at positions in the second immunoglobulin heavy chain polypeptide corresponding to positions 236 and 278 of SEQ ID NO:34;

(c) a human IgG3, wherein the substitutions consist of: a glutamate or aspartate at positions in the first immunoglobulin heavy chain polypeptide corresponding to positions 300 and 339 of SEQ ID NO:35, and a lysine at positions in the second immunoglobulin heavy chain polypeptide corresponding to positions 287 and 329 of SEQ ID NO:35; and (d) a human IgG4, wherein the substitutions consist of: a glutamate or aspartate at positions in the first immunoglobulin heavy chain polypeptide corresponding to positions 250 and 289 of SEQ ID NO:36, and a lysine at positions in the second immunoglobulin heavy chain polypeptide corresponding to positions 237 and 279 of SEQ ID NO:36.

2. The method of claim 1, wherein the bispecific antibody is a human IgG2 antibody and the CH3 domain of the first immunoglobulin heavy chain polypeptide comprises SEQ ID NO:5 or SEQ ID NO:7, and the CH3 domain of the second immunoglobulin heavy chain polypeptide comprises SEQ ID NO:9.

3. The method of claim 1, wherein the bispecific antibody is a human IgG2 antibody, and wherein the substitutions consist of: a glutamate or aspartate at positions in the first immunoglobulin heavy chain polypeptide corresponding to positions 249 and 288 of SEQ ID NO:34, and a lysine at positions in the second immunoglobulin heavy chain polypeptide corresponding to positions 236 and 278 of SEQ ID NO:34.

4. The method of claim 1, wherein the bispecific antibody comprises a VEGF binding sequence, wherein the VEGF binding sequence comprises a heavy chain variable region of SEQ ID NO:10 and a light chain variable region of SEQ ID NO:31 or SEQ ID NO:32.

5. The method of claim 4, wherein the VEGF binding sequence comprises a heavy chain of SEQ ID NO:11 and a light chain of SEQ ID NO:13 or SEQ ID NO:15.

6. The method of claim 4, wherein the bispecific antibody comprises a DLL4 binding sequence, wherein the DLL4 binding sequence has the same specificity as the 21M18 antibody produced by the hybridoma with ATCC designation PTA-8670.

7. The method of claim 1, wherein the bispecific antibody further comprises a cytotoxin or a radioisotope.

8. The method of claim 1, wherein each immunoglobulin heavy chain polypeptide is linked to the immunoglobulin light chain polypeptide.

9. The method of claim 1, wherein the bispecific antibody comprises a DLL4 binding sequence that has the same specificity as the 21M18 antibody produced by the hybridoma with ATCC designation PTA-8670.

* * * * *

SEQUENCE LISTING

```
<160> NUMBER OF SEQ ID NOS: 38

<210> SEQ ID NO 1
<211> LENGTH: 326
<212> TYPE: PRT
<213> ORGANISM: Artificial Sequence
<220> FEATURE:
<223> OTHER INFORMATION: antibody Var 1

<400> SEQUENCE: 1

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205
```

```
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Glu Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Glu
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 2
<211> LENGTH: 326
<212> TYPE: PRT
<213> ORGANISM: Artificial Sequence
<220> FEATURE:
<223> OTHER INFORMATION: antibody Var 2

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240
```

```
Gln Val Ser Leu Thr Cys Leu Val Glu Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Phe Ser Glu
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 3
<211> LENGTH: 326
<212> TYPE: PRT
<213> ORGANISM: Artificial Sequence
<220> FEATURE:
<223> OTHER INFORMATION: antibody Var 3

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Lys Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

```
Thr Pro Pro Met Leu Lys Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 4
<211> LENGTH: 210
<212> TYPE: PRT
<213> ORGANISM: Artificial Sequence
<220> FEATURE:
<223> OTHER INFORMATION: antibody Var 1, without CH1 or hinge

<400> SEQUENCE: 4

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Gln Phe Asn Trp Tyr Val Asp Gly Val Glu Val His
        35                  40                  45

Asn Ala Lys Thr Lys Pro Arg Glu Glu Gln Phe Asn Ser Thr Phe Arg
    50                  55                  60

Val Val Ser Val Leu Thr Val Val His Gln Asp Trp Leu Asn Gly Lys
65                  70                  75                  80

Glu Tyr Lys Cys Lys Val Ser Asn Lys Gly Leu Pro Ala Pro Ile Glu
                85                  90                  95

Lys Thr Ile Ser Lys Thr Lys Gly Gln Pro Arg Glu Pro Gln Val Tyr
            100                 105                 110

Thr Leu Pro Pro Ser Arg Glu Glu Met Thr Lys Asn Gln Val Ser Leu
        115                 120                 125

Thr Cys Leu Val Glu Gly Phe Tyr Pro Ser Asp Ile Ala Val Glu Trp
    130                 135                 140

Glu Ser Asn Gly Gln Pro Glu Asn Asn Tyr Lys Thr Thr Pro Pro Met
145                 150                 155                 160

Leu Asp Ser Asp Gly Ser Phe Phe Leu Tyr Ser Glu Leu Thr Val Asp
                165                 170                 175

Lys Ser Arg Trp Gln Gln Gly Asn Val Phe Ser Cys Ser Val Met His
            180                 185                 190

Glu Ala Leu His Asn His Tyr Thr Gln Lys Ser Leu Ser Leu Ser Pro
        195                 200                 205

Gly Lys
    210


<210> SEQ ID NO 5
<211> LENGTH: 110
<212> TYPE: PRT
<213> ORGANISM: Artificial Sequence
<220> FEATURE:
<223> OTHER INFORMATION: antibody Var 1, CH3 only

<400> SEQUENCE: 5

Lys Thr Lys Gly Gln Pro Arg Glu Pro Gln Val Tyr Thr Leu Pro Pro
1               5                   10                  15

Ser Arg Glu Glu Met Thr Lys Asn Gln Val Ser Leu Thr Cys Leu Val
```

```
            20                  25                  30

Glu Gly Phe Tyr Pro Ser Asp Ile Ala Val Glu Trp Glu Ser Asn Gly
        35                  40                  45

Gln Pro Glu Asn Asn Tyr Lys Thr Thr Pro Pro Met Leu Asp Ser Asp
    50                  55                  60

Gly Ser Phe Phe Leu Tyr Ser Glu Leu Thr Val Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Leu Ser Leu Ser Pro Gly Lys
            100                 105                 110


<210> SEQ ID NO 6
<211> LENGTH: 210
<212> TYPE: PRT
<213> ORGANISM: Artificial Sequence
<220> FEATURE:
<223> OTHER INFORMATION: antibody Var 2, without CH1 or hinge

<400> SEQUENCE: 6

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Gln Phe Asn Trp Tyr Val Asp Gly Val Glu Val His
        35                  40                  45

Asn Ala Lys Thr Lys Pro Arg Glu Glu Gln Phe Asn Ser Thr Phe Arg
    50                  55                  60

Val Val Ser Val Leu Thr Val Val His Gln Asp Trp Leu Asn Gly Lys
65                  70                  75                  80

Glu Tyr Lys Cys Lys Val Ser Asn Lys Gly Leu Pro Ala Pro Ile Glu
                85                  90                  95

Lys Thr Ile Ser Lys Thr Lys Gly Gln Pro Arg Glu Pro Gln Val Tyr
            100                 105                 110

Thr Leu Pro Pro Ser Arg Glu Glu Met Thr Lys Asn Gln Val Ser Leu
        115                 120                 125

Thr Cys Leu Val Glu Gly Phe Tyr Pro Ser Asp Ile Ala Val Glu Trp
    130                 135                 140

Glu Ser Asn Gly Gln Pro Glu Asn Asn Tyr Lys Thr Thr Pro Pro Met
145                 150                 155                 160

Leu Asp Ser Asp Gly Ser Phe Phe Leu Phe Ser Glu Leu Thr Val Asp
                165                 170                 175

Lys Ser Arg Trp Gln Gln Gly Asn Val Phe Ser Cys Ser Val Met His
            180                 185                 190

Glu Ala Leu His Asn His Tyr Thr Gln Lys Ser Leu Ser Leu Ser Pro
        195                 200                 205

Gly Lys
    210


<210> SEQ ID NO 7
<211> LENGTH: 110
<212> TYPE: PRT
<213> ORGANISM: Artificial Sequence
<220> FEATURE:
<223> OTHER INFORMATION: antibody Var 2, CH3 only

<400> SEQUENCE: 7
```

```
Lys Thr Lys Gly Gln Pro Arg Glu Pro Gln Val Tyr Thr Leu Pro Pro
1               5                   10                  15

Ser Arg Glu Glu Met Thr Lys Asn Gln Val Ser Leu Thr Cys Leu Val
            20                  25                  30

Glu Gly Phe Tyr Pro Ser Asp Ile Ala Val Glu Trp Glu Ser Asn Gly
        35                  40                  45

Gln Pro Glu Asn Asn Tyr Lys Thr Thr Pro Pro Met Leu Asp Ser Asp
    50                  55                  60

Gly Ser Phe Phe Leu Phe Ser Glu Leu Thr Val Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Leu Ser Leu Ser Pro Gly Lys
            100                 105                 110
```

<210> SEQ ID NO 8
<211> LENGTH: 210
<212> TYPE: PRT
<213> ORGANISM: Artificial Sequence
<220> FEATURE:
<223> OTHER INFORMATION: antibody Var 3, without CH1 or hinge

<400> SEQUENCE: 8

```
Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Gln Phe Asn Trp Tyr Val Asp Gly Val Glu Val His
        35                  40                  45

Asn Ala Lys Thr Lys Pro Arg Glu Glu Gln Phe Asn Ser Thr Phe Arg
    50                  55                  60

Val Val Ser Val Leu Thr Val Val His Gln Asp Trp Leu Asn Gly Lys
65                  70                  75                  80

Glu Tyr Lys Cys Lys Val Ser Asn Lys Gly Leu Pro Ala Pro Ile Glu
                85                  90                  95

Lys Thr Ile Ser Lys Thr Lys Gly Gln Pro Arg Glu Pro Gln Val Tyr
            100                 105                 110

Thr Leu Pro Pro Ser Arg Glu Lys Met Thr Lys Asn Gln Val Ser Leu
        115                 120                 125

Thr Cys Leu Val Lys Gly Phe Tyr Pro Ser Asp Ile Ala Val Glu Trp
    130                 135                 140

Glu Ser Asn Gly Gln Pro Glu Asn Asn Tyr Lys Thr Thr Pro Pro Met
145                 150                 155                 160

Leu Lys Ser Asp Gly Ser Phe Phe Leu Tyr Ser Lys Leu Thr Val Asp
                165                 170                 175

Lys Ser Arg Trp Gln Gln Gly Asn Val Phe Ser Cys Ser Val Met His
            180                 185                 190

Glu Ala Leu His Asn His Tyr Thr Gln Lys Ser Leu Ser Leu Ser Pro
        195                 200                 205

Gly Lys
    210
```

<210> SEQ ID NO 9
<211> LENGTH: 110
<212> TYPE: PRT
<213> ORGANISM: Artificial Sequence
<220> FEATURE:

<223> OTHER INFORMATION: antibody Var 3, CH3 only

<400> SEQUENCE: 9

```
Lys Thr Lys Gly Gln Pro Arg Glu Pro Gln Val Tyr Thr Leu Pro Pro
1               5                   10                  15

Ser Arg Glu Lys Met Thr Lys Asn Gln Val Ser Leu Thr Cys Leu Val
            20                  25                  30

Lys Gly Phe Tyr Pro Ser Asp Ile Ala Val Glu Trp Glu Ser Asn Gly
        35                  40                  45

Gln Pro Glu Asn Asn Tyr Lys Thr Thr Pro Pro Met Leu Lys Ser Asp
    50                  55                  60

Gly Ser Phe Phe Leu Tyr Ser Lys Leu Thr Val Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Leu Ser Leu Ser Pro Gly Lys
            100                 105                 110
```

<210> SEQ ID NO 10
<211> LENGTH: 123
<212> TYPE: PRT
<213> ORGANISM: Artificial Sequence
<220> FEATURE:
<223> OTHER INFORMATION: antibody 219R0302/0202 VH

<400> SEQUENCE: 10

```
Gln Val Gln Leu Lys Gln Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Leu Arg Pro Gly Gln Gly Phe Glu Trp Ile
        35                  40                  45

Gly Asp Ile Asn Pro Ser Asn Gly Gly Thr Ser Tyr Asn Glu Lys Phe
    50                  55                  60

Lys Arg Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ile His Tyr Tyr Asp Asn Ser Tyr Ala Met Asp Tyr Trp Gly Gln
            100                 105                 110

Gly Thr Ser Val Thr Val Ser Ser Ala Ser Thr
        115                 120
```

<210> SEQ ID NO 11
<211> LENGTH: 446
<212> TYPE: PRT
<213> ORGANISM: Artificial Sequence
<220> FEATURE:
<223> OTHER INFORMATION: antibody 219R0302/0202 HC

<400> SEQUENCE: 11

```
Gln Val Gln Leu Lys Gln Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Leu Arg Pro Gly Gln Gly Phe Glu Trp Ile
        35                  40                  45

Gly Asp Ile Asn Pro Ser Asn Gly Gly Thr Ser Tyr Asn Glu Lys Phe
```

```
    50                  55                  60

Lys Arg Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ile His Tyr Tyr Asp Asn Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 12
<211> LENGTH: 1338
<212> TYPE: DNA
<213> ORGANISM: Artificial Sequence
<220> FEATURE:
<223> OTHER INFORMATION: antibody 219R0302/0202 HC

<400> SEQUENCE: 12

```
caggtgcaat tgaagcagtc tggggctgaa ctggtgaagc ctggggcttc agtgaagttg     60
tcctgcaagg cttctggcta caccttcacc aactactgga tgcactgggt gaagctgagg    120
cctggacaag gctttgagtg gattggagat attaatccca gcaatggtgg tactagctac    180
aatgagaagt tcaagagaaa ggccacactg actgtagaca aatcctccag cacagcctac    240
atgcaactca gcagcctgac atctgaggac tctgcggtct attactgtac aatacactac    300
tatgataatt cctatgctat ggactactgg ggtcaaggaa cctcagtcac cgtcagctca    360
gccagcacaa agggccctag cgtcttccct ctggctccct gcagcaggag caccagcgag    420
agcacagccg ccctgggctg cctggtcaag gactacttcc ccgaaccggt gacggtgtcg    480
tggaactcag gcgctctgac cagcggcgtg cacaccttcc cagctgtcct acagtcctca    540
ggactctact ccctcagcag cgtggtgacc gtgccctcca gcaacttcgg cacccagacc    600
tacacctgca acgtagatca caagcccagc aacaccaagg tggacaagac agttgagcgc    660
aaatgttgtg tcgagtgccc accgtgccca gcaccacctg tggcaggacc gtcagtcttc    720
ctcttccccc caaaacccaa ggacaccctc atgatctccc ggacccctga ggtcacgtgc    780
gtggtggtgg acgtgagcca cgaagacccc gaggtccagt tcaactggta cgtggacggc    840
gtggaggtgc ataatgccaa gacaaagcca cgggaggagc agttcaacag cacgttccgt    900
gtggtcagcg tcctcaccgt tgtgcaccag gactggctga acggcaagga gtacaagtgc    960
aaggtctcca acaaaggcct cccagccccc atcgagaaaa ccatctccaa aaccaaaggg   1020
cagccccgag aaccacaggt gtacaccctg cccccatccc gggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacac ctcccatgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338
```

<210> SEQ ID NO 13
<211> LENGTH: 214
<212> TYPE: PRT
<213> ORGANISM: Artificial Sequence
<220> FEATURE:
<223> OTHER INFORMATION: antibody 219R0302 LC

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Val Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Arg Gly Ser Gly Thr His Phe Thr Phe Thr Ile Ser Ser Leu Gln Pro
65                  70                  75                  80

Glu Asp Leu Ala Thr Tyr Tyr Cys Gln Gln Tyr Asp Asp Leu Pro Pro
                85                  90                  95
```

```
Thr Phe Gly Arg Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 14
<211> LENGTH: 642
<212> TYPE: DNA
<213> ORGANISM: Artificial Sequence
<220> FEATURE:
<223> OTHER INFORMATION: antibody 219R0302 LC

<400> SEQUENCE: 14

gatatccaga tgacccagtc tccatcctcc ctgtctgcat ctgtcggaga cagagtcacc     60

atcacttgcc aggcgagtca ggacattagc aactatgtaa attggtatca acaaaaacca    120

gggaaagccc ctaagctcct gatctacgat gcatccaact tgcaaacagg ggtcccatca    180

aggttcagtg gaaggggatc tgggacacat tttactttca ccatcagcag cctgcagcct    240

gaagatctgg caacatatta ctgtcaacaa tatgatgatc ttcctcccac ttttggcaga    300

gggaccaagc tggagatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 15
<211> LENGTH: 214
<212> TYPE: PRT
<213> ORGANISM: Artificial Sequence
<220> FEATURE:
<223> OTHER INFORMATION: antibody 219R0202 LC

<400> SEQUENCE: 15

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn His
            20                  25                  30

Leu Ala Trp Tyr Gln Gln Lys Pro Gly Lys Val Pro Lys Ser Leu Ile
        35                  40                  45

Tyr Ala Ala Ser Asn Leu His Ser Gly Val Pro Ser Lys Phe Ser Gly
    50                  55                  60

Ser Gly Ser Gly Thr His Phe Thr Leu Ile Ile Ser Ser Leu Gln Pro
```

```
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 16
<211> LENGTH: 642
<212> TYPE: DNA
<213> ORGANISM: Artificial Sequence
<220> FEATURE:
<223> OTHER INFORMATION: antibody 219R0202 LC

<400> SEQUENCE: 16

gatatccagt tgacccagtc tccatcctca ctgtctgcat ctgtcggaga cagagtcacc     60

atcacttgtc gggcgagtca gggcatcaat aatcatttag cctggtatca gcagaaacca    120

gggaaagtcc ctaagtccct catatatgct gcatccaatc tccatagtgg cgtcccatca    180

aagttcagcg gcagtggatc tgggacacac ttcactctca tcatcagcag cctgcagcct    240

gaagatattg caacatatta ctgtcaacag tatgataatc tccccctcac tttcggcgga    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 17
<211> LENGTH: 691
<212> TYPE: PRT
<213> ORGANISM: Artificial Sequence
<220> FEATURE:
<223> OTHER INFORMATION: antibody 219R0202_SG (Var3/13A)

<400> SEQUENCE: 17

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn His
            20                  25                  30

Leu Ala Trp Tyr Gln Gln Lys Pro Gly Lys Val Pro Lys Ser Leu Ile
        35                  40                  45
```

```
Tyr Ala Ala Ser Asn Leu His Ser Gly Val Pro Ser Lys Phe Ser Gly
    50                  55                  60

Ser Gly Ser Gly Thr His Phe Thr Leu Ile Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gln Val Gln Leu Lys Gln Ser Gly Ala Glu Leu
                245                 250                 255

Val Lys Pro Gly Ala Ser Val Lys Leu Ser Cys Lys Ala Ser Gly Tyr
            260                 265                 270

Thr Phe Thr Asn Tyr Trp Met His Trp Val Lys Leu Arg Pro Gly Gln
        275                 280                 285

Gly Phe Glu Trp Ile Gly Asp Ile Asn Pro Ser Asn Gly Gly Thr Ser
    290                 295                 300

Tyr Asn Glu Lys Phe Lys Arg Lys Ala Thr Leu Thr Val Asp Lys Ser
305                 310                 315                 320

Ser Ser Thr Ala Tyr Met Gln Leu Ser Ser Leu Thr Ser Glu Asp Ser
                325                 330                 335

Ala Val Tyr Tyr Cys Thr Ile His Tyr Tyr Asp Asn Ser Tyr Ala Met
            340                 345                 350

Asp Tyr Trp Gly Gln Gly Thr Ser Val Thr Val Ser Ser Ala Ser Thr
        355                 360                 365

Lys Gly Pro Ser Val Phe Pro Leu Ala Pro Cys Ser Arg Ser Thr Ser
    370                 375                 380

Glu Ser Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
                405                 410                 415

Thr Phe Pro Ala Val Leu Gln Ser Ser Gly Leu Tyr Ser Leu Ser Ser
            420                 425                 430

Val Val Thr Val Pro Ser Ser Asn Phe Gly Thr Gln Thr Tyr Thr Cys
        435                 440                 445

Asn Val Asp His Lys Pro Ser Asn Thr Lys Val Asp Lys Thr Val Glu
    450                 455                 460
```

```
Arg Lys Cys Cys Val Glu Cys Pro Pro Cys Pro Ala Pro Pro Val Ala
465                 470                 475                 480

Gly Pro Ser Val Phe Leu Phe Pro Pro Lys Pro Lys Asp Thr Leu Met
                485                 490                 495

Ile Ser Arg Thr Pro Glu Val Thr Cys Val Val Val Asp Val Ser His
            500                 505                 510

Glu Asp Pro Glu Val Gln Phe Asn Trp Tyr Val Asp Gly Val Glu Val
        515                 520                 525

His Asn Ala Lys Thr Lys Pro Arg Glu Glu Gln Phe Asn Ser Thr Phe
    530                 535                 540

Arg Val Val Ser Val Leu Thr Val Val His Gln Asp Trp Leu Asn Gly
545                 550                 555                 560

Lys Glu Tyr Lys Cys Lys Val Ser Asn Lys Gly Leu Pro Ala Pro Ile
                565                 570                 575

Glu Lys Thr Ile Ser Lys Thr Lys Gly Gln Pro Arg Glu Pro Gln Val
            580                 585                 590

Tyr Thr Leu Pro Pro Ser Arg Glu Lys Met Thr Lys Asn Gln Val Ser
        595                 600                 605

Leu Thr Cys Leu Val Lys Gly Phe Tyr Pro Ser Asp Ile Ala Val Glu
    610                 615                 620

Trp Glu Ser Asn Gly Gln Pro Glu Asn Asn Tyr Lys Thr Thr Pro Pro
625                 630                 635                 640

Met Leu Lys Ser Asp Gly Ser Phe Phe Leu Tyr Ser Lys Leu Thr Val
                645                 650                 655

Asp Lys Ser Arg Trp Gln Gln Gly Asn Val Phe Ser Cys Ser Val Met
            660                 665                 670

His Glu Ala Leu His Asn His Tyr Thr Gln Lys Ser Leu Ser Leu Ser
        675                 680                 685

Pro Gly Lys
    690


<210> SEQ ID NO 18
<211> LENGTH: 691
<212> TYPE: PRT
<213> ORGANISM: Artificial Sequence
<220> FEATURE:
<223> OTHER INFORMATION: antibody 219R0302_SG (Var3/13A)

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Val Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Arg Gly Ser Gly Thr His Phe Thr Phe Thr Ile Ser Ser Leu Gln Pro
65                  70                  75                  80

Glu Asp Leu Ala Thr Tyr Tyr Cys Gln Gln Tyr Asp Asp Leu Pro Pro
                85                  90                  95

Thr Phe Gly Arg Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gln Val Gln Leu Lys Gln Ser Gly Ala Glu Leu
                245                 250                 255

Val Lys Pro Gly Ala Ser Val Lys Leu Ser Cys Lys Ala Ser Gly Tyr
            260                 265                 270

Thr Phe Thr Asn Tyr Trp Met His Trp Val Lys Leu Arg Pro Gly Gln
        275                 280                 285

Gly Phe Glu Trp Ile Gly Asp Ile Asn Pro Ser Asn Gly Gly Thr Ser
    290                 295                 300

Tyr Asn Glu Lys Phe Lys Arg Lys Ala Thr Leu Thr Val Asp Lys Ser
305                 310                 315                 320

Ser Ser Thr Ala Tyr Met Gln Leu Ser Ser Leu Thr Ser Glu Asp Ser
                325                 330                 335

Ala Val Tyr Tyr Cys Thr Ile His Tyr Tyr Asp Asn Ser Tyr Ala Met
            340                 345                 350

Asp Tyr Trp Gly Gln Gly Thr Ser Val Thr Val Ser Ser Ala Ser Thr
        355                 360                 365

Lys Gly Pro Ser Val Phe Pro Leu Ala Pro Cys Ser Arg Ser Thr Ser
    370                 375                 380

Glu Ser Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
                405                 410                 415

Thr Phe Pro Ala Val Leu Gln Ser Ser Gly Leu Tyr Ser Leu Ser Ser
            420                 425                 430

Val Val Thr Val Pro Ser Ser Asn Phe Gly Thr Gln Thr Tyr Thr Cys
        435                 440                 445

Asn Val Asp His Lys Pro Ser Asn Thr Lys Val Asp Lys Thr Val Glu
    450                 455                 460

Arg Lys Cys Cys Val Glu Cys Pro Pro Cys Pro Ala Pro Pro Val Ala
465                 470                 475                 480

Gly Pro Ser Val Phe Leu Phe Pro Pro Lys Pro Lys Asp Thr Leu Met
                485                 490                 495

Ile Ser Arg Thr Pro Glu Val Thr Cys Val Val Val Asp Val Ser His
            500                 505                 510

Glu Asp Pro Glu Val Gln Phe Asn Trp Tyr Val Asp Gly Val Glu Val
        515                 520                 525

His Asn Ala Lys Thr Lys Pro Arg Glu Glu Gln Phe Asn Ser Thr Phe
    530                 535                 540

Arg Val Val Ser Val Leu Thr Val Val His Gln Asp Trp Leu Asn Gly
```

```
545                 550                 555                 560

Lys Glu Tyr Lys Cys Lys Val Ser Asn Lys Gly Leu Pro Ala Pro Ile
                565                 570                 575

Glu Lys Thr Ile Ser Lys Thr Lys Gly Gln Pro Arg Glu Pro Gln Val
            580                 585                 590

Tyr Thr Leu Pro Pro Ser Arg Glu Lys Met Thr Lys Asn Gln Val Ser
        595                 600                 605

Leu Thr Cys Leu Val Lys Gly Phe Tyr Pro Ser Asp Ile Ala Val Glu
    610                 615                 620

Trp Glu Ser Asn Gly Gln Pro Glu Asn Asn Tyr Lys Thr Thr Pro Pro
625                 630                 635                 640

Met Leu Lys Ser Asp Gly Ser Phe Phe Leu Tyr Ser Lys Leu Thr Val
                645                 650                 655

Asp Lys Ser Arg Trp Gln Gln Gly Asn Val Phe Ser Cys Ser Val Met
            660                 665                 670

His Glu Ala Leu His Asn His Tyr Thr Gln Lys Ser Leu Ser Leu Ser
        675                 680                 685

Pro Gly Lys
    690


<210> SEQ ID NO 19
<211> LENGTH: 693
<212> TYPE: PRT
<213> ORGANISM: Artificial Sequence
<220> FEATURE:
<223> OTHER INFORMATION: antibody 21M18_SG (Var1/13B)

<400> SEQUENCE: 19

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Asp Asn Tyr
            20                  25                  30

Gly Ile Ser Phe Met Lys Trp Phe Gln Gln Lys Pro Gly Gln Pro Pro
        35                  40                  45

Lys Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Gly
```

```
    210                 215                 220

Gly Gly Gly Ser Gly Gly Gly Gly Ser Gly Gly Gly Gly Ser Gly Gly
225                 230                 235                 240

Gly Gly Ser Gly Gly Gly Gly Ser Gln Val Gln Leu Val Gln Ser Gly
                245                 250                 255

Ala Glu Val Lys Lys Pro Gly Ala Ser Val Lys Ile Ser Cys Lys Ala
            260                 265                 270

Ser Gly Tyr Ser Phe Thr Ala Tyr Tyr Ile His Trp Val Lys Gln Ala
        275                 280                 285

Pro Gly Gln Gly Leu Glu Trp Ile Gly Tyr Ile Ser Ser Tyr Asn Gly
    290                 295                 300

Ala Thr Asn Tyr Asn Gln Lys Phe Lys Gly Arg Val Thr Phe Thr Thr
305                 310                 315                 320

Asp Thr Ser Thr Ser Thr Ala Tyr Met Glu Leu Arg Ser Leu Arg Ser
                325                 330                 335

Asp Asp Thr Ala Val Tyr Tyr Cys Ala Arg Asp Tyr Asp Tyr Asp Val
            340                 345                 350

Gly Met Asp Tyr Trp Gly Gln Gly Thr Leu Val Thr Val Ser Ser Ala
        355                 360                 365

Ser Thr Lys Gly Pro Ser Val Phe Pro Leu Ala Pro Cys Ser Arg Ser
    370                 375                 380

Thr Ser Glu Ser Thr Ala Ala Leu Gly Cys Leu Val Lys Asp Tyr Phe
385                 390                 395                 400

Pro Glu Pro Val Thr Val Ser Trp Asn Ser Gly Ala Leu Thr Ser Gly
                405                 410                 415

Val His Thr Phe Pro Ala Val Leu Gln Ser Ser Gly Leu Tyr Ser Leu
            420                 425                 430

Ser Ser Val Val Thr Val Pro Ser Ser Asn Phe Gly Thr Gln Thr Tyr
        435                 440                 445

Thr Cys Asn Val Asp His Lys Pro Ser Asn Thr Lys Val Asp Lys Thr
    450                 455                 460

Val Glu Arg Lys Cys Cys Val Glu Cys Pro Pro Cys Pro Ala Pro Pro
465                 470                 475                 480

Val Ala Gly Pro Ser Val Phe Leu Phe Pro Pro Lys Pro Lys Asp Thr
                485                 490                 495

Leu Met Ile Ser Arg Thr Pro Glu Val Thr Cys Val Val Val Asp Val
            500                 505                 510

Ser His Glu Asp Pro Glu Val Gln Phe Asn Trp Tyr Val Asp Gly Val
        515                 520                 525

Glu Val His Asn Ala Lys Thr Lys Pro Arg Glu Glu Gln Phe Asn Ser
    530                 535                 540

Thr Phe Arg Val Val Ser Val Leu Thr Val Val His Gln Asp Trp Leu
545                 550                 555                 560

Asn Gly Lys Glu Tyr Lys Cys Lys Val Ser Asn Lys Gly Leu Pro Ala
                565                 570                 575

Pro Ile Glu Lys Thr Ile Ser Lys Thr Lys Gly Gln Pro Arg Glu Pro
            580                 585                 590

Gln Val Tyr Thr Leu Pro Pro Ser Arg Glu Glu Met Thr Lys Asn Gln
        595                 600                 605

Val Ser Leu Thr Cys Leu Val Glu Gly Phe Tyr Pro Ser Asp Ile Ala
    610                 615                 620

Val Glu Trp Glu Ser Asn Gly Gln Pro Glu Asn Asn Tyr Lys Thr Thr
625                 630                 635                 640
```

Pro Pro Met Leu Asp Ser Asp Gly Ser Phe Phe Leu Tyr Ser Glu Leu
645 650 655

Thr Val Asp Lys Ser Arg Trp Gln Gln Gly Asn Val Phe Ser Cys Ser
660 665 670

Val Met His Glu Ala Leu His Asn His Tyr Thr Gln Lys Ser Leu Ser
675 680 685

Leu Ser Pro Gly Lys
690

<210> SEQ ID NO 20
<211> LENGTH: 10
<212> TYPE: PRT
<213> ORGANISM: Artificial Sequence
<220> FEATURE:
<223> OTHER INFORMATION: 21R0302/0202 Heavy chain CDR1

<400> SEQUENCE: 20

Gly Tyr Thr Phe Thr Asn Tyr Trp Met His
1 5 10

<210> SEQ ID NO 21
<211> LENGTH: 17
<212> TYPE: PRT
<213> ORGANISM: Artificial Sequence
<220> FEATURE:
<223> OTHER INFORMATION: 219R0302/0202 Heavy chain CDR2

<400> SEQUENCE: 21

Ser Ile Asn Pro Ser Asn Gly Gly Thr Ser Tyr Asn Glu Lys Phe Lys
1 5 10 15

Arg

<210> SEQ ID NO 22
<211> LENGTH: 11
<212> TYPE: PRT
<213> ORGANISM: Artificial Sequence
<220> FEATURE:
<223> OTHER INFORMATION: 219R0302/0202 Heavy chain CDR3

<400> SEQUENCE: 22

His Tyr Tyr Asp Asn Ser Tyr Ala Met Asp Tyr
1 5 10

<210> SEQ ID NO 23
<211> LENGTH: 11
<212> TYPE: PRT
<213> ORGANISM: Artificial Sequence
<220> FEATURE:
<223> OTHER INFORMATION: 219R0302 Light chain CDR1

<400> SEQUENCE: 23

Gln Ala Ser Gln Asp Ile Ser Asn Tyr Val Asn
1 5 10

<210> SEQ ID NO 24
<211> LENGTH: 7
<212> TYPE: PRT
<213> ORGANISM: Artificial Sequence
<220> FEATURE:
<223> OTHER INFORMATION: 219R0302 Light chain CDR2

<400> SEQUENCE: 24

Asp Ala Ser Asn Leu Gln Thr
1 5

<210> SEQ ID NO 25
<211> LENGTH: 8
<212> TYPE: PRT
<213> ORGANISM: Artificial Sequence
<220> FEATURE:
<223> OTHER INFORMATION: 219R0302 Light chain CDR3

<400> SEQUENCE: 25

Gln Gln Tyr Asp Asp Leu Pro Pro
1               5

<210> SEQ ID NO 26
<211> LENGTH: 12
<212> TYPE: PRT
<213> ORGANISM: Artificial Sequence
<220> FEATURE:
<223> OTHER INFORMATION: 219R0202 Light chain CDR1

<400> SEQUENCE: 26

Arg Ala Ser Gln Gly Ile Asn Asn His Leu Ala Trp
1               5                   10

<210> SEQ ID NO 27
<211> LENGTH: 7
<212> TYPE: PRT
<213> ORGANISM: Artificial Sequence
<220> FEATURE:
<223> OTHER INFORMATION: 219R0202 Light chain CDR2

<400> SEQUENCE: 27

Ala Ala Ser Asn Leu His Ser
1               5

<210> SEQ ID NO 28
<211> LENGTH: 8
<212> TYPE: PRT
<213> ORGANISM: Artificial Sequence
<220> FEATURE:
<223> OTHER INFORMATION: 219R0202 Light chain CDR3

<400> SEQUENCE: 28

Gln Gln Tyr Asp Asn Leu Pro Leu
1               5

<210> SEQ ID NO 29
<211> LENGTH: 446
<212> TYPE: PRT
<213> ORGANISM: Artificial Sequence
<220> FEATURE:
<223> OTHER INFORMATION: 219R0202/0302 Humanized HC

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Asp Ile Asn Pro Ser Asn Gly Gly Thr Ser Tyr Asn Glu Lys Phe
    50                  55                  60

Lys Arg Arg Val Thr Leu Ser Val Asp Lys Ser Ser Ser Thr Ala Tyr
65                  70                  75                  80

Met Glu Leu Ser Ser Leu Arg Ser Glu Asp Thr Ala Val Tyr Phe Cys

```
                85                  90                  95

Thr Ile His Tyr Tyr Asp Asn Ser Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 30
<211> LENGTH: 1338
<212> TYPE: DNA
<213> ORGANISM: Artificial Sequence
<220> FEATURE:
<223> OTHER INFORMATION: antibody 219R0202/0302 Humanized

<400> SEQUENCE: 30

```
caggtgcagc tggtgcagtc tggcgccgaa gtgaagaaac ctggcgcctc cgtgaaggtg     60
```

```
tcctgcaagg cctccggcta caccttcacc aactactgga tgcactgggt ccgccaggct    120
ccaggacagg gcctggaatg gatgggcgac atcaaccctt ccaacggcgg cacctcctac    180
aacgagaagt tcaagcggag agtgaccctg tccgtggaca agtcctcctc caccgcctac    240
atggaactgt cctccctgcg gtctgaggac accgccgtgt atttctgcac catccactac    300
tacgacaact cctacgccat ggactactgg ggccagggca ccctggtcac cgtgtcctct    360
gcctctacca agggcccctc cgtgttccct ctggcccctt gctcccggtc cacctctgag    420
tctaccgccg ctctgggctg cctggtgaag gactacttcc ctgagcctgt gaccgtgtcc    480
tggaactctg gcgccctgac ctctggcgtg cacaccttcc ctgccgtgct gcagtcctcc    540
ggcctgtact ccctgtcctc cgtggtgacc gtgccttcct ccaacttcgg cacccagacc    600
tacacctgca acgtggacca caagccttcc aacaccaagg tggacaagac cgtggagcgg    660
aagtgctgcg tggagtgccc tccttgtcct gctcctcctg tggctggccc ttctgtgttc    720
ctgttccctc ctaagcctaa ggacaccctg atgatctccc ggacccctga agtgacctgc    780
gtggtggtgg acgtgtccca cgaggaccct gaggtgcagt tcaattggta cgtggacggc    840
gtggaggtgc acaacgccaa gaccaagcct cgggaggaac agttcaactc caccttccgg    900
gtggtgtctg tgctgaccgt ggtgcaccag gactggctga acggcaaaga atacaagtgc    960
aaggtgtcca acaagggcct gcctgcccct atcgaaaaga ccatctctaa gaccaagggc   1020
cagcctcgcg agcctcaggt ctacaccctg cctcctagcc gggaggaaat gaccaagaac   1080
caggtgtccc tgacctgtct ggtgaagggc ttctaccctt ccgatatcgc cgtggagtgg   1140
gagtctaacg gccagcctga gaacaactac aagaccaccc ctcctatgct ggactccgac   1200
ggctccttct tcctgtactc caagctgaca gtggacaagt cccggtggca gcagggcaac   1260
gtgttctcct gctccgtgat gcacgaggcc ctgcacaacc actacaccca gaagtccctg   1320
tccctgtctc ctggcaag                                                 1338
```

```
<210> SEQ ID NO 31
<211> LENGTH: 109
<212> TYPE: PRT
<213> ORGANISM: Artificial Sequence
<220> FEATURE:
<223> OTHER INFORMATION: antibody 219R0302 VL

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Val Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Arg Gly Ser Gly Thr His Phe Thr Phe Thr Ile Ser Ser Leu Gln Pro
65                  70                  75                  80

Glu Asp Leu Ala Thr Tyr Tyr Cys Gln Gln Tyr Asp Asp Leu Pro Pro
                85                  90                  95

Thr Phe Gly Arg Gly Thr Lys Leu Glu Ile Lys Arg Thr
            100                 105


<210> SEQ ID NO 32
<211> LENGTH: 109
```

<212> TYPE: PRT
<213> ORGANISM: Artificial Sequence
<220> FEATURE:
<223> OTHER INFORMATION: antibody 219R0202 VL

<400> SEQUENCE: 32

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn His
            20                  25                  30

Leu Ala Trp Tyr Gln Gln Lys Pro Gly Lys Val Pro Lys Ser Leu Ile
        35                  40                  45

Tyr Ala Ala Ser Asn Leu His Ser Gly Val Pro Ser Lys Phe Ser Gly
    50                  55                  60

Ser Gly Ser Gly Thr His Phe Thr Leu Ile Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys Arg Thr
            100                 105
```

<210> SEQ ID NO 33
<211> LENGTH: 330
<212> TYPE: PRT
<213> ORGANISM: Artificial sequence
<220> FEATURE:
<223> OTHER INFORMATION: Human IgG1 Heavy chain constant region

<400> SEQUENCE: 33

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 34
<211> LENGTH: 326
<212> TYPE: PRT
<213> ORGANISM: Artificial sequence
<220> FEATURE:
<223> OTHER INFORMATION: Human IgG2 Heavy chain constant region

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 35
<211> LENGTH: 377
<212> TYPE: PRT
<213> ORGANISM: Artificial sequence
<220> FEATURE:
<223> OTHER INFORMATION: Human IgG3 Heavy chain constant region

<400> SEQUENCE: 35

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285
```

```
Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375


<210> SEQ ID NO 36
<211> LENGTH: 327
<212> TYPE: PRT
<213> ORGANISM: Artificial sequence
<220> FEATURE:
<223> OTHER INFORMATION: Human IgG4 Heavy chain constant region

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 37
<211> LENGTH: 30
<212> TYPE: PRT
<213> ORGANISM: Artificial Sequence
<220> FEATURE:
<223> OTHER INFORMATION: 30 amino acid linker

<400> SEQUENCE: 37

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 38
<211> LENGTH: 8
<212> TYPE: PRT
<213> ORGANISM: Artificial Sequence
<220> FEATURE:
<223> OTHER INFORMATION: FLAG Epitope

<400> SEQUENCE: 38

Asp Tyr Lys Asp Asp Asp Asp Lys
1               5
```